US009969972B2

(12) United States Patent
Nelson

(10) Patent No.: US 9,969,972 B2
(45) Date of Patent: May 15, 2018

(54) PLURIPOTENT STEM CELL CULTURE ON MICRO-CARRIERS

(71) Applicant: Janssen Biotech, Inc., Horsham, PA (US)

(72) Inventor: Shelley Nelson, Titusville, NJ (US)

(73) Assignee: Janssen Biotech, Inc., Horsham, PA (US)

( * ) Notice: Subject to any disclaimer, the term of this patent is extended or adjusted under 35 U.S.C. 154(b) by 0 days. days.

(21) Appl. No.: 14/631,019

(22) Filed: Feb. 25, 2015

(65) Prior Publication Data

US 2015/0166950 A1    Jun. 18, 2015

Related U.S. Application Data

(62) Division of application No. 12/621,686, filed on Nov. 19, 2009, now abandoned.

(60) Provisional application No. 61/116,447, filed on Nov. 20, 2008.

(51) Int. Cl.
*C12N 5/00* (2006.01)
*C12N 5/071* (2010.01)
*C12N 5/0735* (2010.01)

(52) U.S. Cl.
CPC .......... *C12N 5/0602* (2013.01); *C12N 5/0075* (2013.01); *C12N 5/0606* (2013.01); *C12N 5/0676* (2013.01); *C12N 2501/70* (2013.01); *C12N 2501/999* (2013.01); *C12N 2506/02* (2013.01); *C12N 2509/00* (2013.01); *C12N 2531/00* (2013.01)

(58) Field of Classification Search
CPC .................................................. C12N 5/0075
See application file for complete search history.

(56) References Cited

U.S. PATENT DOCUMENTS

| | | |
|---|---|---|
| 3,209,652 A | 10/1965 | Burgsmueller |
| 3,845,641 A | 11/1974 | Waller |
| 3,935,067 A | 1/1976 | Thayer |
| 4,499,802 A | 2/1985 | Simpson |
| 4,537,773 A | 8/1985 | Shenvi |
| 4,557,264 A | 12/1985 | Hinsch |
| 4,737,578 A | 4/1988 | Evans et al. |
| 5,215,893 A | 6/1993 | Mason et al. |
| 5,449,383 A | 9/1995 | Chatelier et al. |
| 5,525,488 A | 6/1996 | Mason et al. |
| 5,567,612 A | 10/1996 | Vacanti et al. |
| 5,665,568 A | 9/1997 | Mason et al. |
| 5,686,090 A | 11/1997 | Schilder et al. |
| 5,713,957 A | 2/1998 | Steele et al. |
| 5,716,810 A | 2/1998 | Mason et al. |
| 5,718,922 A | 2/1998 | Herrero-Vanrell |
| 5,759,830 A | 6/1998 | Vacanti et al. |
| 5,770,417 A | 6/1998 | Vacanti et al. |
| 5,780,454 A | 7/1998 | Adams et al. |
| 5,834,308 A | 11/1998 | Peck et al. |
| 5,843,780 A | 12/1998 | Thomson |
| 5,888,816 A | 3/1999 | Coon et al. |
| 5,908,782 A | 6/1999 | Marshank et al. |
| 5,914,262 A | 6/1999 | MacMichael et al. |
| 5,942,435 A * | 8/1999 | Wheeler ............ A01K 67/0271 435/325 |
| 6,001,647 A | 12/1999 | Peck et al. |
| 6,022,743 A | 2/2000 | Naughton et al. |
| 6,087,113 A | 6/2000 | Caplan et al. |
| 6,083,903 A | 7/2000 | Adams et al. |
| 6,200,806 B1 | 3/2001 | Thomson |
| 6,261,549 B1 | 6/2001 | Fernandez et al. |
| 6,281,012 B1 | 8/2001 | McIntosh et al. |
| 6,297,217 B1 | 10/2001 | Adams et al. |
| 6,306,424 B1 | 10/2001 | Vyakarnan et al. |
| 6,328,960 B1 | 12/2001 | McIntosh et al. |
| 6,331,298 B1 | 12/2001 | Ferguson et al. |
| 6,333,029 B1 | 12/2001 | Vyakarnam et al. |
| 6,365,149 B2 | 2/2002 | Vyakarnam et al. |
| 6,413,773 B1 | 7/2002 | Ptasznik et al. |
| 6,436,704 B1 | 8/2002 | Roberts et al. |
| 6,458,589 B1 | 10/2002 | Rambhatla |
| 6,458,593 B1 | 10/2002 | Musick et al. |
| 6,509,369 B2 | 1/2003 | Scott et al. |
| 6,521,427 B1 | 2/2003 | Evans |
| 6,534,084 B1 | 3/2003 | Vyakarnam et al. |
| 6,599,323 B2 | 7/2003 | Melican et al. |
| 6,617,152 B2 | 9/2003 | Bryhan et al. |
| 6,617,317 B1 | 9/2003 | Adams et al. |
| 6,626,950 B2 | 9/2003 | Brown et al. |
| 6,642,048 B2 | 11/2003 | Xu |
| 6,656,488 B2 | 12/2003 | Yi et al. |
| 6,670,127 B2 | 12/2003 | Evans |

(Continued)

FOREIGN PATENT DOCUMENTS

| CN | 1389565 A | 7/2002 |
|---|---|---|
| CN | 1602351 A | 3/2005 |

(Continued)

OTHER PUBLICATIONS

Inami et al., 2010, Immunology and Cell Biology, pp. 1-8.*
McClean et al., 2007, Stem Cells, vol. 25, pp. 29-38.*
Brevini et al., 2010, Theriogenology, vol. 74, pp. 544-550.*
Paris et al., 2010, Theriogenology, vol. 74, pp. 516-524.*
Munoz et al., 2008, Theriogenology, vol. 69, pp. 1159-1164.*
Fok et al., (2005, Stem Cells, vol. 23, pp. 1333-1342).*
D'Amour et al. (2006, Nature Biotechnology, vol. 24(11), pp. 1392-1401).*
Watanabe et al. (2007, Nat. Biot., vol. 25(6), pp. 681-686).*
Souza et al. (2005, Brazilian Archives of Biology and Technology, vol. 48, pp. 71-77).*
Philips et al., (2008, J. Biotechnology, vol. 138, pp. 24-32).*
King et al. (2007, Curr Opin Chem Biol, vol. 11(4), pp. 394-398.*
Abranches, et al., Expansion of Mouse Embryonic Stem Cells on Microcarriers, Biotechnology Bioengineering, Apr. 15, 2007, pp. 1211-1221, vol. 96, No. 6, Wiley InterScience.
Allegrucci, et al., Differences between Human Embryonic Stem Cell Lines, Human Reproduction Update, Aug. 26, 2006, pp. 1-18, Advance Access.
Amit, et al., Feeder Layer-and Serum-Free Culture of Human Embryonic Stem Cells, Biology of Reproduction, 2004, pp. 837-845, vol. 70.

(Continued)

*Primary Examiner* — Thaian N Ton
*Assistant Examiner* — David A. Montanari
(74) *Attorney, Agent, or Firm* — Lois A. Gianneschi

(57) ABSTRACT

The present invention is directed to methods for the growth, expansion and differentiation of pluripotent stem cells on micro-carriers.

15 Claims, 49 Drawing Sheets

(56) References Cited

U.S. PATENT DOCUMENTS

| | | |
|---|---|---|
| 6,703,017 B1 | 3/2004 | Peck et al. |
| 6,713,446 B2 | 3/2004 | Gupta |
| 6,793,945 B2 | 9/2004 | Bathurst et al. |
| 6,800,480 B1 | 10/2004 | Bodnar et al. |
| 6,815,203 B1 | 11/2004 | Bonner-Weir et al. |
| 6,958,319 B2 | 10/2005 | Gupta |
| 6,987,110 B2 | 1/2006 | Zhang et al. |
| 7,005,252 B1 | 2/2006 | Thomson et al. |
| 7,033,831 B2 | 4/2006 | Fisk et al. |
| 7,157,275 B2 | 1/2007 | Guarino et al. |
| 7,297,539 B2 | 11/2007 | Mandalam et al. |
| 7,326,572 B2 | 2/2008 | Fisk et al. |
| 7,371,576 B2 | 5/2008 | Tsang et al. |
| 7,410,798 B2 | 8/2008 | Mandalam et al. |
| 7,413,734 B2 | 8/2008 | Mistry et al. |
| 7,442,548 B2 | 10/2008 | Thomson et al. |
| 7,449,334 B2 | 11/2008 | Thomsom et al. |
| 7,510,873 B2 | 3/2009 | Mistry et al. |
| 7,510,876 B2 | 3/2009 | D'Amour et al. |
| 7,534,608 B2 | 5/2009 | Martinson et al. |
| 7,569,385 B2 | 8/2009 | Haas |
| 7,585,672 B2 | 9/2009 | Odorico et al. |
| 7,704,738 B2 | 4/2010 | D'Amour et al. |
| 7,993,920 B2 | 8/2011 | Martinson et al. |
| 8,187,878 B2 | 5/2012 | Dalton et al. |
| 8,859,286 B2 | 10/2014 | Agulnick |
| 2002/0072117 A1 | 6/2002 | Xu |
| 2003/0082155 A1 | 5/2003 | Habener |
| 2003/0138948 A1 | 7/2003 | Fisk et al. |
| 2003/0180903 A1 | 9/2003 | Bryhan et al. |
| 2004/0015805 A1 | 1/2004 | Kidd |
| 2004/0058412 A1 | 3/2004 | Ho et al. |
| 2004/0062753 A1 | 4/2004 | Rezania |
| 2004/0106196 A1 | 6/2004 | Fraser et al. |
| 2004/0121460 A1 | 6/2004 | Lumelsky et al. |
| 2004/0121461 A1 | 6/2004 | Honmou et al. |
| 2004/0132729 A1 | 7/2004 | Salituro et al. |
| 2004/0161419 A1 | 8/2004 | Strom et al. |
| 2004/0171623 A1 | 9/2004 | Reynolds et al. |
| 2004/0209901 A1 | 10/2004 | Adams et al. |
| 2004/0220393 A1 | 11/2004 | Ward et al. |
| 2004/0241761 A1 | 12/2004 | Sarvetnick |
| 2005/0037491 A1 | 2/2005 | Mistry et al. |
| 2005/0053588 A1 | 3/2005 | Yin et al. |
| 2005/0054093 A1 | 3/2005 | Haas |
| 2005/0054098 A1 | 3/2005 | Mistry et al. |
| 2005/0054102 A1 | 3/2005 | Wobus et al. |
| 2005/0058631 A1 | 3/2005 | Kihm et al. |
| 2005/0063961 A1 | 3/2005 | Friedlander et al. |
| 2005/0148070 A1 | 7/2005 | Thomson et al. |
| 2005/0158852 A1 | 7/2005 | D'Amour et al. |
| 2005/0187298 A1 | 8/2005 | Vasudevan et al. |
| 2005/0037488 A1 | 9/2005 | Mitalipova |
| 2005/0208029 A1 | 9/2005 | Umezawa et al. |
| 2005/0233446 A1 | 10/2005 | Parsons |
| 2005/0244962 A1 | 11/2005 | Thomson et al. |
| 2005/0260749 A1 | 11/2005 | Odorico et al. |
| 2005/0266554 A1 | 12/2005 | D'Amour |
| 2006/0003446 A1 | 1/2006 | Keller |
| 2006/0030042 A1 | 2/2006 | Brivaniou et al. |
| 2006/0040387 A1 | 2/2006 | Fisk |
| 2006/0148081 A1 | 7/2006 | Kelly et al. |
| 2006/0194315 A1 | 8/2006 | Condie et al. |
| 2006/0194321 A1 | 8/2006 | Colman et al. |
| 2006/0281174 A1 | 12/2006 | Xu et al. |
| 2007/0010011 A1 | 1/2007 | Parsons |
| 2007/0082397 A1 | 4/2007 | Hasson et al. |
| 2007/0122903 A1 | 5/2007 | Rezania et al. |
| 2007/0122905 A1 | 5/2007 | D'Amour et al. |
| 2007/0154981 A1 | 7/2007 | Hori et al. |
| 2007/0155013 A1 | 7/2007 | Akaike et al. |
| 2007/0155661 A1 | 7/2007 | Kim |
| 2007/0254359 A1 | 11/2007 | Rezania |
| 2007/0259421 A1 | 11/2007 | D'Amour et al. |
| 2007/0259423 A1 | 11/2007 | Odorico |
| 2007/0264713 A1 | 11/2007 | Terstegge et al. |
| 2008/0091234 A1 | 4/2008 | Kladakis et al. |
| 2008/0159994 A1 | 7/2008 | Mantalaris et al. |
| 2008/0171385 A1* | 7/2008 | Bergendahl ......... C12N 5/0606 435/366 |
| 2008/0241107 A1 | 10/2008 | Copland, III et al. |
| 2008/0260700 A1 | 10/2008 | Accili et al. |
| 2008/0267926 A1 | 10/2008 | Martinson et al. |
| 2008/0268533 A1 | 10/2008 | Dalton et al. |
| 2008/0268534 A1 | 10/2008 | Robins et al. |
| 2009/0004152 A1 | 1/2009 | Martinson et al. |
| 2009/0029462 A1 | 1/2009 | Beardsley et al. |
| 2009/0053182 A1 | 2/2009 | Ichim et al. |
| 2009/0093055 A1 | 4/2009 | Fisk et al. |
| 2009/0170198 A1 | 7/2009 | Rezania |
| 2009/0203141 A1 | 8/2009 | Lin et al. |
| 2009/0263896 A1 | 10/2009 | Kelly et al. |
| 2009/0269845 A1 | 10/2009 | Rezania et al. |
| 2009/0298178 A1 | 12/2009 | D'Amour |
| 2009/0325293 A1 | 12/2009 | Davis et al. |
| 2010/0003749 A1 | 1/2010 | Uchida et al. |
| 2010/0015100 A1 | 1/2010 | Xu |
| 2010/0015711 A1 | 1/2010 | Davis et al. |
| 2010/0028307 A1 | 2/2010 | O'Neil |
| 2010/0093053 A1 | 4/2010 | Oh et al. |
| 2010/0112691 A1 | 5/2010 | Green et al. |
| 2010/0112693 A1 | 5/2010 | Rezania et al. |
| 2010/0255580 A1 | 10/2010 | Rezania |
| 2011/0014703 A1 | 1/2011 | Xu et al. |
| 2011/0104805 A1 | 5/2011 | Fung et al. |
| 2011/0151560 A1 | 6/2011 | Xu |
| 2011/0151561 A1 | 6/2011 | Davis et al. |
| 2011/0229441 A1 | 9/2011 | Benchoua et al. |
| 2011/0280842 A1 | 11/2011 | Melton et al. |
| 2011/0281355 A1 | 11/2011 | Xu |
| 2012/0045830 A1 | 2/2012 | Green et al. |
| 2012/0052576 A1 | 3/2012 | Rezania |
| 2012/0190111 A1 | 7/2012 | Davis et al. |
| 2012/0264209 A1 | 10/2012 | Odorico et al. |
| 2013/0189777 A1 | 7/2013 | Rezania |
| 2013/0224156 A1 | 8/2013 | Takahashi et al. |
| 2014/0186953 A1 | 7/2014 | Rezania |

FOREIGN PATENT DOCUMENTS

| | | |
|---|---|---|
| CN | 1671835 A | 9/2005 |
| CN | 1946838 A | 4/2007 |
| CN | 101092606 A | 12/2007 |
| CN | 101310012 A | 11/2008 |
| CN | 101410509 A | 4/2009 |
| CN | 101541953 A | 9/2009 |
| CN | 101611016 A | 12/2009 |
| EP | 0363125 A2 | 4/1990 |
| EP | 348969 B1 | 5/1993 |
| EP | 0617126 B1 | 9/1994 |
| EP | 0800829 B1 | 10/1997 |
| EP | 0092302 B1 | 11/2006 |
| EP | 1873237 A1 | 1/2008 |
| EP | 1391505 B1 | 1/2009 |
| EP | 2088190 A1 | 8/2009 |
| EP | 2479260 B1 | 6/2016 |
| GB | 2484873 B2 | 4/2014 |
| JP | 2005506074 A2 | 3/2003 |
| JP | 2006-500003 A2 | 1/2006 |
| JP | 2008500809 A2 | 1/2008 |
| JP | 2009513143 A2 | 4/2009 |
| KR | 10-2008-0020098 A | 3/2008 |
| RU | 2359671 C2 | 6/2009 |
| WO | WO199219759 A2 | 2/1992 |
| WO | 1996040172 A1 | 12/1996 |
| WO | 199847892 A1 | 10/1998 |
| WO | WO199920741 A1 | 4/1999 |
| WO | 200029549 A1 | 5/2000 |
| WO | 200123528 A1 | 4/2001 |
| WO | WO200151616 A2 | 7/2001 |
| WO | WO200181549 A3 | 11/2001 |
| WO | 200246183 A2 | 6/2002 |
| WO | 200246197 A1 | 6/2002 |
| WO | 2002086107 A2 | 10/2002 |

(56) References Cited

FOREIGN PATENT DOCUMENTS

| | | |
|---|---|---|
| WO | 02092756 A2 | 11/2002 |
| WO | 03033697 A1 | 4/2003 |
| WO | 2003026584 A2 | 4/2003 |
| WO | 2003029445 A1 | 4/2003 |
| WO | 2003042405 A2 | 5/2003 |
| WO | WO200305049 A1 | 6/2003 |
| WO | 2003054169 A1 | 7/2003 |
| WO | 2003062405 A2 | 7/2003 |
| WO | 2003095452 A1 | 11/2003 |
| WO | 03103972 A1 | 12/2003 |
| WO | WO2003102134 A2 | 12/2003 |
| WO | 2004016747 A2 | 2/2004 |
| WO | WO2004011621 A2 | 2/2004 |
| WO | 2004044158 A1 | 5/2004 |
| WO | 2004050827 A2 | 6/2004 |
| WO | 2004055155 A2 | 7/2004 |
| WO | 2004073633 A1 | 9/2004 |
| WO | 2004087885 A | 10/2004 |
| WO | WO2004090110 A2 | 10/2004 |
| WO | 2004067001 A1 | 12/2004 |
| WO | 2005080598 A1 | 1/2005 |
| WO | WO2005001077 A2 | 1/2005 |
| WO | 2005017117 A2 | 2/2005 |
| WO | WO2005014799 A1 | 2/2005 |
| WO | 2005058301 A1 | 6/2005 |
| WO | 2005063971 A1 | 7/2005 |
| WO | 2005065354 A2 | 7/2005 |
| WO | 2005080551 A2 | 9/2005 |
| WO | 2005086845 A2 | 9/2005 |
| WO | 2005097977 A2 | 10/2005 |
| WO | 2005097980 A2 | 10/2005 |
| WO | WO2005116073 A3 | 12/2005 |
| WO | 2006020919 A2 | 2/2006 |
| WO | 2006088867 A2 | 2/2006 |
| WO | WO2006016999 A1 | 2/2006 |
| WO | 2006026473 A1 | 3/2006 |
| WO | 2006029197 A1 | 3/2006 |
| WO | 2006036925 A1 | 4/2006 |
| WO | 2006080952 A2 | 8/2006 |
| WO | 2006083782 A2 | 8/2006 |
| WO | 2006100490 A1 | 9/2006 |
| WO | WO2006094286 A2 | 9/2006 |
| WO | 2006108361 A1 | 10/2006 |
| WO | 2006113470 A2 | 10/2006 |
| WO | 2006114098 A2 | 11/2006 |
| WO | 2006126574 A1 | 11/2006 |
| WO | 2006135824 A1 | 12/2006 |
| WO | 2006137787 A1 | 12/2006 |
| WO | 2006138433 A2 | 12/2006 |
| WO | 2007002086 A1 | 1/2007 |
| WO | 2007003525 A2 | 1/2007 |
| WO | 2007012144 A1 | 2/2007 |
| WO | 2007016485 A2 | 2/2007 |
| WO | 2007026353 A2 | 3/2007 |
| WO | 2007030870 A1 | 3/2007 |
| WO | WO2007027157 A1 | 3/2007 |
| WO | 2007047509 A1 | 4/2007 |
| WO | 2007051038 A2 | 5/2007 |
| WO | 2007069666 A1 | 6/2007 |
| WO | WO2007082963 A1 | 7/2007 |
| WO | 2007101130 A2 | 9/2007 |
| WO | WO2007103282 A1 | 9/2007 |
| WO | 2007127927 A2 | 11/2007 |
| WO | 2007143193 A1 | 12/2007 |
| WO | 2007149182 A2 | 12/2007 |
| WO | WO2007139929 A2 | 12/2007 |
| WO | 2008004990 A2 | 1/2008 |
| WO | 2008013664 A1 | 1/2008 |
| WO | 2008015682 A2 | 2/2008 |
| WO | 2008035110 A1 | 3/2008 |
| WO | 2008036447 A2 | 3/2008 |
| WO | 2008048671 A1 | 4/2008 |
| WO | WO2008048647 A1 | 4/2008 |
| WO | 2009096049 A1 | 5/2008 |
| WO | 2008086005 A1 | 7/2008 |
| WO | 2008094597 A2 | 8/2008 |
| WO | 2008102118 A1 | 8/2008 |
| WO | 2009012428 A1 | 1/2009 |
| WO | 2009018453 A1 | 2/2009 |
| WO | 2009027644 A2 | 3/2009 |
| WO | WO2009048675 A1 | 4/2009 |
| WO | 2009061442 A1 | 5/2009 |
| WO | 2009070592 A1 | 6/2009 |
| WO | 2009096902 A1 | 8/2009 |
| WO | 2009101407 A2 | 8/2009 |
| WO | WO2009105570 A2 | 8/2009 |
| WO | 2009110215 A1 | 9/2009 |
| WO | 2009131568 A1 | 10/2009 |
| WO | 2009132083 A2 | 10/2009 |
| WO | 2009154606 A1 | 12/2009 |
| WO | 2010000415 A1 | 1/2010 |
| WO | 2010002846 A1 | 1/2010 |
| WO | 2010051213 A1 | 5/2010 |
| WO | 2010051223 A1 | 5/2010 |
| WO | 2010053472 A1 | 5/2010 |
| WO | 2010057039 A2 | 5/2010 |
| WO | 2010059775 A1 | 5/2010 |
| WO | 2011011300 A2 | 1/2011 |
| WO | 2011067465 A1 | 6/2011 |
| WO | 2011108993 A1 | 9/2011 |
| WO | 2011123572 A1 | 10/2011 |
| WO | 2011139628 A1 | 11/2011 |
| WO | 2012019122 A2 | 2/2012 |
| WO | 2012117333 A1 | 9/2012 |
| WO | 2013055397 A1 | 4/2013 |
| WO | 2013055834 A2 | 4/2013 |
| WO | 2013095953 A1 | 6/2013 |
| WO | 2013184888 A1 | 12/2013 |
| WO | 2014033322 A1 | 3/2014 |
| WO | 2014105546 A1 | 7/2014 |
| WO | 2014152321 A1 | 9/2014 |

OTHER PUBLICATIONS

Brevini, et al., No Shortcuts to Pig Embryonic Stem Cells, Theriogenology, 2010, pp. 544-550, vol. 74.

D'Amour et al., Efficient differentiation of human embryonic stem cells to definitive endoderm, Nature Biotechnology, Oct. 28, 2005, 1-8, :W.1038/nbt1163, Nature Publishing Group.

D'Amour et al., Production of pancreatic hormone—expressing endocrine cells from human embryonic stem cells, Nature Biotechnology, Oct. 19, 2006, 1392-1401, 24-11, Nature Publishing Group, US.

Donovan, et al., The End of the Beginning for Pluripotent Stem Cells, Nature, Nov. 2001, pp. 92-97, vol. 414.

Fok, et al., Shear-Controlled Single-Step Mouse Embryonic Stem Cell Expansion and Embryoid Body-Based Differentation, Stem Cells, 2005, pp. 1333-1342, vol. 23.

Ginis, et al., Differences Between Human and Mouse Embryonic Stem Cells, Developmental Biology, 2004, pp. 360-380, vol. 269.

Kubo et al., Development of definitive endoderm from embryonic stem cells in culture, Development, 2004, 1651-1662, 131, The Company of Biologists.

Lim, et al., Proteome Analysis of Conditioned Medium from Mouse Embryonic Fibroblast Feeder Layers which Support the Growth of Human Embryonic Stem Cells, Proteomics, 2002, pp. 1187-1203, vol. 2.

Ludwig, et al., Derivation of Human Embryonic Stem Cells in Defined Conditions, Nature Biotechnology, Feb. 2006, pp. 185-187, vol. 24 No. 2.

McLean et al., Activin A Efficiently Specifies Definitive Endoderm from Human Embryonic Stem Cells Only When Phosphatidylinositol 3-Kinase Signaling Is Suppressed, Stem Cells, 2007, 29-38, 25, AlphaMed Press.

Munoz, et al., Conventional Pluripotency Markers are Unspecific for Bovine Embryonic-Derived Cell-Lines, Theriogenology, 2008, pp. 1159-1164, vol. 69.

Oh, et al., Human Embryonic Stem Cells: Technological Challenges Towards Therapy, Clinical and Experimental Pharmacology and Physiology, 2006, pp. 489-495, vol. 33.

(56) References Cited

OTHER PUBLICATIONS

Paris, et al., Equine Embryos and Embryonic Stem Cells: Defining Reliable Markers of Pluripotency Theriogeneology, 2010, pp. 516-524, vol. 74.
Phillips, et al., Attachment and Growth of Human Embryonic Stem Cells on Microcarriers, Journal of Biotechnology, 2008, pp. 24-32, vol. 138.
Prowse, et al., A Proteome Analysis of Conditioned Media from Human Neonatal Fibroblasts Used in the Maintenance of Human Embryonic Stem Cells, Proteomics, 2005, pp. 978-989, vol. 5.
Sato, et al., Molecular Signature of Human Embryonic Stem Cells and its Comparison with the Mouse, Developmental Biology, Apr. 23, 2003, pp. 404-413, vol. 260.
Thomson et al., Embryonic Stem Cell Lines Derived from Human Blastocysts, Science, Nov. 6, 1998, 1145-1147, 282, HighWire Press.
Thomson et al., Isolation of a primate embryonic stem cell line, Developmental Biology, Aug. 1995, 7844-7848, 92, Proc. Natl. Acad. Sci, US.
Watanabe, et al., A Rock Inhibitor Permits Survival of Dissociated Human Embryonic Stem Cells, Nature Biotechnology, 2007, pp. 681-686, vol. 25, No. 6.
Wei, et al., Transcriptome Profiling of Human and Murine ESCs Identifies Divergent Paths Required to Maintain the Stem Cell State, Stem Cells, 2005, pp. 166-185, vol. 23.
Xu, et al., Feeder-free Growth of Undifferentiated Human Embryonic Stem Cells, Nature Biotechnology, 2001, pp. 971-974, vol. 19.
Abe, et al., Evidence That Pl3K, Rac, Rho, and Rho Kinase Are Involved in Basic Fibroblast Growth Factor-Stimulated Fibroblast-Collagen Matrix Contraction, Journal of Cellular Biochemistry, 2007, pp. 1290-1299, vol. 102.
Abeyta, et al., Unique Gene Expression Signatures of Independently-Derived Human Embryonic Stem Cells Lines, Human Molecular Genetics, Jan. 28, 2004, pp. 601-608, vol. 13, No. 6, Oxford University Press.
Ackermann, et al., Molecular Regulation of Pancreatic B-Cell Mass Development, Maintenance, and Expansion, Journal of Molecular Endocrinology, 2007, pp. 193-206, vol. 38.
Adams, et al., Proteasome Inhibition in Cancer: Development of PS-341, Seminars in Oncology, 2001, pp. 613-619, vol. 28, No. 6.
Age-Related Eye Disease Study Research Group, A Randomized, Palcebo-Controlled, Clinical Trial of High-Dose Supplementation with Vitamins C and E, Beta Carotene, and Zinc for Age-Related Macular Degeneration and Vision Loss, Arch Ophthalmology, 2001, pp. 1417-1436, AREDS Report No. 8, vol. 119.
Ali, et al., Exploitation of Protein Kinase C: A Useful Target for Cancer Therapy, Cancer Treatment Reviews, 2009, pp. 1-8, vol. 35.
Almond, et al., The Proteasome: A Novel Target for Cancer Chemotherapy, Leukemia, 2002, pp. 433-443, vol. 16.
Amit et al., Human Feeder Layers for Human Embryonic Stem Cells, Biology of Reproduction, Jan. 22, 2003, pp. 2150-2156, 68, No. 6, Society for the Study of Reproduction, Inc.
Amit, et al., Clonally Derived Human Embryonic Stem Cell Lines Maintain Pluripotency and Proliferative Potential for Prolonged Periods of Culture, Developmental Biology, 2000, pp. 271-278, vol. 227.
Amit, et al., Dynamic Suspension Culture for Scalable Expansion of Undifferentiated Human Pluripotent Stem Cells, Nature Protocols, Apr. 7, 2011, pp. 572-579, vol. 6, No. 5.
Arai, et al., Purification of Recombinant Activin A Using the Second Follistatin Domain of Follistatin-Related Gene (FLRG), Protein Expression & Purification, 2006, pp. 78-82, vol. 49.
Armstrong, et al., The Role of Pl3K/AKT, MAPK/ERK and NFκβ Signalling in the Maintenance of Human Embryonic Stem Cell Pluripotency and Viability Highlighted by Transcriptional Profiling and Functional Analysis, Human Molecular Genetics, 2006, pp. 1894-1913, vol. 15, No. 11.
Assady, et al., Insulin Production by Human Embryonic Stem Cells, Diabetes, 2001, pp. 1691-1697, vol. 50.

Baertschiger, et al., Mesenchymal Stem Cells Derived From Human Exocrine Pancreas Express Transcription Factors Implicated in Beta-Cell Development, Pancreas, 2008, pp. 75-84, vol. 37, No. 1.
Baetge, Production of B-Cells from Human Embryonic Stem Cells, Diabetes, Obesity, Metabolism, 2008, pp. 186-194, vol. 10, Supplement 4.
Bai, et al., Glucagon-Like Peptide-1 Enhances Production of Insulin in Insulin-Producing cells Derived from Mouse Embryonic Stem Cells, Journal of Endocrinology, 2005, pp. 343-352, vol. 186, No. 2.
Balsam, et al., Haematopoeitic Stem Cells Adopt Mature Haeatopoietic Fates in Ischaemic Myocardium, Nature, Apr. 8, 2004, pp. 668-673, vol. 428, Nature Publishing Group.
Bandyopadhyay, et al., Inhibition of Pulmonary and Skeletal Metastasis by a Transforming Growth Factor-B Type I Receptor Kinase Inhibitor, Cancer Research, 2006, pp. 6714-6721, vol. 66, No. 13.
Barclay, et al., The Leucocyte Antigen Facts Book, The Leucocyte Antigen Facts Book, 1997, Textbook, 2[sup] edition, Academic Press.
Bellinger, et al., Swine Models of Type 2 Diabetes Mellitus: Insulin Resistance, Glucose Tolerance, and Cardiovascular Complications, ILAR Journal, 2006, pp. 243-258, vol. 47, No. 3.
Beltrami, et al., Adult Cardiac Stem Cells are Multipotent and Support Myocardial Regeneration, Cell, Sep. 19, 2003, pp. 763-776, vol. 114, Cell Press.
Best, et al., Embryonic Stem Cells to Beta-Cells by Understanding Pancreas Development, Molecular and Cellular Endorinology, 2008, pp. 86-94, vol. 288.
Bigdeli, et al., Adaptation of Human Embryonic Stem Cells to Feeder-Free and Matrix-Free Culture Conditions Directly on Plastic Surfaces, Journal of Biotechnology, 2008, pp. 146-153, vol. 133.
Blin, et al., A Purified Population of Multipotent Cardiovascular Progenitors Derived from Primate Pluripotent Stem Cells Engrafts in Postmyocardial Infarcted Nonhumans Primates, The Journal of Clinical Investigation, Apr. 2010, pp. 1125-1139, vol. 120, No. 4.
Blyszczuk et al., Expression of Pax4 in embryonic stem cells promotes differentiation of nestin-positive progenitor and insulin-producing cells, Proceedings of the National Academy of Sciences, Feb. 4, 2003, 998-1003, 100-3, National Academy of Sciences.
Bo, et al., Research Progress of Pancreatic Islet Development and Pancreatic Stem Cells, Journal of Clinical Surgery, 2009, pp. 208-210, vol. 17, No. 3.
Bocian-Sobkowska, et al., Polyhormonal Aspect of the Endocrine Cells of the Human Fetal Pancreas, Histochem Cell Biol, 1999, pp. 147-153, vol. 112, Issue 2.
Bonner-Weir et al., In vitro cultivation of human islets from expanded ductal tissue, Proceedings of the National Academy of Sciences, Jul. 5, 2000, pp. 7999-8004, vol. 97-14, National Academy of Sciences.
Borowiak, et al., How to Make AB Cells, Current Opinion Cell Biology, 2009, pp. 727-732, vol. 21, Issue 6.
Borowitz, et al., Prognostic Significance of Fluorescence Intensity of Surface Marker . . . , Blood, Jun. 1, 1997, pp. 3960-3966, vol. 89-11, American Society of Hematology, Washington, D.C., US.
Braam, et al., Improved Genetic Manipulation of Human Embryonic Stem Cells, Nature Methods, May 2008, pp. 389-392, vol. 5, No. 5.
Brakenhoff et al., Development of a Human Interleukin-6 Receptor Antagonist, Journal of Biological Chemistry, Jan. 7, 1994, pp. 86-93, vol. 269-1, US.
Brambrink, et al., Sequential Expression of Pluripotency Markers During Direct Reprogramming of Mouse Somatic Cells, Cell Stem Cell, 2008, pp. 151-159, vol. 2.
Brevig, et al., The Recognition of Adsorbed and Denatured Proteins of Different Topographies by β2 Integrins and Effects on Leukocyte Adhesion and Activation, Biomaterials, 2005, pp. 3039-3053, vol. 26.
Brevini et al., Embryonic Stem Cells in Domestic Animals, Theriogeneology, 2010, pp. 544-550, vol. 74.
Bross, et al., Approval Summary for Bortezomib for Injection in the Treatment of Multiple Myeloma, Clinical Cancer Research, Jun. 15, 2004, pp. 3954-3964, vol. 10.

(56) References Cited

OTHER PUBLICATIONS

Brown, et al., Optimal Control of Blood Glucose: The Diabetic Patient or the Machine?, Science Translation Medicine, Apr. 14, 2010, pp. 1-5, vol. 2 Issue 27.
Burkard et al., Conditional Neuronal Nitric Oxide Synthase Overexpression Impairs Myocardial Contractility, Circulation Reseach, Jan. 18, 2007, pp. e32-e44, vol. 100.
Buzzard et al., Karyotype of human ES cells during extended culture, Nature Biotechnology, Apr. 1, 2004, pp. 381-382, vol. 22-4, Nature Publishing Group.
Cai, et al., Generation of Homogeneous PDX1+Pancreatic Progenitors from Human ES Cell-derived Endoderm Cells, Journal of Molecular Cell Biology, Nov. 12, 2009, pp. 50-60, vol. 2.
Cao, et al., High Glucose is Necssary for Complete Maturation of Pdx1-VP16-Expressing Hepatic Cells into Functional Insulin-Producing Cells, Diabetes, 2004, pp. 3168-3176, vol. 53.
Castaing, et al., Blood Glucose Normalization Upon Transplantation of Human Embryonic Pancreas into Beta-Cell-Deficient SCID Mice, Diabetologica, 2001, pp. 2066-2076, vol. 44.
Chambers, et al., Functional Expression Cloning of Nanog, a Pluripotency Sustaining Factor in Embryonic Stem Cells, Cell, May 30, 2003, pp. 643-655, vol. 113.
Chapple, et al., Unfolding Retinal Dystrophies: A Role for Molecular Chaperones?, Trends in Molecluar Medicine, 2001, pp. 414-421, vol. 7, No. 9.
Chen, et al., A Small Molecule that Directs Differentiation of Human ESCs into the Pancreatic Lineage, Nature Chemical Biology, Apr. 11, 2009, pp. 258-265, vol. 5, No. 4.
Chen, et al., Chemically Defined Conditions for Human iPSC Derivation and Culture, Nature Methods, 2011, pp. 424-429, vol. 8, Issue 5.
Chen, et al., Differentiation of Embryonic Stem Cells Towards Pancreatic Progenitor Cells and their Transplantation into Strepozotocin-Induced Diabetic Mice, Cell Biology International, 2008, pp. 456-461, vol. 32.
Chen, et al., Differentiation of Rat Marrow Mesencymal Stem Cells in Pancreatic Islet Beta-Cells, World Journal of Gastroenterology, Oct. 15, 2004, 3016-3020, 10.
Chen, et al., Retinoic Acid Signaling is Essential for Pancreas Development and Promotes Endocrine at the Expense of Exocrine Cell Differentiation in Xenopus, Developmental Biology, 2004, pp. 144-160, vol. 271.
Cheon et al., Secretory Leukocyte Protease Inhibitor (SLPI) Regulate the Embryonic Differentiation During Periimplantation Stage, Biology of Reproduction, 2007, p. 64, vol. 77, Society for the Study of Reproduction, Inc.
Cheon, et al., Defined Feeder-Free Culture System of Human Embryonic Stem Cells, Biol Reprod, 2005, 105.046870, DOI10/1095.
Chetty, et al., A Simple Tool to Improve Pluripotent Stem Cell Differentiation, Nature Methods, 2013, pp. 553-558, vol. 10, No. 6.
Choi, et al., In Vitro Trans-Differentiation of Rat Mesenchymal Cells into Insulin-Producing Cells by Rat Pancreatic Extract, Biochemical and Biophysical ResearchCommunications, 2005, pp. 1299-1305, vol. 330.
Chung, et al., Human Embryonic Stem Cell Lines Generated without Embryo Destruction, Cell Stem Cell, 2008, pp. 113-117, vol. 2.
Corbeil, et al., Rat Prominin, Like its Mouse and Human Orthologues, is a Pentaspan Membrane Glycoprotein, Biochemical and Biophysical Research Communications, 2001, pp. 939-944, vol. 285, No. 4.
Crane, et al., An Embryogenic Model to Explain Cytogenetic Inconsistencies Observed in Chorionic Villus Versus Fetal Tissue, Prenatal Diagnosis, 1988, pp. 119-129, vol. 8.
Cresta, et al., Phase I Study of Bortezomib with Weekly Paclitaxel in Patients with Advanced Solid Tumours, European Journal of Cancer, 2008, pp. 1829-1834, vol. 44.
Cure, et al., Improved Metabolic Control and Quality of Life in Seven Patients with Type 1 Diabetes Following Islet After Kidney Transplantation, Cell Therapy and Islet Transplantation, Mar. 27, 2008, pp. 801-812, vol. 85, No. 6.
D'Amour et al, Production of Pancreatic Hormone-Expressing Endocrine Cells from Human Embryonic Stem Cells, Nature Biotechnology, 2006, pp. 1392-1401, vol. 24.
Damy, et al., Increased Neuronal Nitric Oxide Synthase-Derived NO Production in the Failing Human Heart, Research Letters, Apr. 24, 2004, pp. 1365-1367, vol. 363.
David M. Chacko, et al., Survival and Differentiation of Cultured Retinal Progenitors Transplanted in the Subretinal Space of the Rat, Biochemical and Biophysical Research Communications, 2000, pp. 842-846, vol. 268, Academic Press.
De Coppi, et al., Isolation of Amniotic Stem Cell Lines with Potential for Therapy, Nature Biotechnology, 2007, pp. 100-106, vol. 25, No. 1.
De Rosa, 11-color, 13-parameter flow cytometry: Identification of . . . , Nature, Feb. 1, 2001, 245-248, 7-2, Nature Publishing Group, US.
Dekker, et al., Adhesion of Endothelial Cells and Adsorption of Serum Proteins on Gas Plasma-Treated Polytetrafluoroethylene, Biomaterials, 1991, pp. 130-138, vol. 12.
Denning, et al., Common Culture Conditions for Maintenance and Cardiomyocyte Differentiation of the Human Embryonic Stem Cell Lines, BG01 and HUES-7, Int. J. Del. Biol., 2006, pp. 27-37, vol. 50.
Deramaudt, et al., The PDX1 Homeodomain Transcription Factor Negatively Regulates the Pancreatic Ductal Cell-specific Keratin 19 Promoter*, Journal of Biological Chemistry, 2006, pp. 38385-38395, vol. 281, No. 50.
Dorrell, et al., Editorial, Stem Cell Research, 2008, pp. 155-156, vol. 1.
Doyle, et al., Cell and Tissue Culture: Laboratory Procedures in Biotechnology, Cell and Tiossue Culture: Laboratory Procedures in Biotechnology, 1995, Textbook, Textbook, Wiley.
Draper, et al., Recurrent Gain of Chromosomes 17q and 12 in Cultured Human Embryonic Stem Cells, Nature Biotechnology, 2004, pp. 53-54, vol. 22, No. 1.
Draper, et al., Surface Antigens of Human Embryonic Stem Cells: Changes Upon Differentiation in Culture, Journal Anatomy, 2002, pp. 249-258, vol. 200, Anatomical Society of Great Britain and Ireland.
Dufour, et al., Development of an Ectopic Site for Islet Transplantation Using Biodegradable Scaffolds, Tissue Engineering, 2005, pp. 1323-1331, vol. 11, No. 9/10.
Dupont-Gillain, et al., Plasma-Oxidized Polystyrene: Wetting Properties and Surface Reconstruction, Langmuir, 2000, pp. 8194-8200, vol. 16.
Edlund, Pancreatic Organogenisis—Pancreatic Mechanisims and Implications for Therapy, Nature, Jul. 1, 2002, pp. 524-532, vol. 3, Nature Publishing Group, US.
Eguizabal, et al., Embryonic Stem Cells/Induced Pluriptent Stem Complete Meiosis from Human Induced Pluripotent Stem Cells, Stem Cells, 2011, pp. 1186-1195, vol. 29.
Ellerstrom, et al., Derivation of a Xeno-Free Human Embryonic Stem Cell Line, Stem Cells, 2006, pp. 2170-2176, vol. 24.
Ellerstrom, et al., Facilitated Expansion of Human Embryonic Stem Cells by Single-Cell Enzymatic Dissociation, Stem Cells, 2007, pp. 1690-1696, vol. 25, No. 7.
Ellmers, et al., Transforming Growth Factor-B Blockade Down-Regulates the Renin-Angiotensin System and Modifies Cardiac Remodling after Myoardial Infarction, Endocrinology, Jul. 24, 2008, pp. 5828-5834, vol. 149—Issue 11, The Endocrine Society.
Enzmann, et al., Enhanced Induction of RPE Lineage Markers in Pluripootent Neural Stem Cells Engrafted into the Adult Rat Subretinal Space, Ophthamology & Visual Science, Dec. 2003, pp. 5417-5422, vol. 44, No. 12, Association for Research in Vision and Ophthamology.
Eventov-Friedman, et al., Embryonic Pig Pancreatic Tissue Transplantation for the Treatment of Diabetes, PLOS Medicine, Jul. 2006, e215, pp. 1165-1177, vol. 3, Issue 7.
Ezashi, et al., Low O2 Tensions and the Prevention of Differentiation of hES Cells, Proceedings of the National Academy of Sciences of USA, Mar. 29, 2005, pp. 4783-4788, vol. 102, No. 13.

(56) References Cited

OTHER PUBLICATIONS

Fauza, Amniotic Fluid and Placental Stem Cells, Ballieres Best Practice and Research Clinical Obsterics and Gynaecology, 2004, pp. 877-891, vol. 18, No. 6.

Fidler et al., Selective Immunomodulation by the Antineoplastic Agent Mitoxantrone, Journal of Immunology, Jul. 15, 1986, pp. 727-732, vol. 137-2, American Society of Immunologists, US.

Fischer, et al., Residues in the C-Terminal Region of Activin A Determine Specificity for Follistatin and Type II Receptor Binding, Journal of Endocrinology, 2003, pp. 61-68, vol. 176, Society for Endocrinology.

Florio, et al., Activin A Stimulates Insulin Secretion in Cultured Human Pancreatic Islets, J. Endocrinol. Invest., 2000, pp. 231-234, vol. 23.

Foster, et al., Differentiation of Transplanted Microencapsulated Fetal Pancreatic Cells, Experimental Transplantation, Jun. 15, 2007, pp. 1440-1448, vol. 83, No. 11.

Frandsen et al., Activin B mediated induction of Pdx1 in human embryonic stemcell derived embryoid bodies, Biochemical and Biophysical Research Communications, Aug. 15, 2007, pp. 568-574, vol. 362, Elsevier Inc.

Frigui, et al., A Robust Competitive Clustering Algorithm With Applications in Computer Vision, IEEE Transactions on Pattern Analysis and Machine Intelligence, May 1, 1999, pp. 450-465, vol. 21, No. 5, IEEE, US.

Fung, et al., The Effect of Medical Therapy and Islet Cell Transplantation on Diabetic Nephropathy: An Interim Report, Transplantation, Jul. 15, 2007, pp. 17-22, vol. 84, No. 1.

Furue, et al., Heparin Promotes the Growth of Human Embryonic Stem Cells in a Defined Serum-Free Medium, Proceedings of the National Academy of Sciences, Sep. 9, 2008, pp. 13409-13414, vol. 105, No. 36.

Gadue, et al., Wnt and TGB-B Signaling Are Required for the Induction of an in vitro Model of Primitive Streak Formation Using Embryonic Stem Cells, Proceedings of the National Academy of Sciences, Nov. 7, 2006, pp. 16806-16811, vol. 103-45, National Academy of Sciences, US.

Gaspar, et al., Inhibition of Transforming Growth Factor Signaling Reduces Pancreatic Adenocarcinoma Growth and Invasiveness, Molecular Pharmacology, 2007, pp. 152-161, vol. 72, Issue 1.

Gellibert, et al., Identification of 1,5-Naphthyridine Derivatives as a Novel Series of Potent and Selective TGF-B Type I Receptor Inhibitor, J. Med. Chem, 2004, pp. 4494-4506, vol. 47, No. 18.

Gershengorn et al., Epithelial-to-Mesenchymal Transition Generates Proliferative Human Islet Precursor Cells, Science, Dec. 24, 2004, pp. 2261-2264, vol. 306, US.

Gibco, Solutions for Life Science Research and Drug Discovery, Catalogue Cell Culture Products, 2004-2005, pp. 1-4E, 281406 26 5 27.

Giltaire, et al., The CYP26 Inhibitor R115866 Potentiates the Effects of All-Trans Retinoic Acid on Cultured Human Epidermal Keratinocytes, British Journal of Dermatology, 2009, pp. 505-513, vol. 160.

Gittest, Developmental Biology of the Pancreas: A comprehensive Review, Developmental Biology, 2009, pp. 4-35, vol. 326, No. 1.

Gordon Weir, Do stem cells hold the key to creation of a cure for diabetes?, Diabetes Voice, 2008, pp. 29-31, Edition 53, No. 2.

Gosden, et al., Amniotic Fluid Cell Types and Culture, British Medical Bulletin, 1983, pp. 348-354, vol. 39, No. 4.

Graham, et al., Characteristics of a Human Cell Line Transformed by DNA from Human Adenovirus Type 5, Journal General Virology, 1977, pp. 59-72, vol. 36.

Gregg Duester, Retionoic Acid Synthesis and Signaling During Early Organogenesis, Cell, 2008, pp. 921-931, vol. 134.

Guo, et al., Stem Cells to Pancreatic B-Cells: New Sources for Diabetes Cell Therapy, Endocrine Reviews, May 2009, pp. 214-227, vol. 30, No. 3, The Endocrine Society.

Hadley, et al., Extracellular Matrix Regulates Sertoli Cell Differentiation, Testicular Cord Formation, and Germ Cell Development In Vitro, The Journal of Cell Biology, Oct. 1985, pp. 1511-1522, vol. 101, Rockefeller University Press.

Hainsworth, et al., Retinal Capillar Basement Membrane Thickening in a Porcine Model of Diabetes Mellitus, Comp Med, 2002, pp. 523-529, vol. 52.

Hamann, et al., Phenotypic and Functional Separation of Memory and and Effector Human CD8+ T Cells, Journal of Experimental Medicine, Mar. 11, 1997, pp. 1407-1418, vol. 186-9, Rockefeller University Press, US.

Harb, et al., The Rho-Rock-Myosin Signaling Axis Determines Cell-Cell Integrity of Self-Renewing Pluripotent Stem Cells, Plos One, 2008, Article e3001, vol. 3, Issue 8.

Harmon, et al., GDF11 Modulates NGN3+ Islet Progenitor Cell Number and Promotes B-Cell Differentiation in Pancreas Development, Development, 2004, pp. 6163-6174, vol. 131.

Haruta, et al., In Vitro and In Vivo Characterization of Pigment Epithelieal Cells Differentiated from Primate Embryonic Stem Cells, Investigative Ophthalmology & Visual Science, Mar. 2004, pp. 1020-1025, vol. 45, No. 3, Association for Research in Vision and Ophthalmology.

Hasegawa, et al., A Method for the Selection of Human Embryonic Stem Cell Sublines with High Replating Efficiency After Single-Cell Dissociation, Stem Cells, 2006, pp. 2649-2660, vol. 24.

Hashemi, et al., A Placebo Controlled, Dose-Ranging, Safety Study of Allogenic Mesenchymal Stem Cells Injected by Endomyocardial Delivery after an Acute Myocardial Infarction, European Heart Journal, Dec. 11, 2007, pp. 251-259, vol. 29.

Hay, et al., Highly Ethicient Differentiation of hESCs to Functional Hepatic Endoderm Requires ActivinA and Wnt3a Signaling, PNAS, 2008, pp. 12301-12306, vol. 105, No. 34.

Heinis, et al., HIF1a and Pancreatic Beta-Cell Development, The FASEB Journal, 2012, pp. 2734-2742, vol. 26.

Heinis, et al., Oxygen Tension Regulates Pancreatic Beta-Cell Differentiation Through Hypoxia-Inducible Factor 1x, Diabetes, 2010, pp. 662-669, vol. 59.

Heit, et al., Embryonic Stem Cells and Islet Replacement in Diabetes Mellitus, Pediatric Diabetes, 2004, pp. 5-15, vol. 5.

Held, et al., The Effect of Oxygen Tension on Colony Formation and Cell Proliferation of Amniotic Fluid Cells In-Vitro, Prenatal Diagnosis, 1984, pp. 171-180, vol. 4, No. 3.

Henderson, et al., Preimplantation Human Embryos and Embryonic Stem Cells Show Comparable Expression of Stage-Specific Embryonic Antigens, Stem Cells, 2002, pp. 329-337, vol. 20.

Heng, et al., Mechanical dissociation of human embryonic stem cell colonies by manual scraping after collagenase treatment is much more detrimental to cellular viability than is trypsinization with gentle pipetting, Biotechnol. Appl. Biochem., 2007, pp. 33-37, vol. 47, Portland Press Ltd., GB.

Heremans, et al., Recapitulation of Embryonic Neuroendocrine Differentiation in Adult Human Pancreatic Duct Cells Expressing Neurogenin 3, The Journal of Cell Biology, 2002, pp. 303-311, vol. 159.

Herrera, Adult-Insulin-and Glucagon-Producing Cells Differentiate from Two Independent Cell Lineages, Development, 2000, pp. 2317-2322, vol. 127, No. 11.

Herzenberg, et al., Fluorescence-activated Cell Sorting, Scientific American, 1976, pp. 108-117, vol. 234, Scientific American, US.

Hess, et al., Bone Marrow-Derived Stem Cells Initiate Pancreatic Regeneration, Nature Biotechnology, Jul. 2003, pp. 763-770, vol. 21, No. 7.

Ho, et al., Animal Cell Bioreactors, Animal Cell Bioreactors, 1991, 1-512, Hardcover, Butterworth-Heinemann.

Hoehn, et al., Morphological and Biochemical Heterogeneity of Amniotic Fluid Cells in Culture, Methods in Cell Biology, 1982, pp. 11-34, vol. 26, Academic Press, Inc.

Hoffman, et al., Characterization and Culture of Human Embryonic Stem Cells, Nature Biotechnology, 2005, pp. 699-708, vol. 23, No. 6.

Hori, et al., Growth inhibitors promote differentiation of insulin-producing tissue from embryonic stem cells, Proceedings of the National Academy of Sciences, Dec. 10, 2002, pp. 16105-16110, vol. 99-25, National Academy of Sciences.

(56) References Cited

OTHER PUBLICATIONS

Hosoya, et al., Induction of Differentiation of Undifferentiated Cells into Pancreatic Beta-Cells in Vertebrates, Int. J. Dev. Biol., 2012, pp. 313-323, vol. 56.

Hussain, et al., Stem-Cell Therapy for Diabetes Mellitus, Lancet, 2004, pp. 203-205, vol. 364.

Ianus, et al., In Vivo Derivation of Glucose-Competent Pancreatic Endocrine Cells from Bone Marrow Without Evidence of Cell Fusion, The Journal of Clinical Investigation, Mar. 2003, pp. 843-850, vol. 111, No. 6.

Inami, et al., Differentiation of Induced Pluripotent Stem Cells to Thymic Epithelial Cells by Phenotype, Immunology and Cell Biology, Jun. 24, 2010, pp. 1-8.

Inman, et al., SB-431542 is a Potent and Specific Inhibitor of Transforming Growth Factor-B Superfamily Type I Activing Receptor-Like Kinase (ALK) Receptors ALK4, ALK5, and ALK7, Molecular Pharmacology, 2002, pp. 65-74, vol. 62, No. 1.

Int' Anker, et al., Amniotic Fluid as a Novel Source of Mesenchymal Stem Cells for Therapeutic Transplantation, Blood, Aug. 15, 2003, pp. 1548-1549, vol. 102, No. 4.

Inzunza, et al., Derivation of Human Embryonic Stem Cell Lines in Serum Replacement Medium Using Postnatal Human Fibroblasts as Feeder Cells, Stem Cells, 2005, pp. 544-549, vol. 23, AlphaMed Press.

Itkin-Ansari, et al., Cell-Based Therapies for Diabetes: Progress Towards a Transplantable Human B Cell Line, Annals of the New York Academy of Sciences, 2003, pp. 138-147, vol. 1005, No. 1.

Jafary, et al., Differential effect of activin on mouse embryonic stem cell differentiation in insulin-secreting cells under nestin-positive selection and spontaneous differentiation protocols, Cell Biology International, 2008, pp. 278-286, vol. 32, Elsevier.

Jeon, et al., Endocrine Cell Clustering During Human Pancreas Development, J Histochem Cytochem, 2009, pp. 811-824, vol. 57, Issue 9.

Jiang, et al., Generation of Insulin-Producing Islet-Like Clusters from Human Embryonic Stem Cells, Stem Cells, 2007, pp. 1940-1953, vol. 25, Issue 8.

Jiang, et al., In Vitro Derivation of Functional Insulin-Producing Cells from Human Embryonic Stem Cells, Cell Research, 2007, pp. 333-344, vol. 17.

Johansson, et al., Temporal Control of Neurogenin3 Activity in Pancreas Progenitors Reveals Competence Windows for the Generation of Different Endocrine Cell Types, Developmental Cell, Mar. 2007, pp. 457-465, vol. 12.

Kahan, Pancreatic Precursors and Differentiated Islet Cell Types from Murine Embryonic Stem Cells, Diabetes, Aug. 2003, pp. 2016-2042, vol. 52.

Karvonen, et al., Incidene of Childhood Type 1 Diabetes Worldwide, Diabetes Care, 2000, pp. 1516-1526, vol. 23, No. 10.

Kelly, et al., Cell-Surface Markers for the Isolation of Pancreatic Cell Types Derived from Human Embryonic Stem Cells, Nature Biotechnology, 2011, pp. 750-756, vol. 29, Issue 8.

Kicic, et al, Differentiation of Marrow Stromal Cells into Photoreceptors in the Rat Eye, The Journal of Neuroscience, Aug. 27, 2003, pp. 7742-7749, vol. 23, Issue 21.

Kingsley, The TGF-B Superfamily: New Members, New Receptors, and New Genetic Tests of Function in Different Organisms, Genes & Development, 1994, pp. 133-146, vol. 8, Cold Spring Harbor Laboratory Press.

Kinkel, et al., Cyp26 Enzymes Function in Endoderm to Regulate Pancreatic Field Size, PNAS, May 12, 2009, pp. 1864-7869, vol. 106, No. 19.

Kleinman et al., Basement Membrane Complexes with Biological Activity, Biochemistry, 1986, pp. 312-318, vol. 25, American Chemical Society.

Klimanskaya, et al., Human Embryonic Stem Cells Derived without Feeder Cells, Lancet, May 2005, pp. 1636-1641, vol. 365, No. 9471.

Koblas, et al., Differentiation of CD133-Positive Pancreatic Cells Into Insulin-Producing Islet-Like Cell Clusters, Transplantation Proceedings, 2008, pp. 415-418, vol. 40.

Kohen, et al., Characterization of Matrigel Interfaces During Defined Human Embryonic Stem Cell Culture, Characterization of Matrigel Interfaces During Defined Human Embryonic Stem Cell Culture, Sep. 3, 2010, pp. 6979, vol. 4.

Koller, et al., Effects of Synergistic Cytokine Combinations, Low Oxygen, and Irradiated Stroma on the Expansion of Human Cord Blood Progenitors, Blood, Jul. 15, 1992, pp. 403-411, vol. 80, No. 2.

Konstantinova et al., 2007, EphA-Ephrin-A-Mediated Beta Cell Communication Regulates Insulin Secretion from Pancreatic Islets, Cell, Apr. 20, 2007, pp. 359-370, vol. 129.

Koyangi et al., Inhibitio nof the Rho/ROCK Pathway Reduces Apoptosis During Transplantatation of Embryonic Stem Cell-Derived Neural Precursors, Journal of Neurosciene Research, Sep. 7, 2007, pp. 270-280, vol. 86, Wiley-Liss, Inc.

Kozikowski, et al., New Amide-Bearing Benzolactam-Based Protein Kinase C Modulators Induce Enhanced Secretion of the Amyloid Precuros Protein Metabolite sAPPa, J. Med. Chem., 2003, pp. 364-373, vol. 46, No. 3.

Krapcho et al., Synthesis and Antineoplastic Evaluations of 5,8-Bis[(aminoalkyl)amino]-1-azaanthracene-9,10-diones, Journal of Medical Chemistry, 1985, pp. 1124-1126, vol. 28, American Chemical Society.

Krawetz, et al., Human Embryonic Stem Cells: Caught Between a ROCK Inhibitor and a Hard Place, BioEssays: News and Reviews in Molecular Cellular and Developmental Biology, 2009, pp. 336-343, vol. 31.

Kron, et al., Expression of Human Activin C Protein in Insect Larvae Infected with a Recombinant Baculovirus, Journal of Virological Methods, 1998, pp. 9-14, vol. 72.

Kroon, et al., Pancreatic Endoderm Derived from Human Embryonic Stem Cells Generates Glucose-Responsive Insulin-Secreting Cells in vivo, Nature Biotechnology, Apr. 2008, pp. 443-452, vol. 26, No. 4.

Krutzik, et al., Coordinate Analysis of Murine Immune Cell Surface Markers and Intracellular Phosphoproteins by Flow Cytometry, Journal of Immunology, May 30, 2005, pp. 2357-2365, vol. 175, American Association of Immunologists, Inc., US.

Ku et al., Committing Embryonic Stem Cells to Early Endocrine Pancreas In Vitro, Stem Cells, 2004, pp. 1205-1217, vol. 22, AlphaMed Press.

Kurihara-Bergstrom, et al., Characterization of the Yucatan Miniature Pig Skin and Small Intestine for Pharmaceutical Applications, Laboratory Animal Science, 1986, pp. 396-399, vol. 36, No. 4.

Lanza, et al., Characteristics and Characterization of Human Pluripotent Stem Cells, Stem Cell Anthology, 2010, pp. 141, 142, 144 and 146, 1st Edition.

Laplante, et al., RhoA/ROCK and Cdc42 Regulate Cell-Cell Contact and N-Cadherin Protein Level During Neurodetermination of P19 Embryonal Stem Cells, Journal of Neurobiology, 2004, pp. 289-307, vol. 60, No. 3.

Larsen, et al., Evaluation of B-Cell Mass and Function in the Gottingen Minipig, Diabetes, Obesity and Metabolism, 2007, pp. 170-179, vol. 9, Supplement 2, Blackwell Publishing Ltd.

Larsen, et al., Use of the Gootingen Minipig as a Model of Diabetes, with Special Focus on Type 1 Diabetes Research, ILAR Journal, 2004, pp. 303-313, vol. 45, No. 3.

Lavon et al., The Effect of Overexpression of Pdx1 and Foxa2 on the Differentiation of Human Embryonic Stem Cells into Pancreatic Cells, Stem Cells, 2006, pp. 1923-1930, vol. 24, Alpha Med Press, IL.

Le Blanc, et al., Mesenchymal Stem Cells Inhibit and Stimulate Mixed Lymphocyte Cultures and Mitogenic Responses Independently of the Major Histocompatibility Complex, Scandinavian Journal of Immunology, 2003, pp. 11-20, vol. 57, Blackwell Publishing Ltd.

Lee et al., Establishment and Maintenance of Human Embryonic Stem Cell Lines on Human Feeder Cells Derived from Uterine Endometrium under Serum-Free Condition, Biology of Reproduction, Aug. 18, 2004, pp. 42-49, vol. 72.

(56) References Cited

OTHER PUBLICATIONS

Lee, et al., Human B-cell Precursors Mature into Functional Insulin-Producing Cells in an Immunoisolation Device: Implications for Diabetes Cell Thereapies, Transplantation, Apr. 15, 2009, pp. 983-991, vol. 87, No. 7.

Lee, et al., PKC-Inhibitors Sustain Self-Renewal of Mouse Embryonic Stem Cells Under Hypoxia in Vitro, Experimental and Molecular Medicine, Apr. 2010, pp. 294-301, vol. 43, No. 4.

Lee, et al., Protein Kinase A- and C-Induced Insulin Release from Ca2+-Insensitive Pools, Cellular Signalling, 2003, pp. 529-537, vol. 15.

Lee, et al., Retionic Acid-Induced Human Secretin Gene Expression in Neuronal Cells is Mediated by Cyclin-Dependent Kinase 1, Annals of the New York Academy of Sciences, 2006, pp. 393-398, vol. 1070.

Leeper, et al., Stem Cell Therapy for Vascular Regeneration Adult, Embryonic, and Induced Pluripotent Stem Cells, Circulation, Aug. 3, 2010, pp. 517-526, vol. 122, No. 5.

Leon-Quinto, et al., In Vitro Directed Differentiation of Mouse Embryonic Stem Cells into Insulin-Producing Cells, Diabetologia, 2004, pp. 1442-1451, vol. 47, No. 8.

Levenstein et al., Basic Fibroblast Growth Factor Support of Human Embryonic Stem Cell Self-Renewal, Stem Cells, Nov. 10, 2005, pp. 568-574, vol. 24, AlphaMed Press.

Li, et al., Generation of Rat and Human Induced Pluripotent Stem Cells by Combining Genetic Reprogramming and Chemical Inhibitors, Cell Stem Cell, Jan. 9, 2009, pp. 16-19, vol. 4.

Li, et al., Pluripotency Can be Rapidly and Efficiently Induced in Human Amniotic Fluid-Derived Cells, Human Molecular Genetics, 2009, pp. 4340-4349, vol. 18, No. 22.

Lilja et al., Cyclin-dependent Kinase 5 Promotes Insulin Exocytosis, Journal of Biological Chemistry, Jul. 6, 2001, 34199-34205, vol. 36-7, JBC Papers in Press.

Liu, et al., A Novel Chemical-Defined Medium with bFGF and N2B27 Supplements Supports Undifferentiated Growth in Human Embryonic Stem Cells, Biochemical and Biophysical Research Communications, 2006, pp. 131-139, vol. 346.

Loh, et al., Genomic Approaches to Deconstruct Puripotency, Annu Rev Genomics Hum Genet, 2011, pp. 165-185, vol. 12.

Ludwig, et al., Defined Culture Media for Human Embryonic Stem Cells, Embryonic Stem Cells, 2007, pp. 1-16, Springer.

Lumelsky, et al., Differentiation of Embryonic Stem Cells to Insulin-Secreting Structures Similar to Pancreatic Islets, Science, 2001, pp. 1389-1394, vol. 292, HighWire Press.

Lund, et al., Cell Transplantation as a Treatment for Retinal Disease, Progress in Retinal and Eye Research, 2001, pp. 415-449, vol. 20, No. 4, Elsevier Science Ltd.

Lund, et al., Retinal Transplantation: Progress and Problems in Clinical Application, Journal of Leukocyte Biology, Aug. 2003, pp. 151-160, vol. 74.

Lyttle, et al., Transcription Factor Expression in the Developing Human Fetal Endocrine Pancreas, Diabetologica, 2008, pp. 1169-1180, vol. 51, Spring-Verlag.

MacFarlane, et al., Glucose Stimulates Translocation of the Homeodomain Transcription Factor PDX1 from the Cytoplasm to the Nucleus in Pancreatic B-Cells, The Journal of Biological Chemistry, 1999, pp. 1011-1016, vol. 274, No. 2.

Maherali, et al., Directly Reprogrammed Fibroblasts Show Global Epigenetic Remodeling and Widespread Tissue Contribution, Cell Stem Cell, Jul. 2007, pp. 55-70, vol. 1, Elsevier, Inc.

Mao, et al., The Reversal of Hyperglycaemia in Diabetic Mice Using PLGA Scaffolds Seeded with Islet-like Cells Derived from Human Embyonica Stem Cells, Biomaterials, 2009, pp. 1706-1714, vol. 30.

Marshall, et al., Early Micro-and Macro-Angiopathy in the Streptozotocin, Research in Experimental Medicine, 1980, pp. 145-158, vol. 177, Springer-Verlag.

Marshall, et al., Isolation and Maintenance of Primate Embryonic Stem Cells, Methods in Molecular Biology, 2001, pp. 11-18, vol. 158.

Martin, et al., Bioreactors for Tissue Mass Culture: Design, Characterization, and Recent Advances, Biomaterials, Jul. 14, 2005, pp. 7481-7503, vol. 26.

Marzo, et al., Pancreatic Islets from Cyclin-Dependent Kinase 4/R24C (Cdk4) Knockin Mice have Significantly Increased Beta Cell Mass and are Physiologically Functional, Indicating that Cdk4 is a Potential Target for Pancreatic . . . , Diabetologia, 2004, pp. 686-694, vol. 47.

Mathis, et al., B-Cell Death During Progression to Diabetes, Nature, 2001, pp. 792-798, vol. 414.

Matveyenko, et al., Inconsistent Formation and Nonfunction of Insulin-Positive Cells from Pancreatic Endoderm Derived from Human Embyonic Stem Cells in Athymic Nude Rats, American Journal of Physiol Endocrinol Metab, 2010, pp. E713-E720, vol. 299.

McKiernan, et al., Directed Differentiation of Mouse Embryonic Stem Cells into Pancreatic-Like or Neuronal-and Glial-Like Phenotypes, Tissue Engineering, 2007, pp. 2419-2430, vol. 13, No. 10.

McLin, et al., Repression of WNT/(szligbeta)-6atenin Signaling in the Anterior Endoderm is Essential for Liver and Pancreas Development, Development, 2007, pp. 2207-2217, vol. 134, Issue 12.

Meijer, et al., Pharmacological Inhibitors of Glycogen Synthase Kinase 3, Trends in Pharmacological Sciences, Sep. 2004, pp. 471-480, vol. 25, No. 9.

Micallef et al., Retinoic Acid Induces Pdx1-Positive Endoderm in Differentiating Mouse Embryonic Stem Cells, Diabetes, Feb. 2005, pp. 301-305, vol. 54, American Diabetes Association.

Miller, et al., The Pig as a Model for Human Nutrition, Annual Review of Nutrition, 1987, pp. 361-382, vol. 7, Annual Reviews Inc.

Milunsky, et al., Genetic Disorders and the Fetus: Diagnosis Prevention and Treatment, Pediatric and Developmental Pathology, 2011, pp. 84, vol. 14, Society for Pediatric Pathology.

Minami, et al., A Small Molecule that Promotes Cardiac Differentiation of Human Pluripotent Stem Cells Under Defined, Cytokine- and Xeno-free Conditions, Cell Reports, 2012, pp. 1448-1460, vol. 2, No. 5.

Mitalipova, et al., Preserving the Genetic Integrity of Human Embyonic Stem Cells, Nature Biotechnology, 2005, pp. 19-20, vol. 23, No. 1.

Mitsui, et al., The Homeoprotein Nanog is Required for Maintenance of Pluripotency in Mouse Epiblast and ES Cells, Cell, May 30, 2003, pp. 631-642, vol. 113, Cell Press.

Miyamoto et al., Human Placenta Feeder Layers Support Undifferentiated Growth of Primate Embryonic Stem ells, Stem Cells, 2004, pp. 433-440, vol. 22, AlphaMed Press.

Miyazaki et al., Regulated Expression of pdx-1 Promotes In Vitro Differentiation of Insulin-Producing Cells From Embryonic Stem Cells, Diabetes, Apr. 2004, pp. 1030-1037, vol. 53, American Diabetes Association.

Moore, et al., The Corneal Epithelial Stem Cell, DNA and Cell Biology, 2002, pp. 443-451, vol. 21, No. 5/6.

Moran, et al., Bidirectional-Barbed Sutured Knotless Running Anastomosis v Classic van Velthoven in a Model System, Journal of Endourology, 2007, pp. 1175-1177, vol. 21, No. 10.

Morrison, et al., Culture in Reduced Levels of Oxygen Promotes Clonogenic Sympathoadrenal Differentiation by Isolated Neural Crest Stem Cells, Journal of Neuroscience, Oct. 1, 2000, pp. 7370-7376, vol. 20, No. 19.

Movassat, et al., Keratinocyte Growth Factor and Beta-Cell Differentiation in Human Fetal Pancreatic Endocrine Precursor Cells, Diabetologia, 2003, pp. 822-829, vol. 46.

Muchamuel, et al., Preclinical Pharmacology and in Vitro Characterization of PR-047, An Oral Inhibitor of the 20s Proteasome, Blood, Nov. 16, 2008, p. 1257, vol. 112, No. 11.

Munoz et al., Conventional Pluripotency Markers are Unspecific for Bovine Embryonic-Derived Cell-Lines, Theriogenology, 2008, pp. 1159-1164, vol. 69.

Murtha, et al., Evaluation of a Novel Technique for Wound Closure Using a Barbed Suture, Cosmetic, Aug. 2, 2005, pp. 1769-1780, vol. 117, No. 6.

Nakagawa, et al., Generation of Induced Pluripotent Stem Cells without Myc from Mouse and Human Fibroblasts, Generation of

(56) References Cited

OTHER PUBLICATIONS

Induced Pluripotent Stem Cells without Myc from Mouse and Human Fibroblasts, Jan. 2008, pp. 101-106, vol. 26, No. 1.
Nakamura, et al., Ocular Surface Reconstruction Using Cultivated Mucosal Epithelial Stem Cells, Cornea, Oct. 2003, pp. S75-S80, vol. 22, Supplement 1.
Nelson, et al., The Transcription Factors Nkx6.1 and Nkx6.2 Possess Equivalent Activities in Promoting Beta-Cell Fate Specification in Pdx1+ Pancreatic Progenitor Cells, Development, 2007, pp. 2491-2500, vol. 134.
Nicholas et al, A Method for Single-Cell Sorting and Expansion of Genetically modified Human Embryonic Stem Cells, Stem Cells and Development, 2007, pp. 109-117, vol. 16, Mary Ann Liebert, Inc.
Nie, et al., Scalable Passaging of Adherent Human Pluripotent Stem Cells, PLOS One, 2014, pp. 1-9, vol. 9, Issue 1.
Nishimura, et al., Expression of MafA in Pancreatic Progenitors is Detrimental for Pancreatic Development, Developmental Biology, 2009, pp. 108-120, vol. 333.
Nostro, et al., Generation of Beta Cells from Human Pluripotent Stem Cells: Potential for Regenerative Medicine, Seminars in Cell & Developmental Biology, 2012, pp. 701-710, vol. 23.
Nostro, et al., Stage-Specific Signaling Through TGF Family Members and WNT Regulates Patterning and Pancreatic Specification of Human Pluripotent Stem Cells, Development, 2011, pp. 861-871, vol. 138, Issue 5.
Odom, et al., Control of Pancreas and Liver Gene Expression by HNF Transcription Factors, Science, 2004, pp. 1378-1381, vol. 303, No. 5662.
Okita, et al., Generation of Germline-Competent Induced Pluripotent Stem Cells, Nature, Jul. 19, 2007, pp. 313-317, vol. 448.
Orlowski, et al., Safety and Antitumor Efficacy of the Proteasome Inhibitor Carfilzomib (PR-171) Dosed for Five Consecutive Days in Hematologic Malignancies: Phase 1 Results, Blood, 2007, Part 1, vol. 110, No. 11.
Osborne, et al., Some Current Ideas on the Pathogenesis and the Role of Neuroprotection in Glaucomatous Optic Neuropathy, European Journal of Ophthalmology, 2003, S19-S26, vol. 13, Supplement 3, Wichtig Editore.
Ostrom, et al., Retinoic Acid Promotes the Generation of Pancreatic Endocrine Progenitor Cells and Their Further Differentiation into B-Cells, PLOS One, Jul. 30, 2008, e2841, pp. 1-7, vol. 3, No. 7.
Ouziel-Yahalom, et al., Expansion and Redifferentiation of Adult Human Pancreatic islet Cells, Biochemical and Biophysical Research Communications, 2006, pp. 291-298, vol. 341.
Paling, et al., Regulation of Embryonic Stem Cell, Self-Renewal by Phosphoinositide 3-kinase-dependent Signaling, Journal of Biological Chemistry, 2004, pp. 48063-48070, vol. 279, No. 46.
Panchision, et al., Optimized Flow Cytometric Analysis of Central Nervous System Tissue Reveals Novel Functional Relationships Among Cells Expressing CD133, CD15, and CD24, Stem Cells, 2007, pp. 1560-1570, vol. 25.
Panepinto, et al., The Yucatan Miniature Pig: Characterization and Utilization in Biomedical Research, Laboratory Animal Science, Aug. 1986, pp. 344-347, vol. 36, No. 4, American Association for Laboratory Animal Science.
Pangas, et al., Production and Purification of Recombinant Human Inhibin and Activin, Journal of Endocrinology, 2002, pp. 199-210, vol. 172.
Pardo, et al., Corning CellBIND Surface: An Improved Surface for Enhanced Cell Attachment, Corning Technical Report, 2005, 8 page report.
Paris, et al, Equine Embryos and Embryonic Stem Cells: Defining Reliable Markers of Pluripotency, Theriogeneology, 2010, pp. 516-524, vol. 74.
Park, et al., Effects of Activin A on Pancreatic Ductal Cells in Streptozotocin-Inducted Diabetic Rats, Experimental Transplantation, 2007, pp. 925-930, vol. 83.
Peerani, et al., Niche-Mediated Control of Human Embryonic Stem Cell Self-Renewal and Differentiation, The EMBO Journal, 2007, pp. 4744-4755, vol. 26.
Perrier, et al., Derivation of Midbrain Dopamine Neurons from Human Embryonic Stem Cells, PNAS, Aug. 24, 2004, pp. 12543-12548, vol. 101, No. 34.
Phillips, et al., Directed Differentiation of Human Embryonic Stem Cells into the Pancreatic Endocrine Lineage, Stem Cells and Development, 2007, pp. 561-578, vol. 16, No. 4.
Pouton, et al., Embryonic Stem Cells as a Source of Models for Drug Discovery, Nature Reviews Drug Discovery, Aug. 2007, pp. 1474-1776, vol. 6, No. 8.
Prichard, et al., Adult Adipose Derived Stem Cell Attachment to Biomaterials, Biomaterials, 2006, pp. 936-946, vol. 28, No. 6.
Prusa, et al., Oct-4-Expressing Cells in Human Amniotic Fluid: a New Source for Stem Cell Research?, Human Reproduction, 2003, pp. 1489-1493, vol. 18, No. 7.
Ptasznik, et al., Phosphatidylinositol 3-Kinase Is a Negative Regulator of Cellular Differentiation, The Journal of Cell Biology, 1997, pp. 1127-1136, vol. 137, No. 5.
R&D Systems, Embryonic & Induced Pluripotent Stem Cell Transcription Factors, Embryonic & Induced Pluripotent Stem Cell Transcription Factors, 2013, http://www.mdsystems.com/molecule_group.aspx?r=1&g-3041, 2 page web printout.
R&D Systems, Pancreatic Endoderm, Pancreatic Endoderm, Jun. 24, 2013, http://www.rndsystems.com/molecule_group.aspx?g=801 &r, 1 page web printout.
Rajagopal, et al., Insulin Staining of ES Cell Progeny from Insulin Uptake, Science, Jan. 17, 2003, pp. 363, vol. 299.
Rajala, et al., Testing of Nine Different Xeno-free Culture Media for Human Embryonic Stem Cell Cultures, Human Reproduction, Jan. 24, 2007, pp. 1231-1238, vol. 22, No. 5.
Ramiya, et al., Reversal of Insulin-Dependent Diabetes Using Islets Generated in vitro from Pancreatic Stem Cells, Nature Medicine, 2000, pp. 278-281, vol. 6.
Rao, Conserved and Divergent Paths that Regulate Self-Renewal in Mouse and Human Embryonic Stem Cells, Developmental Biology, Aug. 10, 2004, pp. 269-286, vol. 275, Elsevier, Inc.
Rebbapragada, et al., Myostatin Signals Through a Transforming Growth Factor B-Like Signaling Pathway to Bock Adipogenesis, Molecular and Cellular Biology, 2003, pp. 7230-7242, vol. 23, No. 20.
Rebollar, et al., Proliferation of Aligned Mammalian Cells on Laser-Nanostructured Polystyrene, Biomaterials, 2008, pp. 1796-1806, vol. 29.
Reisner, Growing Organs for Transplantation form Embryonic Precursor Tissues, Immunol. Res., 2007, pp. 261-273, vol. 38.
Reubinoff et al., Embryonic stem cell lines from human blastocysts: somatic differentiation in vitro, Nature Biotech, Apr. 18, 2000, 399-404, 18, Nature America Inc.
Rezania, E Al., Maturation of Human Embryonic Stem Cell-Derived Pancreatic Progenitors Into Functional Islets Capable of Treating Pre-Existing Diabetes in Mice, Diabetes, 2012, pp. 2016-2029, vol. 61.
Rezania, et al., Enrichment of Human Embryonic Stem Cell-Derived NKX6.1—Expressing Pancreatic Progenitor Cells Accelerates the Maturation of Insulin-Secreting Cells In Vivo, Stem Cells, 2013, pp. 2432-2442, vol. 31.
Rezania, et al., Reversal of Diabetes with Insulin-Producing Cells Derived in vitro from Human Pluripotent Stem Cells, Nature Biotechnology, 2014, pp. 1121-1133, vol. 32, No. 11.
Rezania, Production of Functional Glucagon-Secreting-Cells from Human Embryonic Stem Cells, Diabetes, 2011, pp. 239-247, vol. 60, Issue 1.
Richards et al., Comparative Evaluation of Various Human Feeders for Prolonged Undifferentiated Growth of Human Embryonic Stem Cells, Stem Cells, 2003, 546-556, 21, AlphaMed Publlishing.
Richards, et al., Development of Defined Media for the Serum-Free Expansion of Primary Keratinocytes and Human Embryonic Stem Cells, Tissue Engineering, 2008, pp. 221-232, vol. 14, No. 3.
Richardson, et al., Bortezomid (PS-341): A Novel, First-in-Class Proteasome Inhibitor for the Treatement of Multiple Myeloma and Other Cancers, Cancer Control, 2003, pp. 361-369, vol. 10, No. 5.

(56) References Cited

OTHER PUBLICATIONS

Ricordi et al., Automated Method for Isolation of Human Pancreatic Islets, Diabetes, Apr. 1988, pp. 413-420, vol. 37, American Diabetes Association.
Ross, et al., Cytochrome P450s in the Regulation of Cellular Retinoic Acid Metabolism, Annu. Rev. Nutr., 2011, pp. 65-87, vol. 31.
Rowley, et al., Meeting Lot-Size Challenges of Manufacturing Adherent Cells for Therapy, Cell Therapies Manufacturing, 2012, pp. 16-22, vol. 10, No. 3.
Ryan, et al., Clinical Outcomes and Insulin Secretion After Islet Transplantation with the Edmonton Protocol, Diabetes, Apr. 2001, pp. 710-719, vol. 50.
Sakaguchi, et al., Integration of Adultmesenchymal Stem Cells in the CNS, Society for Neuroscience Abstract Viewer and Itineray Planner, 2002, Program 237.18.
Sander, et al., Homeobox Gene Nkk6.1 Lies Downstream of Nkx22 in the Major Pathway of Betta-Cell Formation in the Pancreats, Development, 2000, pp. 5533-5540, vol. 127.
Sato, et al., Maintenance of Pluripotency in Human and Mouse Embryonic Stem Cells Through Activation of Wnt Signaling by a Pharmacological GSK-3-specific Inhibitor, Nature Medicine, Jan. 2004, pp. 55-63, vol. 10, No. 1.
Sato, et al., Manipulation of Self-Renewal in Human Embryonic Stem Cells Through a Novel Pharmacological GSK-3 Inhibitor, Methods in Molecular Biology, 2006, pp. 115-128, vol. 331.
Savino et al., Generation of Interleukin-6 Receptor Antagonists by Molecular-Modeling Guided Mutagenesis of Residues Important for gp130 Activation, EMBO Journal, 1994, pp. 1357-1367, vol. 13-6, IT.
Schisler, et al., The Nkx6.1 Homeodomain Transcription Factor Suppresses Glucagon Expression and Regulates Glucose-Stimulated Insulin Secretion in Islet Beta Cells, Proceedings of the National Academy of Sciences of the USA, 2005, pp. 7297-7302, vol. 102, No. 20.
Schnier, et al., G1 Arrest and Down-Regulation of Cyclin E/cyclin-dependent Kinase 2 by the Protein Kinase Inhibitor Staurosporine are Dependent on the Retinoblastoma Protein in the Bladder Carcinoma Cell Line 5637, Proceedings of the National Academy of Sciences, 1996, pp. 5941-5946, vol. 93.
Schraermeyer, et al., Subretinally Transplanted Embryonic Stem Cells Rescue Photoreceptor Cells From Degeneration in the RCS Rats, Cell Transplantation, 2001, pp. 673-680, vol. 10.
Schroeder, et al., Differentiation of Mouse Embryonic Stem Cells to Insulin-Producing Cells, Nature Protocols, 2005, pp. 495-507, vol. 1, No. 2.
Schuldiner, et al., Induced Neuronal Differentiation of Human Embryonic Stem Cells, Brain Research, 2001, pp. 201-205, vol. 913.
Schulz, et al., A Scalable System for Production of Functional Pancreatic Progenitors from Human Embryonic Stem Cells, PLOS One, 2012, pp. 1-17, vol. 7, Issue 5.
Scullica, et al., Diagnosis and Classification of Macular Degenerations: an Approach Based on Retinal Function Testing, Documenta Ophthalmologica, 2001, pp. 237-250, vol. 102.
Seaberg et al., Cfonal identification of multipotent precursors from adult~ mouse pancreas that generate neural and pancreatic lineages, Nature Biotechnology, Sep. 2004, pp. 1115-1124, vol. 22, No. 9, Nature Publishing Group.
Segev, et al., Differentiation of Human Embryonic Stem Cells into Insulin-Producing Clusters, Stem Cells, Jan. 1, 2004, pp. 265-274.
Serafimidis, et al., Novel Effectors of Directed and Ngn3-Mediated Differentiation of Mouse Embryonic Stem Cells into Endocrine Pancreas Progenitors, Stem Cells, 2008, pp. 3-16, vol. 26.
Shackleton, et al., Generation of a Functional Mammary Gland from a Single Stem Cell, Nature, Jan. 5, 2006, pp. 84-88, vol. 439.
Shamblott et al., Derivation of pluripotent stem cells from cultured human primordial germ cells, Developmental Biology, Nov. 1998, 13726-13731, 95, National Academy of Sciences.
Shapiro, et al., Islet Transplantation in Seven Patients with Type 1 Diabetes Mellitus Using a Glucocorticoid-Free Immunosuppressive Regimen, The New England Journal of Medicine, Jul. 27, 2000, pp. 230-238, vol. 343, No. 1, The Massachusetts Medical Society.
Shen, et al., The Effects of Surface Chemistry and Absorbed Proteins on Monocyte/Macrophage Adhesion to Chemically Modified Polystyrene Surfaces, Journal of Biomedical Matter Research, 2001, pp. 336-345, vol. 57.
Sherwood, et al., Transcriptional Dynamics of Endodermal Organ Formation, Developmental Dynamics, 2009, pp. 29-42, vol. 238, Issue 1.
Shi et al., Inducing Embryonic Stem Cells to Differentiate into Pancreatic β Cells by a Novel Three-Step Approach with Activin A and All-Trans Retinoic Acid, Stem Cells, 2005, pp. 656-662, vol. 23, AlphaMed Press.
Shim, et al., Directed Differentiation of Human Embryonic Stem Cells Towards a Pancreatic Cell Fate, Diabetologia, 2007, pp. 1228-1238, vol. 50.
Shindler et al., A synthetic nanofibrillar matrix promotes in vivo-like organization and morphogenesis for cells in culture, Biomaterials, Apr. 18, 2005, pp. 5624-5631, vol. 26, Elsevier.
Shiraki et al., TGF-B Signaling Potentiates Differentiation of Embryonic Stem Cells to Pdx-1 Expressing Endodermal Cells, Genes to Cells, 2005, pp. 503-516, vol. 10, Blackwell Publishing Limited.
Shiraki, et al., Guided Differentiation of Embryonic Stem Cells into Pdx1-Expressing Regional-Specific Definitive Endoderm, Stem Cells, 2008, pp. 874-885, vol. 26.
Sidhu et al., Derivation of Three Clones from Human Embryonic Stem Cell Lines by FACS Sorting and Their Characterization, Stem Cells and Development, 2006, pp. 61-69, vol. 15, Mary Ann Liebert, Inc.
Simandi, et al., Retinoid Signaling is a Context-Dependent Regulator of Embryonic Stem Cells, Embryonic Stem Cells—Differentiation and Pluripotent Alternatives, 2011, pp. 55-79, Chapter 3.
Simons, et al., Assembly of Protein Tertiary Structures from Fragments with Similar Local Sequences Using Simulated Annealing and Bayesian Scoring Functions, Journal of Molecular Biology, 1997, pp. 209-225, vol. 268.
Simons, et al., Improved Recognition of Native-Like Protein Structures Using a Combination of Sequence-Dependent and Sequence-Independent Features of Proteins, Proteins: Structure, Function, and Genetics, 1999, pp. 82-95, vol. 34, Wiley-Liss, Inc.
Skoudy et al., Transforming growth factor (TGF)β, fibroblast growth factor (FGF) and retinoid signalling pathways promote pancreatic exocrine gene expression in mouse embryonic stem cells, Journal of Biochemistry, 2004, pp. 749-756, vol. 379, Biochemical Society, GB.
Smith et al., Anti-Interleukin-6 Monoclnal Antibody Induces Regression of Human Prostate Cancer Xenografts in Nude Mice, The Prostate, Mar. 2, 2001, pp. 47-53, vol. 48, Wiley-Liss, Inc.
Sneddon, et al., Self-Renewal of Embryonic-Stem-Cell-Derived Progenitors by Organ-Matched Mesenchyme, Nature, Nov. 29, 2012, pp. 765-770, vol. 491.
Soria, et al., From Stem Cells to Beta Cells: New Strategies in Cell Therapy of Diabetes Mellitus, Diabetologia, 2001, pp. 407-415, vol. 44.
Soria, et al., Insulin-Secreting Cells Derived From Embryonic Stem Cells Normalize Glycemia in Streptozotocin-Induced Diabetic Mice, Diabetes, 2000, pp. 157-162, vol. 49, No. 2.
Spence, et al., Translation Embryology: Using Embryonic Principles to Generate Pancreatic Endocrine Cells from Embryonic Stem Cells, Developmental Dynamics, 2007, pp. 3218-3227, vol. 236.
Stacpoole, et al., Efficient Derivation of Neural Precursor Cells, Spinal Motor Neurons and Midbr, Nat Protoc, 2012, pp. 1-26, vol. 6, Issue 8.
Stadtfeld, et al., Defining Molecular Cornerstones During Fibroblast to iPS Cell Reprogramming in Mouse, Cell Stem Cell, Mar. 2008, pp. 230-240, vol. 2.
Stafford, et al., Retinoic Acid Signaling is Required for a Critical Early Step in Zebrafish Pancreatic Development, Current Biology, 2002, pp. 1215-1220, vol. 12, Issue 14.

(56) References Cited

OTHER PUBLICATIONS

Stafford, et al., Retinoids Signal Directly to Zebrafish Endoderm to Specify Insuilin-Expressing B-cells, Development, 2005, pp. 949-956, vol. 133.
Stoffel, et al., Navigating the Pathway from Embryonic Stem Cells to Beta Cells, Seminars in Cell & Developmental Biology, 2004, pp. 327-336, vol. 15.
Stojkovic et al., An Autogeneic Feeder Cell System That Efficiently Supports Growth of Undifferentiated Human Embryonic Stem Cells, Stem Cells, 2005, pp. 306-314, vol. 23, AlphaMed Press.
Sugiyama, et al., Conserved Markers of Fetal Pancreatic Epithelium Permit Prospective Isolation of Islet Progenitor Cells by FACS, PNAS, Jan. 2, 2007, pp. 175-180, vol. 104, No. 1.
Sugiyama, et al., Fluorescence-Activated Cell Sorting Purification of Pancreatic Progenitor Cells, Diabetes, Obesity and Metabolism, 2008, pp. 179-185, vol. 10, Supplement 4.
Suh, et al., Characterization of His-X3-His Sites in a-Helices of Synthetic Metal-Binding Bovine Somatotropin, Protein Engineering, 1991, pp. 301-305, vol. 4, No. 3.
Sulzbacher, et al., Activin A-Induced Differentiation of Embryonic Stem Cells into Endoderm and Pancreatic Progenitors—The Influence of Differentiation Factors and Culture Conditions, Stem Cell Rev, 2009, pp. 159-173, vol. 5.
Sun, et al., Feeder-Free Derivation of Induced Pluripotent Stem Cells from Adult Human Adipose Stem Cells, Proceedings and the National Academy of Sciences, 2009, pp. 15720-15725, vol. 106, No. 37.
Suzuken, Differentiation of Multifunctional Stem Cells Using Human Feeder Cells, Research Papers of the Suzuken Memorial Foundation, 2007, pp. 193-197, vol. 24, JP.
Swindle, et al., Swine in Biomedical Research: Management and Models, ILAR News, 1994, pp. 1-5, vol. 36, No. 1.
Takahashi, et al., Homogenous Seeding of Mesenchymal Stem Cells into Nonwoven Fabric for Tissue Engineering, Tissue Engineering, 2003, pp. 931-938, vol. 9, No. 5.
Takahashi, et al., Induction of Pluripotent Stem Cells from Adult Human Fibroblasts by Defined Factors, Cell, 2007, pp. 861-872, vol. 131.
Takehara, et al., Rho-Associate Kinase Inhibitor Y-27632 Promotes Survival of Cynomolgus Monkey Embryonic Stem Cells, Molecular Human Reproduction, 2008, pp. 627-634, vol. 14, No. 11.
Tang, et al., Reprogramming Liver-Stem WB Cells into Functional Insulin-Producing Cells by Persistent Expression of Pdx1-and Pdx1-VP16 Mediated by Lentiviral Vectors, Laboratory Investigation, 2006, pp. 83-93, vol. 86.
Tannock, et al., Chemotherapy with Mitoxantrone Plus Prednisone or Prednisone Alone for Symptomatic Hormone-Resistant Prostate Cancer: A Canadian Randomized Trial With Palliative End Points, Journal of Clinical Oncology, 1996, pp. 1756-1764, vol. 14-6, American Society of Clinical Oncology, US.
Teare, et al., Cellular Attachment to Ultraviolet Ozone Modified Polystyrene Surfaces, Langmuir, 2000, pp. 2818-2824, vol. 16.
Thermofisher Scientific, B-27 Serum-Free Supplement (50x) Liquid, Technical Resources, 2016, URL:https://www.thermofisher.com/nl/en/home/technical-resources/media-formulation.250.html, retrieved from the internet.
Thomson et al., Primate Embryonic Stem Cells, Currenl Topics in Developmental Biology, 1998, pp. 133-154, vol. 38, Academic Press, US.
Tomita, et al., Bone Marrow-Derived Stem Cells Can Differentiate into Retinal Cells in Injured Rat Retina, Stem Cells, 2002, pp. 279-283, vol. 20.
Totonchi, et al., Feeder-and Serum-Free Establishment and Expansion of Human Induced Pluripotent Stem Cells, Int. J. Dev. Biol., 2010, pp. 877-886, vol. 54.
Tsai, et al., Isolation of Human Multipotent Mesenchymal Stem Cells from Second-Trimester Amniotic Fluid Using a Novel Two-Stage Culture Protocol, Human Reproduction, Apr. 22, 2004, pp. 1450-1456, vol. 19, No. 6.
Tsuchida, et al., Activin Isoforms Signal Through Type I Receptor Serine/Threonin Kinase ALK7, Molecular and Cellular Endocrinology, 2004, pp. 59-65, vol. 22.
Tulachan et al., TGF-β isoform signaling regulates secondary transition and mesenchymal-induced endocrine development in the embryonic mouse pancreas, Developmental Biology, 2007, pp. 508-521, vol. 305, Elsevier.
Ubeda et al., Inhibition of Cyclin-dependent Kinase 5 Activity Protects Pancreatic Beta Cells from Glucotoxicity, Journal of Biological Chemistry, Aug. 3, 2006, pp. 28858-28864, vol. 39, JBC Papers in Press.
Uludag, et al., Technology of Mammalian Cell Encapsulation, Advanced Drug Delivery Reviews, 2000, pp. 29-64, vol. 42.
Ungrin, et al., Reproducible, Ultra High-Throughput Formation of Multicellular Organization from Single Cell Suspension-Derived Human Embryonic Stem Cell Aggregates, Plos ONE, 2008, e1565, pp. 1-12, vol. 3, Issue 2.
Unknown, MeSH Descriptor Data, National Library of Medicine—Medical Subject Headings, Feb. 26, 1992.
Unknown, Preserve the Stability of Your Stem Cells, Stem Cells, 2006, Internet Citation.
Vacanti, et al., Selective Cell Transplantation Using Bioabsorbable Artificial Polymers as Matrices, Journal of Pediactric Surgery, Jan. 1988, pp. 3-9, vol. 23-1.
Valet, et al., Pretherapeutic Identification of High-Risk Acute Myeloid Leukemia (AML) Patients from . . . , Clinical Cytometry, Feb. 17, 2003, pp. 4-10, vol. 53B, Wiley-Liss, Inc., US.
Vallier, et al., Activin/Nodal and FGF Pathways Cooperate to Maintain Pluripotency of Human Embryonic Stem Cells, Journal of Cell Sciences, 2005, pp. 4495-4509, vol. 118.
Van der Greef et al., Rescuing drug discovery: in vivo systems pathology and systems pharmacology, Nature, Dec. 1, 2005, pp. 961-967, vol. 4-1, Nature Reviews, US.
Van Der Windt, et al., The Chioce of Anatomical Site for Islet Transplantation, Cell Transplantation, 2008, pp. 1005-1014, vol. 17.
Van Kooten, et al., Plasma-Treated Polystyrene Surfaces: Model Surfaces for Studying Cell-Biomaterial Interactions, Biomaterials, 2004, pp. 1735-1747, vol. 25.
Van Wachem, et al., Method for the Fast Application of an Evenly Distributed Cell Layer on Porous Vascular Grafts, Biomaterials, 1990, pp. 602-606, vol. 11.
Vanderford et al., Multiple kinases regulate mafA expression in the pancreatic beta cell line MIN6, Biochemistry and Biophysics, 2008, pp. 138-142, vol. 480, Elsevier.
Verfaillie, et al., Stem Cells: Hype and Reality, Hematology, 2002, pp. 369-391.
Vieira, et al., Modulation of Neuronal Stem Cell Differentiation by Hypoxia and Reactive Oxygen Species, Progress in Neurobiology, 2011, pp. 444-455, vol. 93.
Vodicka, et al., The Miniature Pig as an Animal Model in Biomedical Research, Annals New York Academy of Sciences, 2005, pp. 161-171, vol. 1049.
Vunjak-Novakovic, et al., Dynamic Cell Seeding of Polymer Scaffolds for Cartilage Tissue Engineering, Biotechnology Program, 1998, pp. 193-202, vol. 14, Issue 2.
Wachs, et al., High Efficacy of Clonal Growth and Expansion of Adult Neural Stem Cells, Laboratory Investigation, 2003, pp. 949-962, vol. 83, No. 7.
Wang et al., Derivation and Growing Human Embryonic Stem Cells on Feeders Derived from Themselves, Stem Cells, 2005, 1221-1227, 23, AlphaMed Press.
Wang et al., Relationship of Chemical Structures of Anthraquinones with their Effects on the Suppression of Immune Responses, International Journal of Immunopharmacology, 1987, pp. 733-739, vol. 9-6, International Society for Immunopharmacology, GB.
Wang, et al., Noggin and bFGF Cooperate to Maintain the Pluripotency of Human Embryonic Stem Cells in the Absence of Feeder Layers, Biochemical and Biophysical Research Communications, 2005, pp. 934-942, vol. 33, No. 3.
Wang, et al., Three-Dimensional Differentiation of Embryonic Stem Cells into islet-Like Insulin-Producing Clusters, Tissue Engineering: Part A, 2009, pp. 1941-1952, vol. 15, No. 8.

(56) References Cited

OTHER PUBLICATIONS

Want, et al., Large-Scale Expansion and Exploitation of Pluripotent Stem Cells for Regenerative Medicine Purposes: beyond the T Flask, Loughborough University Institutional Repository, 2012, pp. 71-84, vol. 7, Issue 1.

Wei et al., Cdk5-dependent regulation of glucose-stimulated insulin secretion, Nature Medicine, Sep. 11, 2005, pp. 1104-1108, vol. 11-10, Nature Publishing Group.

Wei, et al., Human Amnion-Isolated Cells Normalize Blood Glucose in Strepozotocin Induced Diabetic Mice, Cell Transplantation, 2003, pp. 545-552, vol. 12, No. 5.

Wells, et al., Early Mouse Endoderm is Patterned by Soluble Factors from Adjacent Germ Layers, Development, 2000, pp. 1563-1572, vol. 127, Issue 8.

Wernig, et al., c-Myc is Dispensable for Direct Reprogramming of Mouse Fibroblasts, Cell Stem Cell, Jan. 2008, pp. 10-12, vol. 2.

White, et al., Complex Regulation of cyp26a1 Creates a Robust Retinoic Acid Gradient in the Zebrafish Embryo, PLOS Biology, 2007, pp. 2522-2533, vol. 5, Issue 11.

Wiles et al., Embryonic Stem Cell Development in a Chemically Defined Medium, Experimental Cell Research, 1999, pp. 241-248, vol. 247, Academic Press.

Wilson, et al., The HMG Box Transcription Factor Sox4 Contributes to the Development of the Endcrine Pancreas, Diabetes, 2005, pp. 3402-4309, vol. 54, Issue 12.

Wong, et al., Directed Differentiation of Human Pluripotent Stem Cells into Mature Airway Epithelia Expressing Functional CFTR Protein, Nature Biotechnology, 2012, pp. 876-884, vol. 30, No. 9. XP002553616_1989, RecName: Full=Inhibin beta B Chain; AltName: Full=Activin beta-B chain; Flags; Precursor, Database UniProt [Online], Jul. 1, 1989, Database Accession No. P09529, EBI Accession No. Uniprot: P09529.

Xu et al., Immortalized Fibroblast-Like Cells Derived from Human Embryonic Stem Cells Support Undifferentiated Cell Growth, Stem Cells, 2004, pp. 972-980, vol. 22, AlphaMed Press.

Xu, et al., Basic FGF and Suppression of BMP Signalling Sustain Undifferentiated Proliferation of Human ES Cells, Nature Methods, 2005, pp. 185-189, vol. 2, Issue 3.

Xudong, et al., Research Progress in Inducing Stem Cels to Differentiate toward the B-like Cells of Pancreatic Islet, Chinese Bulletin of Life Sciences, 2007, pp. 526-530, vol. 19, No. 5.

Yang et al., Novel cell immobilization method utilizing centrifugal force to achieve high-density hepatocyte culture in porous scaffold, Journal of Biomed Materials Research, Feb. 27, 2001, 379-386, 55, John Wiley & Sons, Inc.

Yang, et al., Evaluation of Humam MSCs Cell Cycle, Viability and Differentiation in Micromass Culture, Biorheology, 2006, pp. 489-496, vol. 43 (English Abstract Only).

Yang, et al., Survival of Pancreatic Islet Xenografts in NOD Mice with the Theracyte Device, Transplantation Proceedings, 2002, pp. 3349-3350, vol. 34.

Yasuda, et al., Development of Cystic Embryoid Bodies with Visceral Yolk-Sac-Like Structures from Mouse Embryonic Stem Cells Using Low-Adherence 96-Well Plate, Journal of Bioscience and Bioengineering, Apr. 4, 2009, pp. 442-446, vol. 107, No. 4.

Yoneda, et al., The Rho Kinases I and II Regulate Different Aspects of Myosin II Acitivity, The Journal of Cell Biology, 2005, pp. 443-445, vol. 170, No. 3.

Young, et al., Three-Dimensional Culture of Human Uterine Smooth Muscle Nyocytes on a Resorbably Scaffolding, Tissue Engineering, 2003, pp. 451-459, vol. 9, No. 3.

Yu, et al., Induced Pluripotent Stem Cell Lines Derived from Human Somatic Cells, Science, Dec. 21, 2007, pp. 1917-1920, vol. 318.

Yu, et al., Isolation of a Novel Population of Multipotent Adult Stem Cells from Human Hair Follicles, American Journal of Pathology, Jun. 6, 2006, pp. 1879-1888, vol. 168, No. 6.

Zalzman, et al., Differentiation of Human Liver-Derived, Insulin-Producing Cells Toward the B-Cell Phenotype, Diabetes, 2005, pp. 2568-2575, vol. 54.

Zembower, et al., Peptide Boronic Acids Versatile Synthetic Ligands for Affinity Chromatography of Serine Proteinases, International Journal Peptide Protein, 1996, pp. 405-413, vol. 47.

Zhang et al., MafA is a Key Regulator of Glucose-Stimulated Insulin Secretion, Molecular and Cellular Biology, Jun. 2005, pp. 4969-4976, vol. 25-12, American Society for Microbiology.

Zhang, et al., Differentiation Potential of Bone Marrow Mesenchymal Stem Cells into Retina in Normal and Laser-Injured Rat Eye, Science in China Series, 2004, pp. 241-250, vol. 47, No. 3.

Zhang, Jie, The Differentiation of Bone Marrow Mesenchymal Stem Cells into Retina in Rat Eye and the Therapeutical Effect on Severe Injured Retina, A Doctoral Thesis of Chinese PLA Acadamey of Military Medical Sciences, 2003, pp. 1-127.

Zhang, et al., Highly Efficient Differentiation of Human ES Cells and iPS Cells into Mature Pancreatic Insulin-Producing Cells, Cell Research, 2009, pp. 429-438, vol. 19, Issue 14.

Zhao et al., The Islet B Cell-enriched MafA Activator is a Key Regulator of Insulin Gene Transcription, Journal of Biological Chemistry, Mar. 25, 2005, pp. 11887-11894, vol. 280-12, The Amerian Society for Biochemistry and molecular Biology, Inc.

Zhao, et al., Derivation and Characterization of Hepatic Progenitor Cells from Human Embryonic Stem Cells, PLoS ONE Hepatic Progenitors from hESCs, Jul. 2009, e6468 pp. 1-10, vol. 4, Issue 7.

Zorn, et al., Vertebrate Endoderm Development and Organ Formation, Annual Review Cell Development Biology, 2009, pp. 221-251, vol. 25.

Zubaty, et al., Transplantation of Mesenchymal Stem Cells into RCS Rats for Retinal Repair, Investigative Ophthalmology and Visual Science, 2005, pp. 4160-B518, vol. 46, Supplement S.

Zuscik, et al., Regulation of Chondrogenesis and Chondrocyte Differentiation by Stress, J Clin Invest, 2008, pp. 429-438, vol. 118, Issue 2.

Cohick, et al., The Insulin-Like Growth Factors, Annual Reviews Physiol, 1993, pp. 131-153, vol. 55, Annual Reviews Inc.

Hebrok, et al., Notochord repression of endodermal Sonic hedgehog permits pancreas development, Genes & Development, Jun. 1, 1998, pp. 1705-1713, vol. 12, Issue 11, Cold Spring Harbor Laboratory Press.

Jaenisch, et al., Stem Cells, the Molecular Circuitry of Pluripotency and Nuclear Reprogramming, Cell, Feb. 22, 2008, pp. 567-582, vol. 132, Elsevier Inc.

Klajnert, et al., Fluorescence studies on PAMAM dendrimers interactions with bovine serum albumin, Bioelectrochemistry, 2002, pp. 33-35, vol. 55.

Kubota, et al., Growth factors essential for self-renewal and expansion of mouse spermatogonial stem cells, Cell Biology, Nov. 23, 2004, pp. 16489-16494, vol. 101, Issue 47.

Ratanasavanh,et al., Immunocytochemical Evidence for the Maintenance of Cytochrome P450 Isozymes, NADPH Cytochrome C Reductase, and Epoxide Hydrolase in Pure and Mixed Primary Cultures of Adult Human Hepatocytes, The Journal of Histochemistry and Cytocheinistry, 1986, pp. 527-533, vol. 34, Issue 4.

Schaefer-Graf, et al., Patterns of congenital anomalies and relationship to initial maternal fasting glucose levels in pregnancies complicated by type 2 and gestational diabetes, Am J Obstet Gynecol, 2000, pp. 313-320, vol. 182, Issue 2.

Brimble, S., et al., The Cell Surface Glycosphingolipids SSEA-3 and SSEA-4 Are Not Essential for Human ESC Pluripotency, Stem Cells, Jan. 2007, pp. 54-62, vol. 25.

Buta, et al., Reconsidering pluripotency tests: Do we still need teratoma assays?, Stem Cell Research, Mar. 26, 2013, pp. 552-562, vol. 11.

Chen, et al., Retinoic acid signaling is essential for pancreas development and promotes endocrine at the expense of exocrine cell differentiation in Xenopus, Developmental Biology, May 4, 2004, pp. 144-160, vol. 271.

Cirulli, et al., Netrins: beyond the brain, Molecular Cell Biology, Apr. 2007, pp. 296-306, vol. 8.

Furue, et al., Heparin propotes the growth of human embryonic stem cells in a defined serum-free medium, PNAS, Sep. 2008, pp. 13409-13414, vol. 105 Issue 36.

(56) References Cited

OTHER PUBLICATIONS

Gibco, Insulin-Transferin-Selenium-X 100X, Invitrogen Cell Culture, Apr. 2005, pp. 1, Form No. 3032.
Gomez, et al., Derivation of cat embryonic stem-like cells from in vitro-produced blastocysts on homologous and heterologous feeder cells, Theriogenology, May 11, 2010, pp. 498-515, vol. 74.
Gordon Weir., Do stem cells hold the key to a future cure for diabetes?, DiabetesVoice, Jun. 2008, pp. 29-31, vol. 53 Issue 2.
Hemisch, H., et al., Transcriptional Regulation in Endoderm Develoment: Characterization of an Enhancer Controlling Hnf3g Expression by Transgenesis and Targeted Mutagenesis, The EMBO Journal, 1997, 3995-4006, vol. 16(13).
Jean, et al., Pluripotent genes in avian stem cells, Development Growth & Differentitaion, 2013, pp. 41-51, vol. 55.
Kang, et al., Plasma treatment of textiles—Synthetic Polymer-Based Textiles, AATCC Review, 2004, pp. 29-33, Page number.
King, et al., Bioreactor development for stem cell expansion and controlled differentiation, Current Opinion in Chemical Biology, Jul. 25, 2007, pp. 394-398, vol. 11, Elsevier Ltd.
Kunisada, et al., Small molecules induce efficient differentiation into insulin-producing cells from human induced pluripotent stem cells, Stem Cell Research, Oct. 11, 2011, pp. 274-284, vol. 8.
Lavial, et al., Chicken Embryonic Stem Cells as a Non-Mammalian Embryonic Stem Cell Model, Development Growth Differentiation, Jan. 2010, pp. 101-114, vol. 52(1).
Lin, C., et al., Coagulation Dysregulation as a Barrier to Xenotransplantation in the Primate, Transplant Immunology, 2009; pp. 75-80, vol. 21.
Maria-Jesus Obregon, Thyroid hormone and adipocyte differentiation, Thyroid, 2008, pp. 185-195, vol. 18 Issue 2.
McMahon, et al., Noggin-mediated antagonism of BMP signaling is required for growth and patterning of the neural tube and somite, Genes & Development, Mar. 16, 1998, pp. 1438-1452, vol. 12.
Nakase, et al., Myeloid Antigen, CD13, CD14, and/ or CD33 Expression Is Restricted to Certain Lymphoid Neoplasms, Hematopathology, Jun. 1996, pp. 761-768, vol. 105 issue 6.
Narang, A., et al., Biological and Biomaterial Approaches for Improved Islet Transplantation, Pharmacological Review, Jun. 2006, pp. 194-243, vol. 58(2).
Ouziel-Yahalom, et al., Expansion and redifferentiation of adult human pancreatic islet cells, Biochemical and Biophysical Research Communications, Jan. 19, 2006, pp. 291-298, vol. 341.
Petitte, J., et al., Avian Pluripotent Stem Cells, Mechanisms of Development, 2004, pp. 1159-1168, vol. 121.
Ramiya, et al.. Reversal of insulin-dependent diabetes using islets generated in vitro from pancreatic stem cells, Nature Medicine, Mar. 2000, pp. 278-282, vol. 6 Issue 3.
Rother, et al., Challenges facing islet transplantation for the treatment of type 1 diabetes mellitus, The Journal of Clinical Investigation, 2004, pp. 877-883, vol. 114 Issue 7.
Rowely, et al., Meeting Lot-size Challenges of Manufacturing Adherent Cells for Therapy, Bio Process International, Mar. 2012, pp. 16-22, vol. 10 Issue 3.
SjöGren-Jansson; et al., Large-Scale Propagation of Four Undifferentiated Human Embryonic Stem Cell Lines in a Feeder-Free Culture System, Developmental Dynamics, Jun. 17, 2005, pp. 1304-1314, vol. 233.
Strizzi, et al., Netrin-1 regulates invasion and migration of mouse mammary epithelial cells overexpressing Cripto-1 in vitro in vivo, Journal of Cell Science, Jul. 7, 2005, pp. 4633-4643, vol. 118 Issue 20.
Suzuken., Differentiation of Multifunctional Stem Cells Using Human Feeder Cells, Research Papers of the Suzuken Memorial Foundation, 2007, pp. 193-197, vol. 2.
Yadlin, et al., Small-molecule inducers of insulin expression in pancreatic α-cells, PNAS, Aug. 24, 2010, pp. 115099-15104, vol. 107 Issue 34.
Yang JW, et al., Evaluation of human MSCs cell cycle, viability and differentiation in micromass culture, Bioheology, 2006, pp. 1-2, vol. 43 Issue (3-4).
Yim,et al., Proliferation and differentiation of human embryonic germ cell derivatives in bioactive polymeric fibrous scaffold, J.Biomater.Sci.Polymer Edn, Jan. 19, 2005, pp. 1193-1217, vol. 16 Issue 10.
Zulewski, et al., Muitipotential Nestin-Positive Stem Cells Isolated From Adult Pancreatic Islets Differentiate Ex Vivo Into Pancreatic Endocrine, Exocrine, and Hepatic Phenotypes, Diabetes, 2001, pp. 521-533, vol. 50.

* cited by examiner

Figure 1
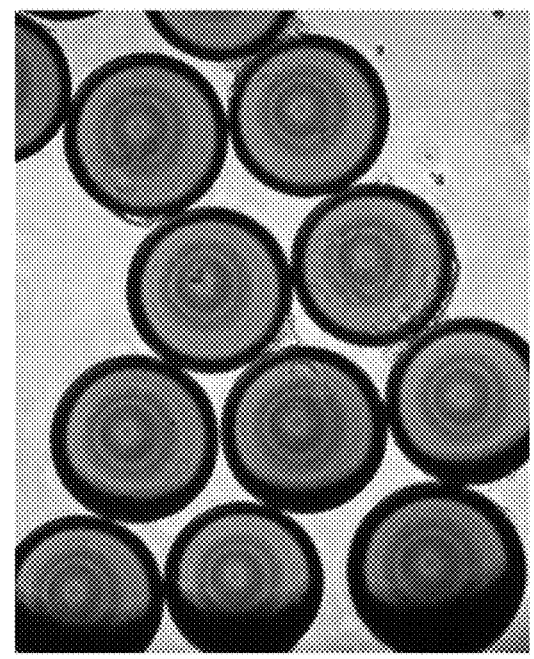
B.
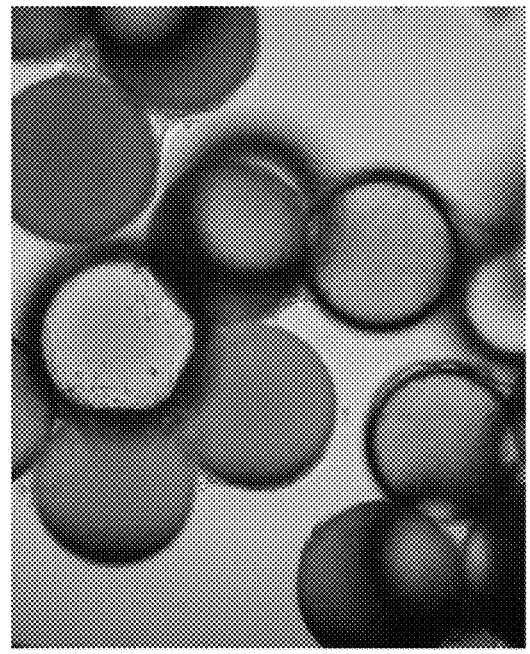
A.

Figure 39
A)
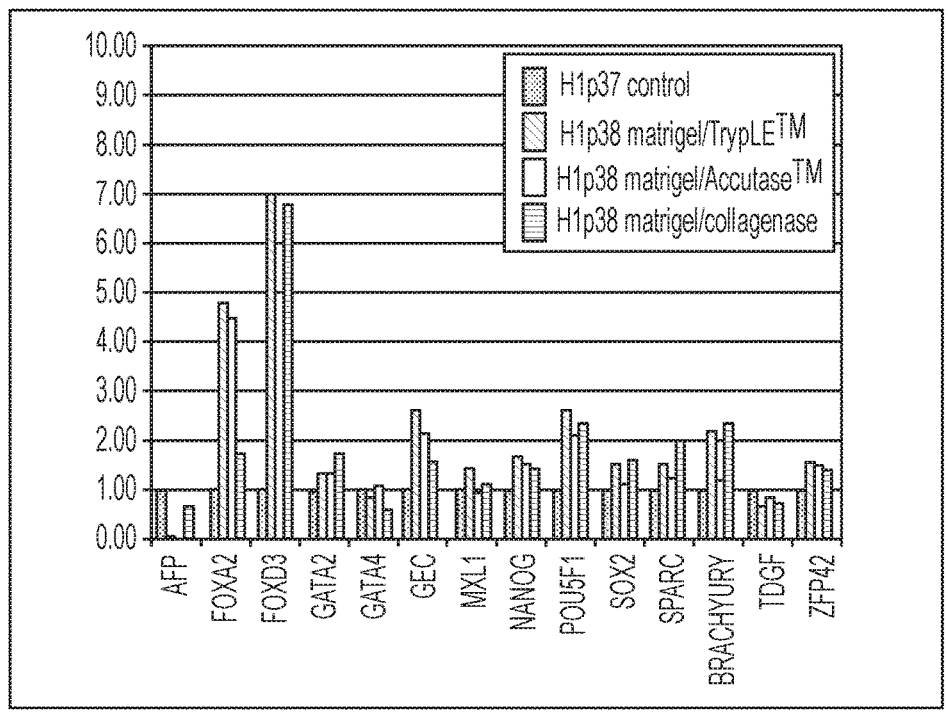
B)
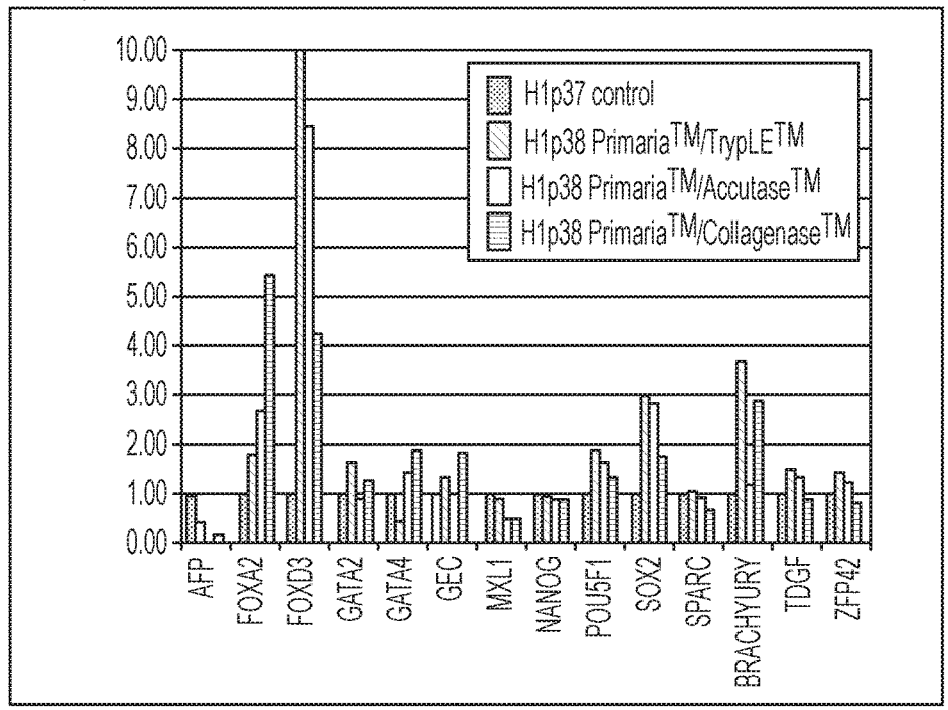

PLURIPOTENT STEM CELL CULTURE ON MICRO-CARRIERS

CROSS-REFERENCE TO RELATED APPLICATIONS

This application is a divisional of U.S. application Ser. No. 12/621,686, filed Nov. 19, 2009 (now abandoned), which claims priority to provisional Application No. 61/116,447, filed Nov. 20, 2008. The complete disclosures of the aforementioned related patent applications are hereby incorporated herein by reference for all purposes.

FIELD OF THE INVENTION

The present invention is directed to methods for the growth, expansion and differentiation of pluripotent stem cells on micro-carriers.

BACKGROUND

Pluripotent stem cells, such as, for example, embryonic stem cells have the ability to differentiate into all adult cell types. As such, embryonic stem cells may be a source of replacement cells and tissue for organs that have been damaged as a result of disease, infection, or congenital abnormalities. The potential for embryonic stem cells to be employed as a replacement cell source is hampered by the difficulty of propagating the cells in vitro while maintaining their pluripotency.

Current methods of culturing undifferentiated embryonic stem cells require complex culture conditions, such as, for example, culturing the embryonic stem cells in the presence of a feeder cell layer. Alternatively, media obtained by exposure to feeder cell cultures may be used to culture embryonic stem cells. Culture systems that employ these methods often use cells obtained from a different species than that of the stem cells being cultivated (xenogeneic cells). Additionally, these culture systems may be supplemented with animal serum.

Embryonic stem cells provide a potential resource for research and drug screening. At present, large-scale culturing of human embryonic stem cell lines is problematic and provides substantial challenges. Current in vitro methods to propagate pluripotent stem cells are carried out in tissue flasks on planar surfaces pre-coated with extracellular matrix (ECM) proteins or feeder cells. Planar cultures also require frequent subculturing because their limited surface area cannot support long-term growth of pluripotent stem cells. Micro-carrier-based methods of pluripotent stem cell culture may provide a solution. Micro-carriers have a high surface-area-to-volume ratio and, therefore, eliminate the surface area restriction of growing pluripotent stem cells on planar surfaces.

For example, Fok et at disclose stirred-suspension culture systems for the propagation of undifferentiated ESC—micro-carrier and aggregate cultures (Stem Cells 2005; 23:1333-1342.)

In another example, Abranches et at disclose the testing of Cytodex 3® (GE Healthcare Life Sciences, NJ), a microporous micro-carrier made up of a dextran matrix with a collagen layer at the surface for its ability to support the expansion of the mouse S25 ES cell line in spinner flasks (Biotechnol. Bioeng. 96 (2007), pp. 1211-1221.)

In another example, US20070264713 disclose a process for cultivating undifferentiated stem cells in suspension and in particular to a method for cultivating stem cells on micro-carriers in vessels.

In another example, WO2006137787 disclose a screening tool is used which comprises particulate matter or micro-carriers, such as beads, attached to a solid support, such as a micro titer plate, for the cultivation of cells on said micro-carriers.

In another example, WO2008004990 disclose a method of promoting the attachment, survival and/or proliferation of a stem cell in culture, the method comprising culturing a stem cell on a positively-charged support surface.

In another example, WO2007012144 disclose a bioreactor, comprising: a support surface; and a synthetic attachment polypeptide bound to the support surface wherein the synthetic attachment polypeptide is characterized by a high binding affinity for an embryonic stem cell or a multipotent cell.

SUMMARY

The present invention provides methods for the growth, expansion and differentiation of pluripotent stem cells on micro-carriers.

In one embodiment, the present invention provides a method for the propagation of pluripotent stem cells, comprising the steps of:
  a. Attaching a population of pluripotent stem cells to a first volume of micro-carriers,
  b. Culturing the pluripotent stem cells on the first volume of micro-carriers,
  c. Removing the pluripotent stem cells from the first volume of micro-carriers, and
  d. Attaching the population of pluripotent stem cells to a second volume of micro-carriers.

BRIEF DESCRIPTION OF THE DRAWINGS

FIG. 1: Rho-kinase inhibitor promotes attachment and growth of human embryonic stem cells to micro-carriers. Images of H9 cells grown in static culture for 2 days on HILLEX®II micro-carriers (Solohill, MI). The cells were cultured in mouse embryonic fibroblast conditioned medium (MEF-CM) with or without 10 µM Rho Kinase inhibitor, Y27632 ((Sigma-Aldrich, MO) A and B, respectively).

DETAILED DESCRIPTION

Figure 2:
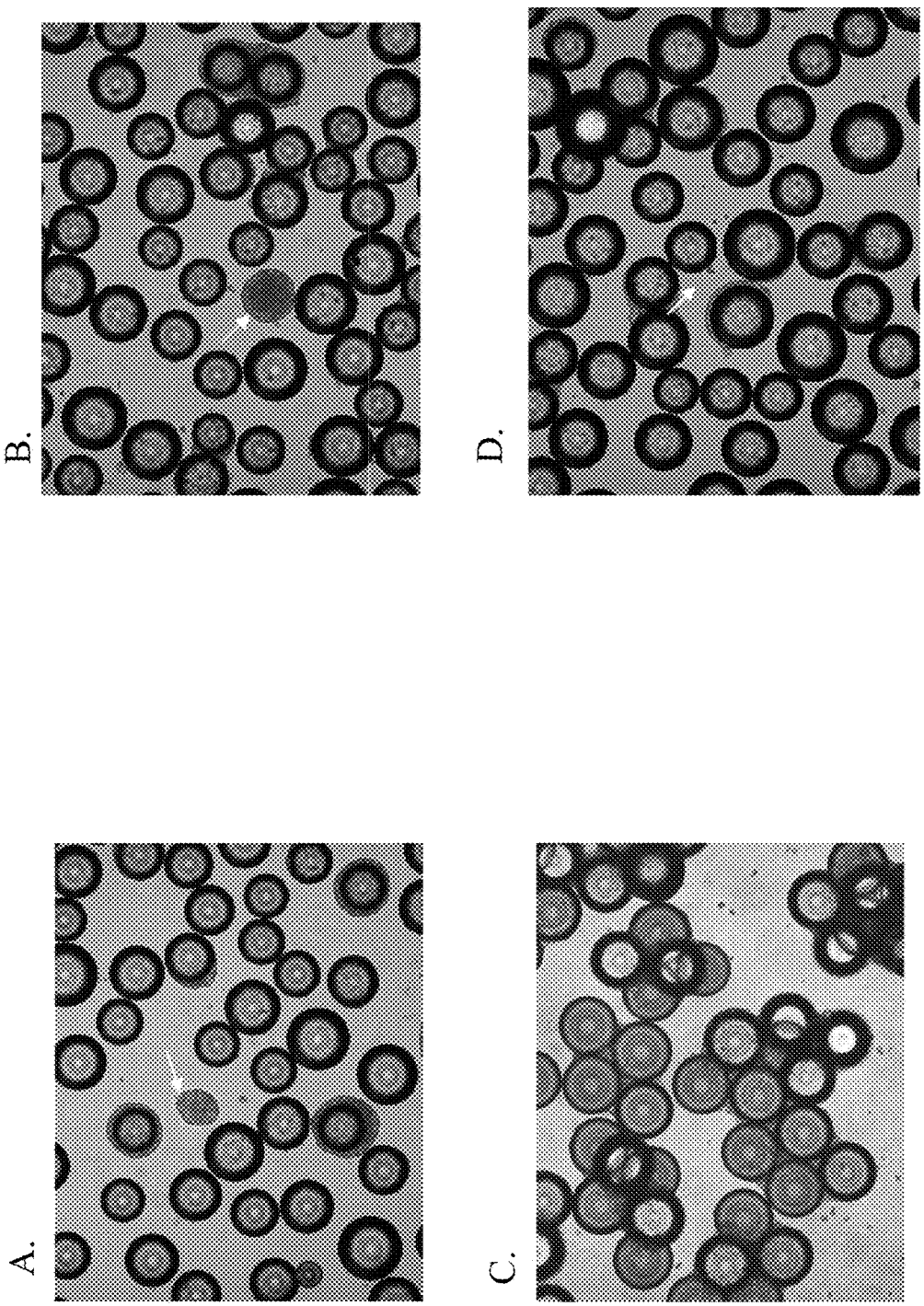
FIG. 2: H9 cells grown on micro-carriers. H9 cells were allowed to attach to various micro-carriers and placed on a rocking platform at 37° C. Plastic micro-carriers, ProNectinF micro-carriers, HILLEX®II micro-carriers (Solohill, MI), and Plastic Plus micro-carriers, were used (A, B, C, D respectively). Growth after 3 days showed cells on HILLEX®II (Solohill, MI) with best cell attachment to the micro-carriers. Arrows identify cells forming aggregates without attachment to the micro-carriers.

For clarity of disclosure, and not by way of limitation, the detailed description of the invention is divided into the following subsections that describe or illustrate certain features, embodiments or applications of the present invention.

Definitions

Stem cells are undifferentiated cells defined by their ability at the single cell level to both self-renew and differentiate to produce progeny cells, including self-renewing progenitors, non-renewing progenitors, and terminally differentiated cells. Stem cells are also characterized by their ability to differentiate in vitro into functional cells of various cell lineages from multiple germ layers (endoderm, mesoderm and ectoderm), as well as to give rise to tissues of multiple germ layers following transplantation and to contribute substantially to most, if not all, tissues following injection into blastocysts.

Stem cells are classified by their developmental potential as: (1) totipotent, meaning able to give rise to all embryonic and extraembryonic cell types; (2) pluripotent, meaning able to give rise to all embryonic cell types; (3) multipotent, meaning able to give rise to a subset of cell lineages, but all within a particular tissue, organ, or physiological system (for example, hematopoietic stem cells (HSC) can produce progeny that include HSC (self-renewal), blood cell restricted oligopotent progenitors and all cell types and elements (e.g., platelets) that are normal components of the blood); (4) oligopotent, meaning able to give rise to a more restricted subset of cell lineages than multipotent stem cells; and (5) unipotent, meaning able to give rise to a single cell lineage (e.g., spermatogenic stem cells).

Differentiation is the process by which an unspecialized ("uncommitted") or less specialized cell acquires the features of a specialized cell such as, for example, a nerve cell or a muscle cell. A differentiated or differentiation-induced cell is one that has taken on a more specialized ("committed") position within the lineage of a cell. The term "committed", when applied to the process of differentiation, refers to a cell that has proceeded in the differentiation pathway to a point where, under normal circumstances, it will continue to differentiate into a specific cell type or subset of cell types, and cannot, under normal circumstances, differentiate into a different cell type or revert to a less differentiated cell type. De-differentiation refers to the process by which a cell reverts to a less specialized (or committed) position within the lineage of a cell. As used herein, the lineage of a cell defines the heredity of the cell, i.e., which cells it came from and what cells it can give rise to. The lineage of a cell places the cell within a hereditary scheme of development and differentiation. A lineage-specific marker refers to a characteristic specifically associated with the phenotype of cells of a lineage of interest and can be used to assess the differentiation of an uncommitted cell to the lineage of interest.

Various terms are used to describe cells in culture. "Maintenance" refers generally to cells placed in a growth medium under conditions that facilitate cell growth and/or division that may or may not result in a larger population of the cells. "Passaging" refers to the process of removing the cells from one culture vessel and placing them in a second culture vessel under conditions that facilitate cell growth and/or division.

A specific population of cells, or a cell line, is sometimes referred to or characterized by the number of times it has been passaged. For example, a cultured cell population that has been passaged ten times may be referred to as a P10 culture. The primary culture, i.e., the first culture following the isolation of cells from tissue, is designated P0. Following the first subculture, the cells are described as a secondary culture (P1 or passage 1). After the second subculture, the cells become a tertiary culture (P2 or passage 2), and so on. It will be understood by those of skill in the art that there may be many population doublings during the period of passaging; therefore the number of population doublings of a culture is greater than the passage number. The expansion of cells (i.e., the number of population doublings) during the period between passaging depends on many factors, including but not limited to the seeding density, substrate, medium, growth conditions, and time between passaging.

"β-cell lineage" refer to cells with positive gene expression for the transcription factor PDX-1 and at least one of the following transcription factors: NGN-3, Nkx2.2, Nkx6.1, NeuroD, Is1-1, HNF-3 beta, MAFA, Pax4, or Pax6. Cells expressing markers characteristic of the β cell lineage include β cells.

"Cells expressing markers characteristic of the definitive endoderm lineage" as used herein refer to cells expressing at least one of the following markers: SOX-17, GATA-4, HNF-3 beta, GSC, Cer1, Nodal, FGF8, Brachyury, Mix-like homeobox protein, FGF4 CD48, eomesodermin (EOMES), DKK4, FGF17, GATA-6, CXCR4, C-Kit, CD99, or OTX2. Cells expressing markers characteristic of the definitive endoderm lineage include primitive streak precursor cells, primitive streak cells, mesendoderm cells and definitive endoderm cells.

"Cells expressing markers characteristic of the pancreatic endoderm lineage" as used herein refer to cells expressing at least one of the following markers: PDX-1, HNF-1beta, PTF-1 alpha, HNF-6, or HB9. Cells expressing markers characteristic of the pancreatic endoderm lineage include pancreatic endoderm cells.

"Cells expressing markers characteristic of the pancreatic endocrine lineage" as used herein refer to cells expressing at least one of the following markers: NGN-3, NeuroD, Islet-1, PDX-1, NKX6.1, Pax-4, or PTF-1 alpha. Cells expressing markers characteristic of the pancreatic endocrine lineage include pancreatic endocrine cells, pancreatic hormone expressing cells, and pancreatic hormone secreting cells, and cells of the β-cell lineage.

"Definitive endoderm" as used herein refers to cells which bear the characteristics of cells arising from the epiblast during gastrulation and which form the gastrointestinal tract and its derivatives. Definitive endoderm cells express the following markers: CXCR4, HNF-3 beta, GATA-4, SOX-17, Cerberus, OTX2, goosecoid, c-Kit, CD99, and Mix11.

"Extraembryonic endoderm" as used herein refers to a population of cells expressing at least one of the following markers: SOX-7, AFP, or SPARC.

"Markers" as used herein, are nucleic acid or polypeptide molecules that are differentially expressed in a cell of interest. In this context, differential expression means an increased level for a positive marker and a decreased level for a negative marker. The detectable level of the marker nucleic acid or polypeptide is sufficiently higher or lower in the cells of interest compared to other cells, such that the cell of interest can be identified and distinguished from other cells using any of a variety of methods known in the art.

"Mesendoderm cell" as used herein refers to a cell expressing at least one of the following markers: CD48, eomesodermin (EOMES), SOX-17, DKK4, HNF-3 beta, GSC, FGF17, or GATA-6.

"Pancreatic endocrine cell" or "pancreatic hormone expressing cell" as used herein refers to a cell capable of expressing at least one of the following hormones: insulin, glucagon, somatostatin, and pancreatic polypeptide.

"Pancreatic hormone secreting cell" as used herein refers to a cell capable of secreting at least one of the following hormones: insulin, glucagon, somatostatin, and pancreatic polypeptide.

"Pre-primitive streak cell" as used herein refers to a cell expressing at least one of the following markers: Noda1, or FGF8.

"Primitive streak cell" as used herein refers to a cell expressing at least one of the following markers: Brachyury, Mix-like homeobox protein, or FGF4.

Micro-Carriers

"Micro-carriers" refers to particles, beads, or pellets useful for attachment and growth of anchorage dependent cells in culture. The micro-carriers have the following properties: (a) They are small enough to allow them to be used in suspension cultures (with a stirring rate that does not cause significant shear damage to the micro-carriers or the cells); (b) They are solid, or have a solid core with a porous coating on the surface; and (c) Their surfaces (exterior and interior surface in case of porous carriers) may be positively or negatively charged. In one aspect, the micro-carriers have an overall particle diameter between about 150 and 350 μm, and have a positive charge density of between about 0.8 and 2.0 meq/g. Useful micro-carriers include, without limitation, Cytodex 1®, Cytodex 2®, or Cytodex 3® (GE Healthcare Life Sciences, NJ).

In another aspect, the micro-carrier is a solid carrier. Solid carriers are particularly suitable for adhesion cells, e.g., anchorage-dependent cells. The carrier particle can also be a porous micro-carrier.

"Porous micro-carriers" refers to particles useful for attachment and growth of anchorage-dependent cells in culture. The porous micro-carriers have the following properties: (a) they are small enough to allow them to be used in suspension cultures (with a stirring rate that does not cause significant shear damage to the micro-carriers or the cells); (b) they have pores and interior spaces of sufficient size to allow cells to migrate into the interior spaces of the particle and (c) their surfaces (exterior and interior) may be positively or negatively charged. In one series of embodiments, the carriers (a) have an overall particle diameter between about 150 and 350 µm; (b) have pores having an average pore opening diameter of between about 15 and about 40 µm; and (c) have a positive charge density of between about 0.8 and 2.0 meq/g. In some embodiments, the positive charge is provided by DEAE (N,N-diethylaminoethyl) groups. Useful porous micro-carriers include, without limitation, Cytopore 1® and Cytopore 2® (GE Healthcare Life Sciences, Piscataway N.J.). Micro-carriers may be any shape, but are typically roughly spherical in shape, and can be either macro- or micro-porous, or solid.

Both porous and solid types of micro-particulate carriers are commercially available from suppliers. Examples of commercially available micro-carriers include Cytodex 1® and Cytodex 3® (GE Healthcare Life Sciences, NJ), which are both dextran-based micro-carriers from GE Healthcare Life Sciences. Porous micro-carriers on the market include Cytoline as well as Cytopore products also from GE Healthcare Life Sciences. Biosilon (NUNC) and Cultispher (Percell Biolytica) are also commercially available. In a further aspect, the micro-carriers can be comprised of, or coated with polycarbonate or mixed cellulose esters.

Micro-carriers suitable for use in the present invention can be comprised of natural or synthetically-derived materials. Examples include collagen-based micro-carriers, dextran-based micro-carriers, or cellulose-based micro-carriers, as well as glass, ceramics, polymers, or metals. The micro-carrier can be protein-free or protein-coated, for example, with collagen. In a further aspect the micro-carrier can be comprised of, or coated with, compounds that enhance binding of the cell to the micro-carrier and enhance release of the cell from the micro-carrier including, but not limited to, poly(monostearoylglyceride co-succinic acid), poly-D,L-lactide-co-glycolide, sodium hyaluronate, collagen, fibronectin, laminin, elastin, lysine, n-isopropyl acrylamide, vitronectin.

Micro-Carriers for Cell Culture

Micro-carrier culture is a technique, which makes possible the practical high yield culture of anchorage-dependent, cells, for example, human embryonic stem cells. Micro-carriers have been specifically developed for the culture of cells, such as human embryonic stem cells, in culture volumes ranging from a few milliliters to greater than one thousand liters. The micro-carrier is biologically inert and provides a strong but non-rigid substrate for stirred micro-carrier cultures. The micro-carriers may be transparent, allowing microscopic examination of the attached cells. Cytodex 3® (GE Healthcare Life Sciences, NJ) consists of a thin layer of denatured collagen chemically coupled to a matrix of crosslinked dextran. The denatured collagen layer on Cytodex 3® (GE Healthcare Life Sciences, NJ) is susceptible to digestion by a variety of proteases, including trypsin and collagenase, and provides the ability to remove cells from the micro-carriers while maintaining maximum cell viability, function, and integrity.

Protein free micro-carriers can be used to culture human embryonic stem cells. For example, micro-carriers for use in manufacturing and laboratory or research use sold under the tradename HILLEX® (SoloHill Engineering, Inc., MI.) are modified polystyrene beads with cationic trimethyl ammonium attached to the surface to provide a positively charged surface to the micro-carrier. The bead diameter ranges from about 90 to about 200 microns in diameter.

Micro-carrier-based methods of cell culture provided many advantages including ease of downstream processing in many applications. Micro-carriers are typically roughly spherical in shape, and can be either porous or solid. The use of micro-carriers for cell attachment facilitates the use of stirred tank and related reactors for growth of anchorage-dependent cells. The cells attach to the readily suspended micro-carriers. The requirement for suspendability limits the physical parameters of the micro-carriers. Thus, micro-carriers commonly have a mean diameter in the range of 50-2000 microns. In some applications solid-type micro-carriers range from about 100 to about 250 microns whereas porous-type micro-carriers range from about 250 to about 2500 microns. These size ranges allow for selection of micro-carriers, which are large enough to accommodate many anchorage-dependent cells, while small enough to form suspensions with properties suitable for use in stirred reactors.

Among the factors considered in using micro carriers and the like are: attachment efficiency, immunogenicity, biocompatibility, ability to biodegrade, time to reach confluence, the growth parameters of attached cells including maximum attainable density per unit surface area, detachment techniques where required, and the efficiency of the detachment, scalability of the culture conditions as well as homogeneity of the culture under scaled-up conditions, the ability to successfully scale-up detachment procedures, and whether the micro-carriers will be used for implantation. These considerations can be influenced by the surface properties of the micro-carrier, as well as by the porosity, diameter, density, and handling properties of the micro-carrier.

For example, the density of the micro-carriers is a consideration. Excessive density may cause the micro-carriers to settle out of the suspension, or tend to remain completely towards the bottom of the culture vessel, and thus may result in poor bulk mixing of the cells, culture medium and gaseous phases in the reactor. On the other hand, a density that is too low may result in excessive floating of the micro-carrier. A density of 1.02 to 1.15 $g/cm^3$ is typical of many micro-carriers.

The small diameter of micro-carriers and the volume of particles that can be added to a reactor allows the micro-carriers to contribute substantial surface area in vast excess to that found in roller bottles or other methods of growing anchorage-dependent cells, e.g. on plates. Porous micro-carriers provide even greater surface area per unit volume or weight. These porous micro-carriers possess large cavities that are available for the growth of anchorage-dependent cells. These cavities increase the surface area greatly, and may protect cells from detrimental mechanical effects, such as shear stress, for example from mixing or from gas sparging.

The micro-carrier surface may be textured to enhance cell attachment and proliferation. The micro-carrier surface texture be achieved by techniques including, but not limited to, molding, casting, leeching and etching. The resolution of the features of the textured surface may be on the nanoscale. The textured surface may be used to induce a specific cell alignment on the micro-carrier surface. The surface of the pores within the porous micro-carriers may also be textured to enhance cell attachment and proliferation. Pore surface texture be achieved by techniques such as but not limited to molding, casting, leeching and etching.

The micro-carrier surface may be plasma-coated to impart a specific charge to micro-carrier surfaces. These charges may enhance cell attachment and proliferation.

In other embodiments, the micro-carriers are composed of, or coated with, thermoresponsive polymers such as poly-N-isopropylacrylamide, or have electromechanical properties.

Both porous and solid types of microparticulate carriers are commercially available from suppliers. Examples of commercially available solid micro-carriers include Cytodex 1® and Cytodex 3® (GE Healthcare Life Sciences, NJ), which are both dextran-based micro-carriers from GE Healthcare Life Sciences. Porous micro-carriers on the market include Cytoline as well as Cytopore products also from GE Healthcare Life Sciences. Biosilon (NUNC) and Cultispher (Percell Biolytica) are also commercially available.

The micro-carriers may also contain a bioactive agent. The micro-carrier may also contain a bioactive agent that may regulate the growth or function of cells or the tissue milieu these factors may include but are not limited to fibroblast growth factors, erythropoietin, vascular endothelial cell growth factors, platelet derived growth factors, bone morphogenic proteins, transforming growth factors, tumor necrosis factors, epidermal growth factors, insulin-like growth factors. Complete factors, mimetics or active fragments thereof may be used.

The micro-carriers may be inoculated with a second cell type and co-cultured with the pluripotent stem cells. In one embodiment the two (or more) cell types may be adherent to an individual micro-carrier in equal or un-equal proportions. The two or more cell types can be inoculated onto the micro-carrier at the same time point or they may be inoculated at different times. The micro-carriers can be treated in such a manner to preferentially adhere specific cell types onto specific regions of the micro-carrier. In a further embodiment, the micro-carrier with adherent single or multiple cell types can be co-cultured in a culture vessel with a second cell type cultured in suspension.

Second cell types may include, for example, epithelial cells (e.g., cells of oral mucosa, gastrointestinal tract, nasal epithelium, respiratory tract epithelium, vaginal epithelium, corneal epithelium), bone marrow cells, adipocytes, stem cells, keratinocytes, melanocytes, dermal fibroblasts, keratinocytes, vascular endothelial cells (e.g., aortic endothelial cells, coronary artery endothelial cells, pulmonary artery endothelial cells, iliac artery endothelial cells, microvascular endothelial cells, umbilical artery endothelial cells, umbilical vein endothelial cells, and endothelial progenitors (e.g., CD34+, CD34+/CD117+ cells)), myoblasts, myocytes, hepatocytes, smooth muscle cells, striated muscle cells, stromal cells, and other soft tissue cells or progenitor cells, chondrocytes, osteoblasts, islet cells, nerve cells including but not limited to neurons, astrocytes, Schwann cells, enteric glial cells, oligodendrocytes.

Pluripotent Stem Cells

Characterization of Pluripotent Stem Cells

Pluripotent stem cells may express one or more of the stage-specific embryonic antigens (SSEA) 3 and 4, and markers detectable using antibodies designated Tra-1-60 and Tra-1-81 (Thomson et al., Science 282:1145, 1998). Differentiation of pluripotent stem cells in vitro results in the loss of SSEA-4, Tra-1-60, and Tra-1-81 expression (if present) and increased expression of SSEA-1. Undifferentiated pluripotent stem cells typically have alkaline phosphatase activity, which can be detected by fixing the cells with 4% paraformaldehyde and then developing with Vector Red as a substrate, as described by the manufacturer (Vector Laboratories, Burlingame Calif.) Undifferentiated pluripotent stem cells also typically express OCT4 and TERT, as detected by RT-PCR.

Another desirable phenotype of propagated pluripotent stem cells is a potential to differentiate into cells of all three germinal layers: endoderm, mesoderm, and ectoderm tissues. Pluripotency of stem cells can be confirmed, for example, by injecting cells into severe combined immunodeficient (SCID) mice, fixing the teratomas that form using 4% paraformaldehyde, and then examining them histologically for evidence of cell types from the three germ layers. Alternatively, pluripotency may be determined by the creation of embryoid bodies and assessing the embryoid bodies for the presence of markers associated with the three germinal layers.

Propagated pluripotent stem cell lines may be karyotyped using a standard G-banding technique and compared to published karyotypes of the corresponding primate species. It is desirable to obtain cells that have a "normal karyotype," which means that the cells are euploid, wherein all human chromosomes are present and not noticeably altered.

Sources of Pluripotent Stem Cells

The types of pluripotent stem cells that may be used include established lines of pluripotent cells derived from tissue formed after gestation, including pre-embryonic tissue (such as, for example, a blastocyst), embryonic tissue, or fetal tissue taken any time during gestation, typically but not necessarily before approximately 10-12 weeks gestation. Non-limiting examples are established lines of human embryonic stem cells or human embryonic germ cells, such as, for example the human embryonic stem cell lines H1, H7, and H9 (WiCell). Also contemplated is use of the compositions of this disclosure during the initial establishment or stabilization of such cells, in which case the source cells would be primary pluripotent cells taken directly from the source tissues. Also suitable are cells taken from a pluripotent stem cell population already cultured in the absence of feeder cells. Also suitable are mutant human embryonic stem cell lines, such as, for example, BG01v (BresaGen, Athens, Ga.). Also suitable are pluripotent stem cells derived from non-pluripotent cells, such as, for example, an adult somatic cells.

Attaching Pluripotent Stem Cells to the Micro-Carriers Suitable for Use in the Present Invention Pluripotent stem cells may be cultured on a planar substrate by any method in the art, prior to attaching to micro-carriers. For example, pluripotent stem cells may be cultured on planar substrates, treated with an extracellular matrix protein (e.g. MATRIGEL). Alternatively, pluripotent stem cells may be cultured on planar substrates seeded with a feeder cell layer.

In one embodiment, the pluripotent stem cells are embryonic stem cells. In an alternate embodiment, the embryonic stem cells are human.

In one aspect of the present invention, pluripotent stem cells are released from a planar substrate by treating the pluripotent stem cells with a protease that will release the cells from the planar substrate. The protease may be, for example, collagenase, TrypLE™ Express, Accutase™, trypsin, and the like.

In one embodiment, the pluripotent stem cells are released from the micro-carrier substrate by treating the cells with Accutase™ for about five to about ten minutes.

In one embodiment, the pluripotent stem cells are released from the micro-carrier substrate by treating the cells with 0.05% trypsin/EDTA for about ten to about twenty minutes.

In one embodiment, the pluripotent stem cells are released from the micro-carrier substrate by treating the cells with TrypLE™ Express for about five to about twenty minutes.

In one embodiment, the pluripotent stem cells are released from the micro-carrier substrate by treating the cells with 10 mg/ml Collagenase for about five to about ten minutes.

The released pluripotent cells are added to medium containing micro-carriers at a specific density. In one embodiment, the pluripotent stem cells were seeded at about 4,000 to about 30,000 cells per $cm^2$ of micro-carriers.

The released pluripotent cells are added to medium containing micro-carriers. In one embodiment, the attachment of the pluripotent stem cells is enhanced by treating the pluripotent stem cells with a Rho kinase inhibitor. The Rho kinase inhibitor may be Y27632 (Sigma-Aldrich, MO). Alternatively, the Rho kinase inhibitor is Glycyl-H 1152 dihydrochloride.

In one embodiment, the pluripotent stem cells are treated with Y27632 at a concentration from about 1 µM to about 10 µM. In one embodiment, the pluripotent stem cells are treated with Y27632 at a concentration of about 10 µM.

In one embodiment, the pluripotent stem cells are treated with Glycyl-H 1152 dihydrochloride at a concentration from about 0.25 µM to about 5 µM. In one embodiment, the pluripotent stem cells are treated with Glycyl-H 1152 dihydrochloride at a concentration of about 2.5 µM.

The medium containing the micro-carriers may be agitated. Agitation as used in the present invention may be the movement of the culture medium. Such agitation may be achieved manually, or, alternatively, by use of apparatus, such as, for example, a rocking platform, a spinner flask, and the like. In one embodiment, the medium containing the micro-carriers is agitated by the use of manual movement. The dish containing the micro-carriers and cells is moved back and forth for less than 30 seconds.

The medium containing the micro-carriers may be agitated. In one embodiment, the medium containing the micro-carriers is agitated by the use of a spinner flask. The spinner flask (Corning, Lowell, Mass.) is placed on a stir plate at 30-70 RPM depending on bead type.

In an alternate embodiment, the medium containing the micro-carriers is agitated by the use of a rocking platform (Vari-mix, Barnstead, Dubuque, Iowa). The rocking platform speed is about one rotation in 2 seconds.

Differentiating Pluripotent Stem Cells on Micro-Carriers

In one embodiment, the pluripotent stem cells may be differentiated into cells expressing markers characteristic of the definitive endoderm lineage on micro-carriers. Alternatively, the pluripotent stem cells may be differentiated into cells expressing markers characteristic of the pancreatic endoderm lineage on micro-carriers. Alternatively, the pluripotent stem cells may be differentiated into cells expressing markers characteristic of the pancreatic endocrine lineage on micro-carriers.

In an alternate embodiment, the pluripotent stem cells may be propagated on micro-carriers, then differentiated into cells expressing markers characteristic of the definitive endoderm lineage on planar surfaces. Alternatively, the pluripotent stem cells may be propagated on micro-carriers, then differentiated into cells expressing markers characteristic of the pancreatic endoderm lineage on planar surfaces. Alternatively, the pluripotent stem cells may be propagated on micro-carriers, then differentiated into cells expressing markers characteristic of the pancreatic endocrine lineage on planar surfaces.

Pluripotent stem cells treated in accordance with the methods of the present invention may be differentiated into a variety of other cell types by any suitable method in the art. For example, pluripotent stem cells treated in accordance with the methods of the present invention may be differentiated into neural cells, cardiac cells, hepatocytes, and the like.

For example, pluripotent stem cells treated in accordance with the methods of the present invention may be differentiated into neural progenitors and cardiomyocytes according to the methods disclosed in WO2007030870.

In another example, pluripotent stem cells treated in accordance with the methods of the present invention may be differentiated into hepatocytes according to the methods disclosed in U.S. Pat. No. 6,458,589.

Formation of Cells Expressing Markers Characteristic of the Definitive Endoderm Lineage Pluripotent stem cells may be differentiated into cells expressing markers characteristic of the definitive endoderm lineage by any method in the art.

For example, pluripotent stem cells may be differentiated into cells expressing markers characteristic of the definitive endoderm lineage according to the methods disclosed in D'Amour et al, Nature Biotechnology 23, 1534-1541 (2005).

For example, pluripotent stem cells may be differentiated into cells expressing markers characteristic of the definitive endoderm lineage according to the methods disclosed in Shinozaki et al, Development 131, 1651-1662 (2004).

For example, pluripotent stem cells may be differentiated into cells expressing markers characteristic of the definitive endoderm lineage according to the methods disclosed in McLean et al, Stem Cells 25, 29-38 (2007).

For example, pluripotent stem cells may be differentiated into cells expressing markers characteristic of the definitive endoderm lineage according to the methods disclosed in D'Amour et al, Nature Biotechnology 24, 1392-1401 (2006).

Markers characteristic of the definitive endoderm lineage are selected from the group consisting of SOX17, GATA4, HNF-3 beta, GSC, CER1, Nodal, FGF8, Brachyury, Mix-like homeobox protein, FGF4, CD48, eomesodermin (EOMES), DKK4, FGF17, GATA6, CXCR4, C-Kit, CD99, and OTX2. Suitable for use in the present invention is a cell that expresses at least one of the markers characteristic of the definitive endoderm lineage. In one aspect of the present invention, a cell expressing markers characteristic of the definitive endoderm lineage is a primitive streak precursor cell. In an alternate aspect, a cell expressing markers characteristic of the definitive endoderm lineage is a mesendoderm cell. In an alternate aspect, a cell expressing markers characteristic of the definitive endoderm lineage is a definitive endoderm cell.

In another example, pluripotent stem cells treated according to the methods of the present invention may be differentiated into cells expressing markers characteristic of the definitive endoderm lineage by culturing the pluripotent stem cells in medium containing activin A in the absence of serum, then culturing the cells with activin A and serum, and then culturing the cells with activin A and serum of a different concentration. An example of this method is disclosed in Nature Biotechnology 23, 1534-1541 (2005).

In another example, pluripotent stem cells treated according to the methods of the present invention may be differentiated into cells expressing markers characteristic of the definitive endoderm lineage by culturing the pluripotent stem cells in medium containing activin A in the absence of serum, then culturing the cells with activin A with serum of another concentration. An example of this method is disclosed in D'Amour et al, Nature Biotechnology, 2005.

In another example, pluripotent stem cells treated according to the methods of the present invention may be differentiated into cells expressing markers characteristic of the definitive endoderm lineage by culturing the pluripotent stem cells in medium containing activin A and a Wnt ligand in the absence of serum, then removing the Wnt ligand and culturing the cells with activin A with serum. An example of this method is disclosed in Nature Biotechnology 24, 1392-1401 (2006).

In another example, pluripotent stem cells treated according to the methods of the present invention may be differentiated into cells expressing markers characteristic of the definitive endoderm lineage according to the methods disclosed in U.S. patent application Ser. No. 11/736,908, assigned to LifeScan, Inc.

In another example, pluripotent stem cells treated according to the methods of the present invention may be differentiated into cells expressing markers characteristic of the definitive endoderm lineage according to the methods disclosed in U.S. patent application Ser. No. 11/779,311, assigned to LifeScan, Inc.

Formation of Cells Expressing Markers Characteristic of the Pancreatic Endoderm Lineage Pluripotent stem cells may be differentiated into cells expressing markers characteristic of the pancreatic endoderm lineage by any method in the art.

For example, pluripotent stem cells may be differentiated into cells expressing markers characteristic of the pancreatic endoderm lineage according to the methods disclosed in D'Amour et al, Nature Biotechnology 24, 1392-1401 (2006).

For example, cells expressing markers characteristic of the definitive endoderm lineage obtained according to the methods of the present invention are further differentiated into cells expressing markers characteristic of the pancreatic endoderm lineage, by treating the cells expressing markers characteristic of the definitive endoderm lineage with a fibroblast growth factor and the hedgehog signaling pathway inhibitor KAAD-cyclopamine, then removing the medium containing the fibroblast growth factor and KAAD-cyclopamine and subsequently culturing the cells in medium containing retinoic acid, a fibroblast growth factor and KAAD-cyclopamine. An example of this method is disclosed in Nature Biotechnology 24, 1392-1401 (2006).

For example, cells expressing markers characteristic of the definitive endoderm lineage obtained according to the methods of the present invention are further differentiated into cells expressing markers characteristic of the pancreatic endoderm lineage, by treating the cells expressing markers characteristic of the definitive endoderm lineage with retinoic acid one fibroblast growth factor for a period of time, according to the methods disclosed in U.S. patent application Ser. No. 11/736,908, assigned to LifeScan, Inc.

For example, cells expressing markers characteristic of the definitive endoderm lineage obtained according to the methods of the present invention are further differentiated into cells expressing markers characteristic of the pancreatic endoderm lineage, by treating the cells expressing markers characteristic of the definitive endoderm lineage with retinoic acid (Sigma-Aldrich, MO) and exendin 4, then removing the medium containing DAPT (Sigma-Aldrich, MO) and exendin 4 and subsequently culturing the cells in medium containing exendin 1, IGF-1 and HGF. An example of this method is disclosed in Nature Biotechnology 24, 1392-1401 (2006).

For example, cells expressing markers characteristic of the pancreatic endoderm lineage obtained according to the methods of the present invention are further differentiated into cells expressing markers characteristic of the pancreatic endocrine lineage, by culturing the cells expressing markers characteristic of the pancreatic endoderm lineage in medium containing exendin 4, then removing the medium containing exendin 4 and subsequently culturing the cells in medium containing exendin 1, IGF-1 and HGF. An example of this method is disclosed in D'Amour et al, Nature Biotechnology, 2006.

For example, cells expressing markers characteristic of the pancreatic endoderm lineage obtained according to the methods of the present invention are further differentiated into cells expressing markers characteristic of the pancreatic endocrine lineage, by culturing the cells expressing markers characteristic of the pancreatic endoderm lineage in medium containing DAPT (Sigma-Aldrich, MO) and exendin 4. An example of this method is disclosed in D'Amour et al, Nature Biotechnology, 2006.

For example, cells expressing markers characteristic of the pancreatic endoderm lineage obtained according to the methods of the present invention are further differentiated into cells expressing markers characteristic of the pancreatic endocrine lineage, by culturing the cells expressing markers characteristic of the pancreatic endoderm lineage in medium containing exendin 4. An example of this method is disclosed in D'Amour et al, Nature Biotechnology, 2006.

For example, cells expressing markers characteristic of the pancreatic endoderm lineage obtained according to the methods of the present invention are further differentiated into cells expressing markers characteristic of the pancreatic endocrine lineage, by treating the cells expressing markers characteristic of the pancreatic endoderm lineage with a factor that inhibits the Notch signaling pathway, according to the methods disclosed in U.S. patent application Ser. No. 11/736,908, assigned to LifeScan, Inc.

For example, cells expressing markers characteristic of the pancreatic endoderm lineage obtained according to the methods of the present invention are further differentiated into cells expressing markers characteristic of the pancreatic endocrine lineage, by treating the cells expressing markers characteristic of the pancreatic endoderm lineage with a factor that inhibits the Notch signaling pathway, according to the methods disclosed in U.S. patent application Ser. No. 11/779,311, assigned to LifeScan, Inc.

For example, cells expressing markers characteristic of the pancreatic endoderm lineage obtained according to the methods of the present invention are further differentiated into cells expressing markers characteristic of the pancreatic endocrine lineage, by treating the cells expressing markers characteristic of the pancreatic endoderm lineage with a factor that inhibits the Notch signaling pathway, according to the methods disclosed in U.S. patent application Ser. No. 11/736,908, assigned to LifeScan, Inc.

For example, cells expressing markers characteristic of the pancreatic endoderm lineage obtained according to the methods of the present invention are further differentiated into cells expressing markers characteristic of the pancreatic endocrine lineage, by treating the cells expressing markers characteristic of the pancreatic endoderm lineage with a factor that inhibits the Notch signaling pathway, according to the methods disclosed in U.S. patent application Ser. No. 11/779,311, assigned to LifeScan, Inc.

Markers characteristic of the pancreatic endocrine lineage are selected from the group consisting of NGN3, NEUROD, ISL1, PDX1, NKX6.1, PAX4, NGN3, and PTF-1 alpha. In one embodiment, a pancreatic endocrine cell is capable of expressing at least one of the following hormones: insulin, glucagon, somatostatin, and pancreatic polypeptide. Suitable for use in the present invention is a cell that expresses at least one of the markers characteristic of the pancreatic endocrine lineage. In one aspect of the present invention, a cell expressing markers characteristic of the pancreatic endocrine lineage is a pancreatic endocrine cell. The pancreatic endocrine cell may be a pancreatic hormone-expressing cell. Alternatively, the pancreatic endocrine cell may be a pancreatic hormone-secreting cell.

In one aspect of the present invention, the pancreatic endocrine cell is a cell expressing markers characteristic of the β cell lineage. A cell expressing markers characteristic of the β cell lineage expresses PDX1 and at least one of the following transcription factors: NGN3, NKX2.2, NKX6.1, NEUROD, ISL1, HNF-3 beta, MAFA, PAX4, or PAX6. In one aspect of the present invention, a cell expressing markers characteristic of the β cell lineage is a β cell.

The present invention is further illustrated, but not limited by, the following examples.

EXAMPLES

Example 1: Attachment and Proliferation of Human Embryonic Stem Cells on Micro-Carriers To determine if human embryonic stem cells can attach and proliferate on micro-carriers, H9 cells passage 52 were released from MATRIGEL™ (BD Biosciences, CA) coated plates with TrypLE™ Express. They were then incubated with micro-carriers and MEF-CM. Suspensions of ProNectinF (PN), Plastic (P), PlasticPlus (PP), HILLEX®II (H), collagen (Col) and FACT III (SoloHill, MI) micro-carriers were prepared according to manufacturer's instructions. After 2 days at 37° C., Table 1 describes the attachment and growth of the H9 cells on the micro-carriers based on daily images. Few cells attached and/or proliferated on most micro-carriers tested. H9 cells did attach and proliferate on HILLEX®II micro-carriers (Solohill, MI) but images showed fewer cell-bead aggregates after 2 days in static culture (FIG. 1B).

To improve the attachment and proliferation of human embryonic stem cells on micro-carriers, a small molecule inhibitor of Rho-associated coiled coil forming protein serine/threonine kinase, Rho kinase inhibitor was added to the media. Specifically, Y27632, Y, (Sigma-Aldrich, MO) was used. MEF-CM plus 10 µM Y27632 (Sigma-Aldrich, MO) was changed daily. In the presence of 10 µM Y27632 (Sigma-Aldrich, MO) the H9 cells attached and formed aggregates with all micro-carriers tested (Table 2). By analysis of images, human embryonic stem cells grown on HILLEX®II micro-carriers (Solohill, MI) appeared to attach and proliferate better than human embryonic stem cells on other micro-carriers tested. Additionally, H9 cells attached better to HILLEX®II (Solohill, MI) in the presence of the Rho kinase inhibitor (FIG. 1A compared to 1B).

Figure 3:
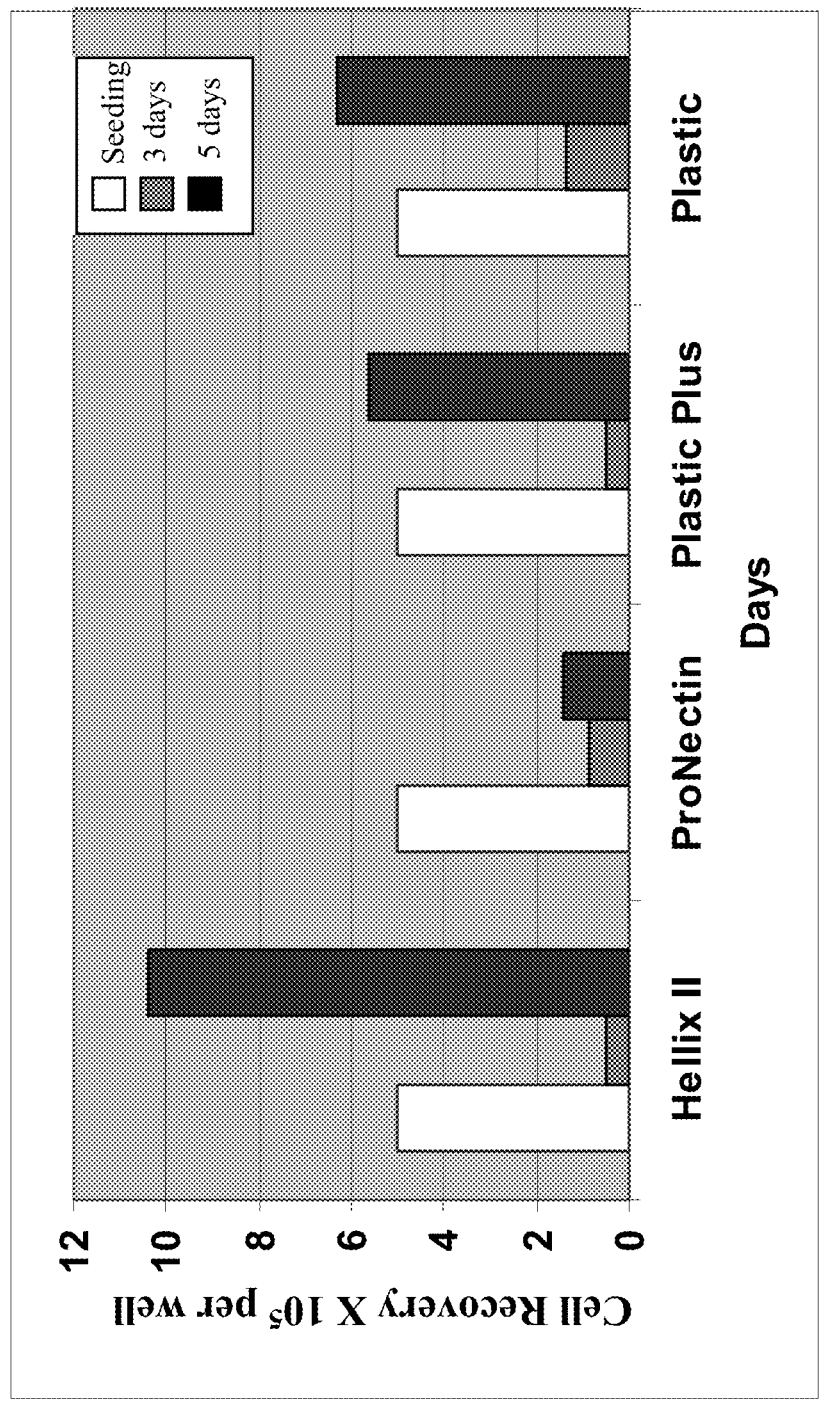
FIG. 3: H9 cell proliferation on micro-carriers. H9 cells were attached to HILLEX®II micro-carriers, ProNectinF micro-carriers, Plastic Plus micro-carriers, and Plastic micro-carriers (Solohill, MI) and placed in a 6 well dish on a rocking platform at 37° C. in the presence of 10 µM Y27632 (Sigma-Aldrich, MO) and MEF-CM. The initial cell seeding density is the value at day 0. Day 3 and day 5 cell numbers are shown.

Expansion of human embryonic stem cells for a cell therapy application is necessary to meet product demand. Currently the best techniques for expansion include spinner flasks and bioreactors. Both of these techniques require physical movement of the micro-carriers in suspension. To determine the effect of motion on the growth of the human embryonic stem cells on micro-carriers, 6 or 12 well dishes were placed on a rocking platform in a 37° C. incubator. After growth for 3 days, the cell aggregates began to release from some of the micro-carriers. FIG. 2A, B, D illustrates that the cell aggregates disassociated from the Plastic Plus, Plastic, or Pronectin micro-carriers. In contrast, the cells remained attached to the HILLEX® II micro-carriers (Solohill, MI) and proliferated FIG. 2C. Example 4 describes the dissociation method used prior to cell counting in a Guava PCA-96 with Viacount Flex (Guava Technologies, Hayward, Calif.). Measuring the growth rate of the cells on micro-carriers reveals a dip in cell number at day 3 compared to the starting number at seeding. This is likely due to poor initial attachment of the cells to the micro-carriers followed by an expansion afterwards until the experiment was terminated at day 5. H9 cells on HILLEX®II micro-carriers (Solohill, MI) have the highest proliferation rate compared to the other bead types, likely due to better attachment of the cells to the HILLEX® II micro-carriers (Solohill, MI) (FIGS. 2, 3). This demonstrates that the HILLEX® II micro-carriers (Solohill, MI) can support growth of H9 cells in suspension. This was further validated after repeat passaging, see Example 5.

Figure 4:
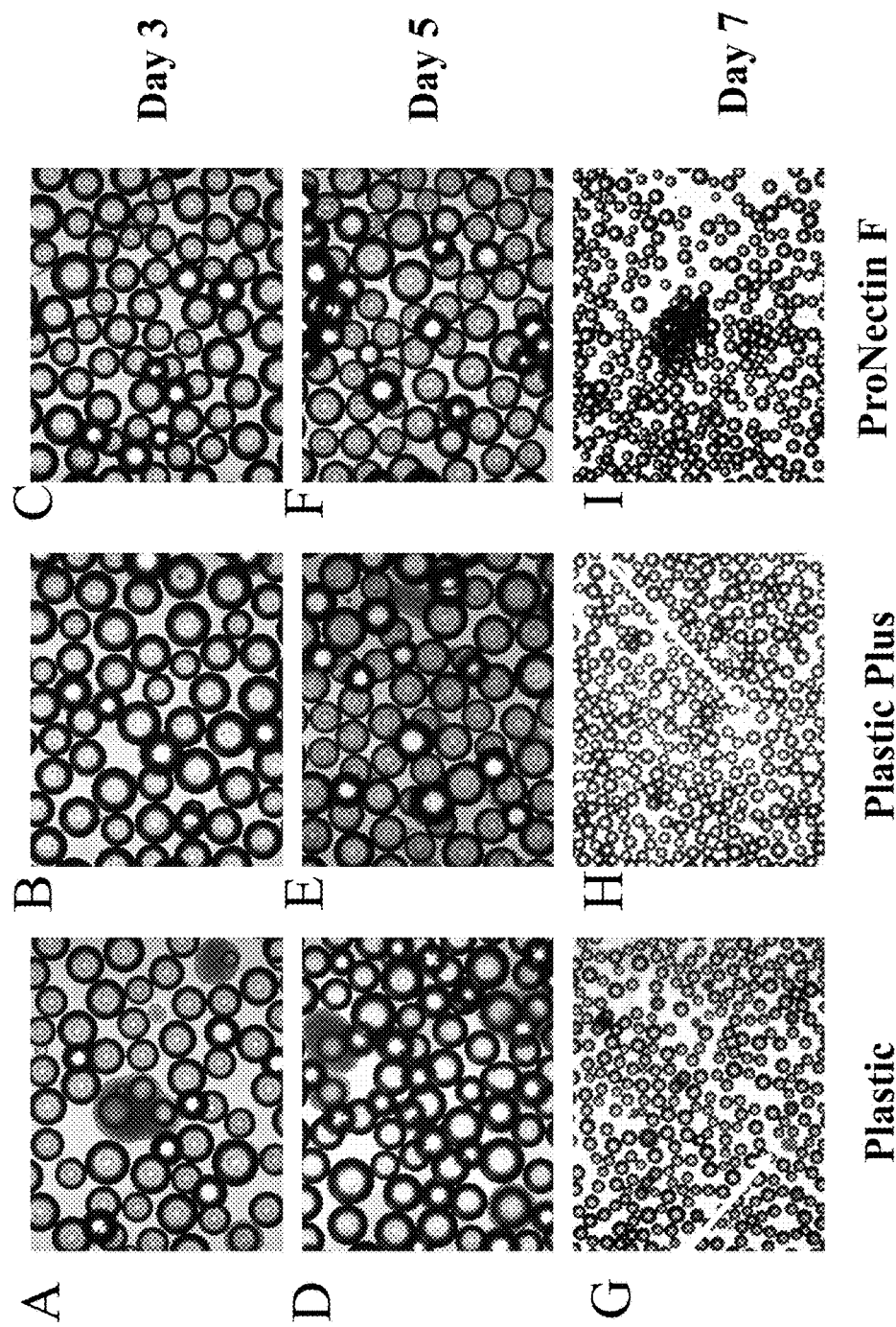
FIG. 4: H1 cell images after attachment to micro-carriers. Images of cells at days 3, 5 and 7 are shown attached to ProNectinF micro-carriers, Plastic Plus micro-carriers, and Plastic micro-carriers. The cells were grown in MEF-CM with 10 µM Y27632 (Sigma-Aldrich, MO) in a 12 well dish on a rocking platform at 37° C. Cells formed aggregates independent of binding to Plastic Plus and Plastic micro-carriers (arrows in G, H).
Figure 5:
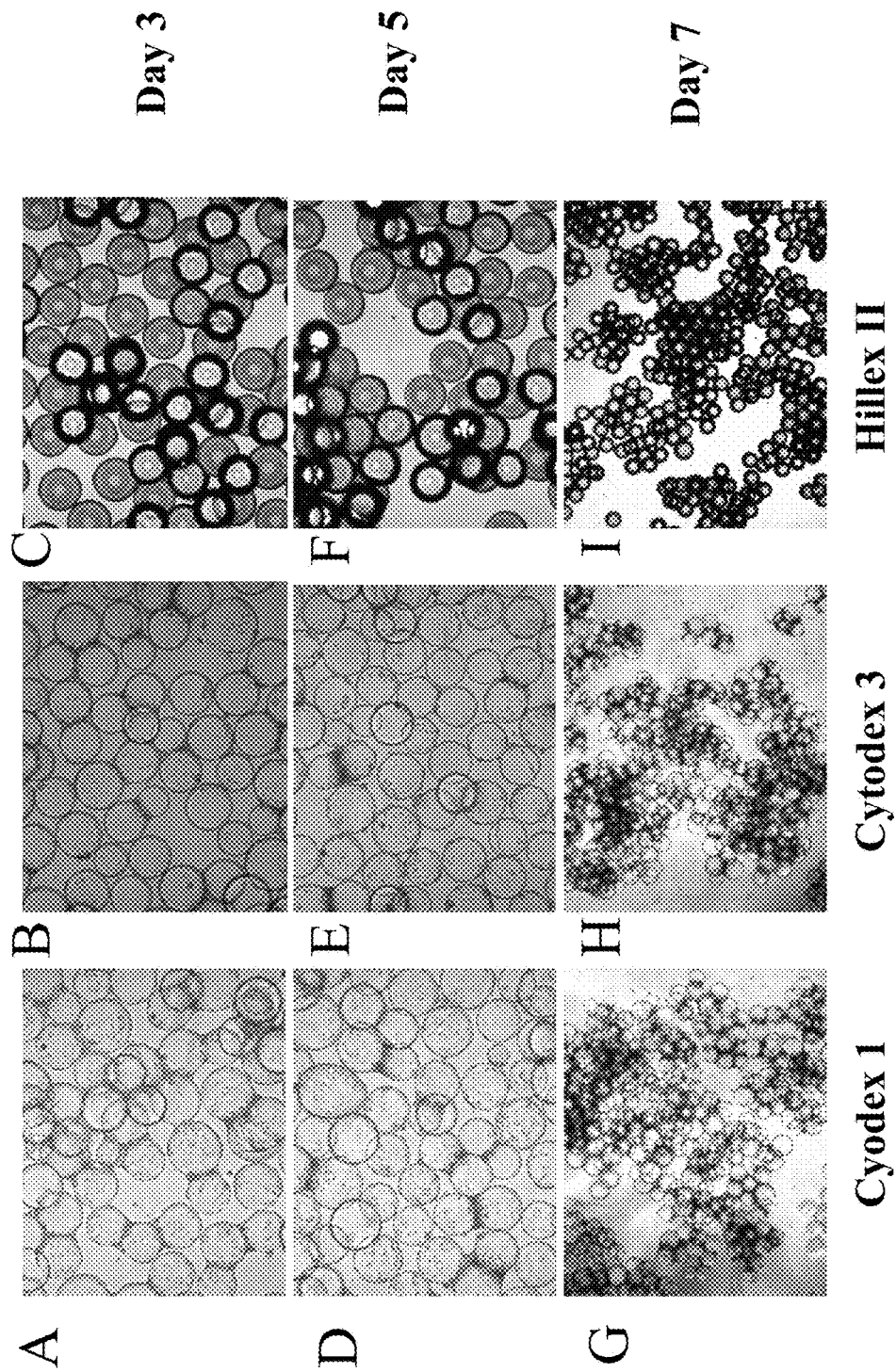
FIG. 5: H1 cell images after attachment to micro-carriers. Images of cells at days 3, 5 and 7 are shown attached to Cytodex 1® micro-carriers, Cytodex 3® micro-carriers (GE Healthcare Life Sciences, NJ) and HILLEX®II micro-carriers (Solohill, MI). The cells were grown in MEF-CM with 10 µM Y27632 (Sigma-Aldrich, MO) in a 12 well dish on a rocking platform at 37° C.
Figure 6:
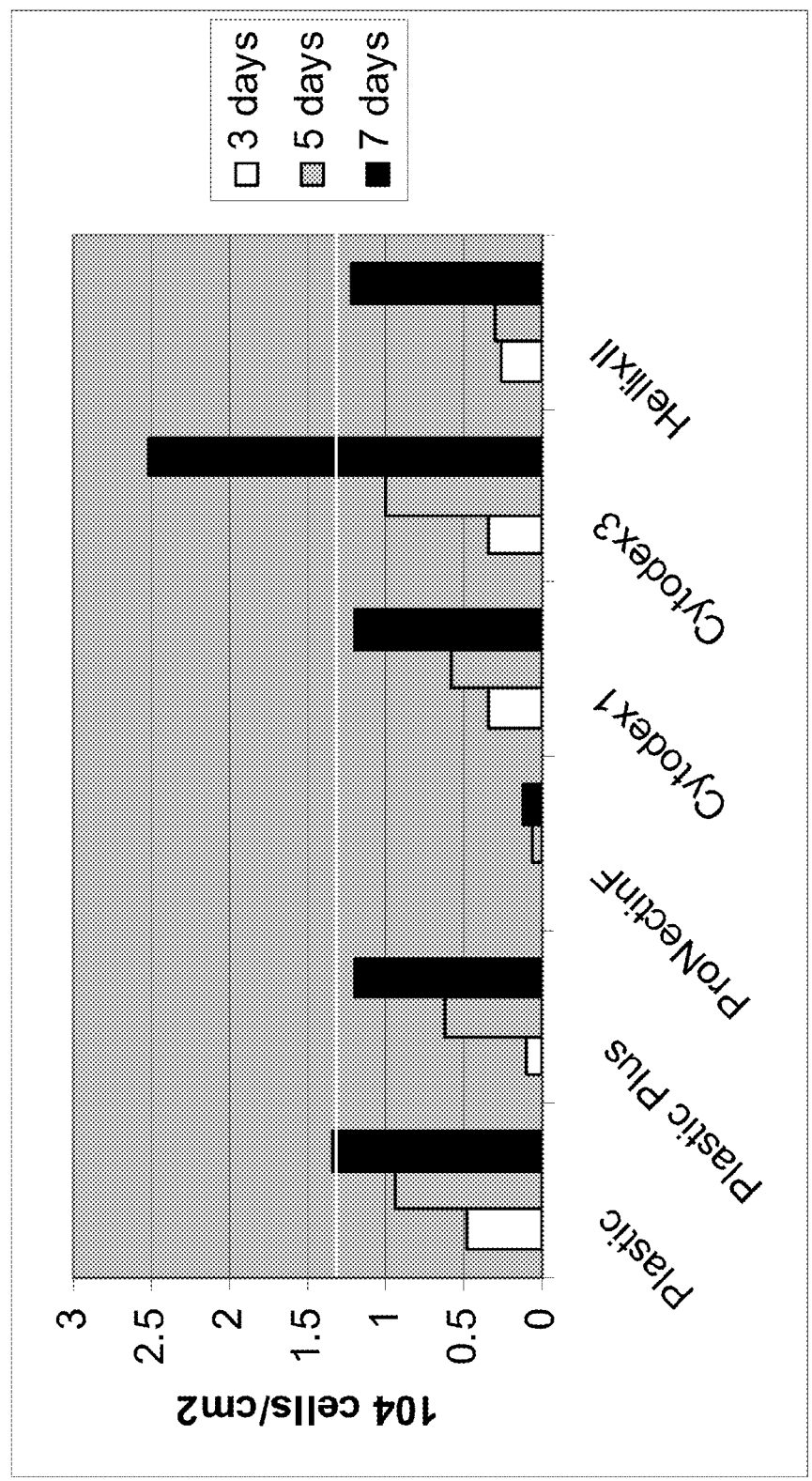
FIG. 6: H1 cell proliferation on micro-carriers. H1 cells were allowed to attach to HILLEX®II micro-carriers (Solohill, MI), Cytodex 1® micro-carriers (GE Healthcare Life Sciences, NJ), Cytodex 3® micro-carriers (GE Healthcare Life Sciences, NJ), ProNectinF micro-carriers (Solohill, MI), Plastic Plus micro-carriers (Solohill, MI), and Plastic micro-carriers (Solohill, MI) and placed in a 12 well dish on a rocking platform at 37° C. in the presence of 10 µM Y27632 (Sigma-Aldrich, MO) and MEF-CM. The initial cell seeding density is the value at day 0. Day 3, 5, and 7 cell numbers are shown. The initial seeding density was 13,333 cells/cm$^2$, as indicated by the line.

The H1 human embryonic cell line was also tested for growth on micro-carriers for large-scale expansion. Because a Rho kinase inhibitor, Y27632 (Sigma-Aldrich, MO), was necessary for attachment of the H9 cell line, it was also assumed to be necessary for H1 cells. Cytodex 1®, Cytodex 3® (GE Healthcare Life Sciences, NJ), HILLEX®II, Plastic, ProNectinF, Plastic Plus micro-carriers (SoloHill Ann Arbor, MI) were prepared according to the manufacturer's instructions. The H1 human embryonic stem cells at passage 47 were seeded at about 13,333 cells/cm$^2$ of micro-carriers in MEF-CM plus 10 µM Y27632 (Sigma-Aldrich, MO). Cells and micro-carriers were placed in a 12 well non-tissue culture treated dish at 15 cm$^2$ per 12 well on a rocking platform at 37° C. to allow movement of the micro-carriers and medium. After 3, 5 and 7 days, one well was imaged, harvested, and counted. The ability of cells to attach depended on the bead type. Similar results were observed with the H1 line as with the H9 line. Specifically, cells seeded onto Plastic, Plastic Plus or ProNectinF micro-carriers did not attach and/or proliferate well (FIG. 4). Cells seeded onto HILLEX®II (Solohill, MI), Cytodex 1®, or Cytodex 3® (GE Healthcare Life Sciences, NJ) micro-carriers attached and proliferated well (FIG. 5). Cells were detached according to Example 4 and counted for yield. Cells grown on Cytodex 3® micro-carriers (GE Healthcare Life Sciences, NJ) exhibited the highest cell number after 7 days in culture (FIG. 6).

Example 2: Optimal Concentrations of Y27632 and Other Rho Kinase Inhibitors for Cell Attachment and Growth To determine the concentration of Rho kinase inhibitor that best supports attachment and growth of the human embryonic stem cells on micro-carriers, the following experiments were conducted.

Figure 7:
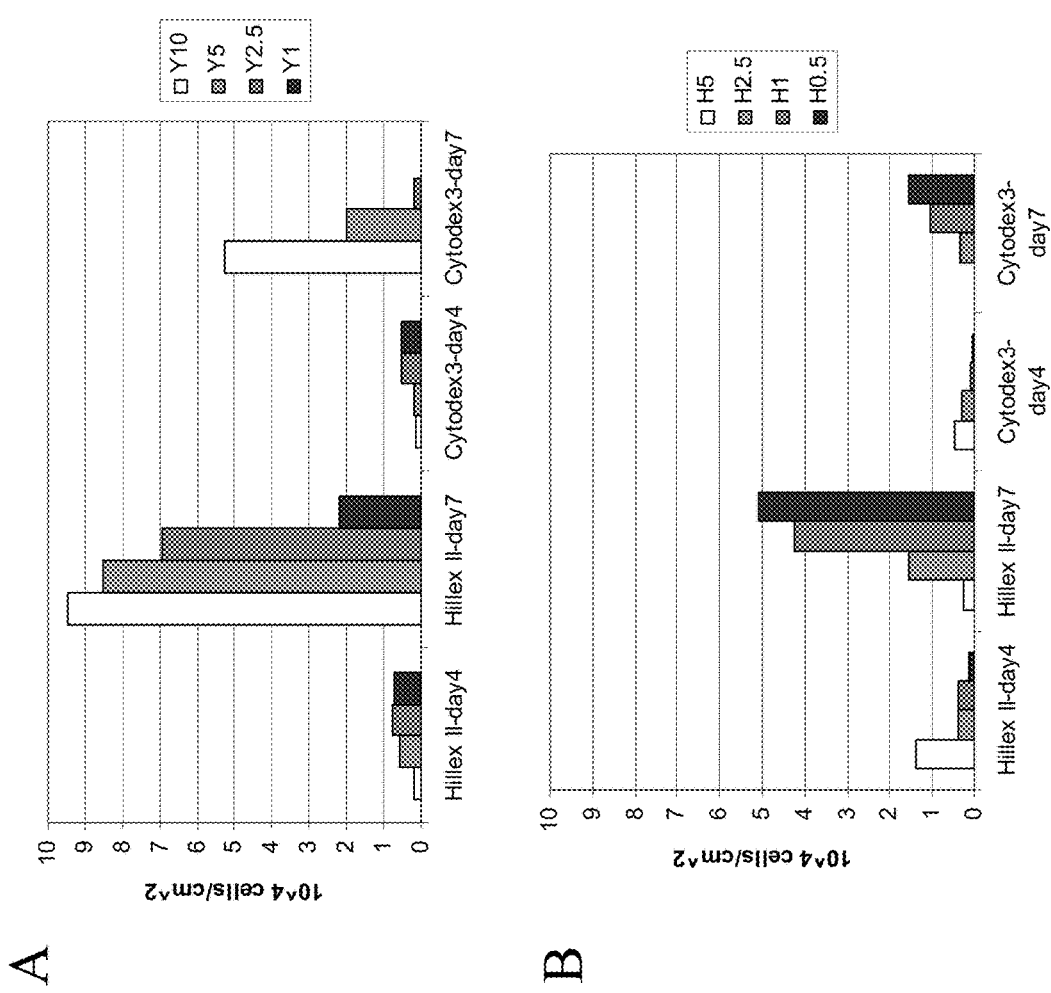
FIG. 7: H9 cell proliferation on micro-carriers in various concentrations of Rho kinase inhibitors. Cells were grown in a 12 well plate on a rocking platform and counted at day 4 and 7 to determine attachment and proliferation rate. A. H9 cells were grown in MEF-CM with 1, 2.5, 5, or 10 µM Y27632 (Sigma-Aldrich, MO). B. H9 cells were grown in MEF-CM with 0.5, 1, 2.5, or 5 µM Glycyl-H 1152 dihydrochloride (Tocris, MO).

A starting aliquot of 13,333 cells/cm² H9 cells at passage 44 was seeded onto 15 cm² of micro-carriers in a single well of a 12 well non-tissue culture treated plate. The cells were placed at 37° C. for at least 60 minutes before placing them onto a rocking platform at 37° C. Prior to adding the cells, HILLEX®II (Solohill, MI) and Cytodex 3® (GE Healthcare Life Sciences, NJ) micro-carriers were prepared as directed by the manufacturer. Cells were grown in MEF-CM plus a range of Rho kinase inhibitor concentrations, Y27632 at 10, 5, 2.5 or 1 μM, or (S)-(+)-4-Glycyl-2-methyl-1-[(4-methyl-5-isoquinolinyl)sulfonyl]-hexahydro-1H-1,4-diazepine dihydrochloride (Glycyl-H 1152 dihydrochloride (H), Tocris, MO) at 5, 2.5, 1 or 0.5 μM). The medium was changed daily and one well of cells was counted at 4 and 7 days after seeding for yield and viability (FIGS. 7, A and B). Overall, 10 or 5 μM Y27632 (Sigma-Aldrich, MO) showed the best cell proliferation (day 7) while 2.5 and 1.0 μM appeared to have the best attachment (day 4). Concentrations of 1 and 0.5 μM Glycyl-H 1152 dihydrochloride (Tocris, MO) showed the best cell proliferation (day 7) while 5 μM appeared to have the best attachment (day 4).

Figure 8:
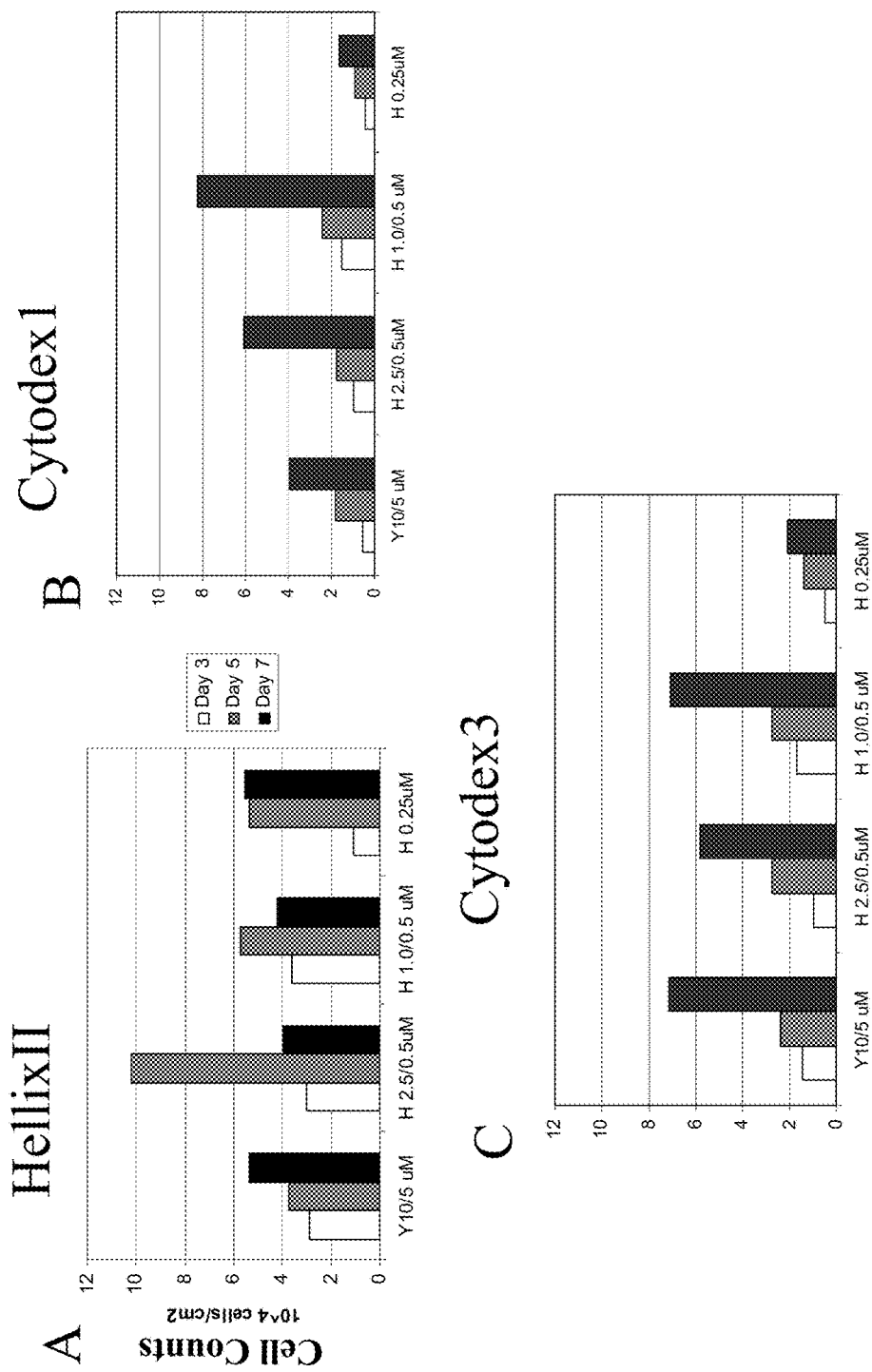
FIG. 8: H1 cells were grown in decreasing concentrations of Rho kinase inhibitors. H1p38 cells were grown in the presence of Y27632 (Sigma-Aldrich, MO) or Glycyl-H 1152 dihydrochloride (Tocris, MO) for two days at decreasing concentrations (10 µM/5 µM, 2.5 µM/0.5 µM or 1.0 µM/0.5 µM) or at 0.25 µM Glycyl-H 1152 dihydrochloride (Tocris, MO) continuously. Cells were allowed to attach to HILLEX®II (Solohill, MI), Cytodex 1®, or Cytodex 3® ((GE Healthcare Life Sciences, NJ) A, B, C, respectively). Cells were counted at 3, 5 and 7 days post seeding.

Next a dose titration of the Rho kinase inhibitor was attempted since it has been characterized as a promoting apoptosis. H1 cells at passage 48 were dissociated from MATRIGEL™ (BD Biosciences, CA) coated plates with TrypLE™ Express. The cells were then seeded onto 15 cm² of micro-carriers into a single well of a 12 well non-tissue culture treated plate. HILLEX®II (Solohill, MI), Cytodex 1®, or Cytodex 3® (GE Healthcare Life Sciences, NJ) micro-carriers were tested with decreasing amounts of Rho kinase inhibitor: 10 μM Y27632 (Sigma-Aldrich, MO) was used on day one followed by 0.5 μM on day two (Y10/5 μM); 2.5 μM Glycyl-H 1152 dihydrochloride (Tocris, MO) was used on day one followed by 0.5 μM on day two (H2.5/0.5 μM); 1 μM Glycyl-H 1152 dihydrochloride (Tocris, MO) was used on day one followed by 0.5 μM Glycyl-H 1152 dihydrochloride (Tocris, MO) on day two (H1/0.5 μM); or continuous addition of 0.25 μM Glycyl-H 1152 dihydrochloride (Tocris, MO) was applied daily in MEF-CM (H0.25 μM). H1 cells and micro-carriers were agitated every 45 minutes for 3 hours at 37° C. before being placed on a rocking platform at 37° C. Cells were counted after 3, 5 and 7 days on the rocking platform at 37° C. (FIG. 8). Overall the best concentration of Glycyl-H 1152 dihydrochloride (Tocris, MO) was 1-2.5 μM on day one and 0.5 μM on day 2 followed by withdrawal of the compound. The cells exhibited similar growth rates at these concentrations of Glycyl-H 1152 dihydrochloride (Tocris, MO) compared to 10 μM Y27632 (Sigma-Aldrich, MO) for all micro-carriers tested. Maintaining the cells in 0.25 μM Glycyl-H 1152 dihydrochloride (Tocris, MO) resulted in poor cell yield. Using a minimal amount of Rho-kinase inhibitor also helps reduce costs for the process and maybe beneficial to cell proliferation. These data also show that human embryonic stem cells did not require Rho kinase inhibitor in order to remain attached to micro-carriers and to proliferate.

Figure 9:
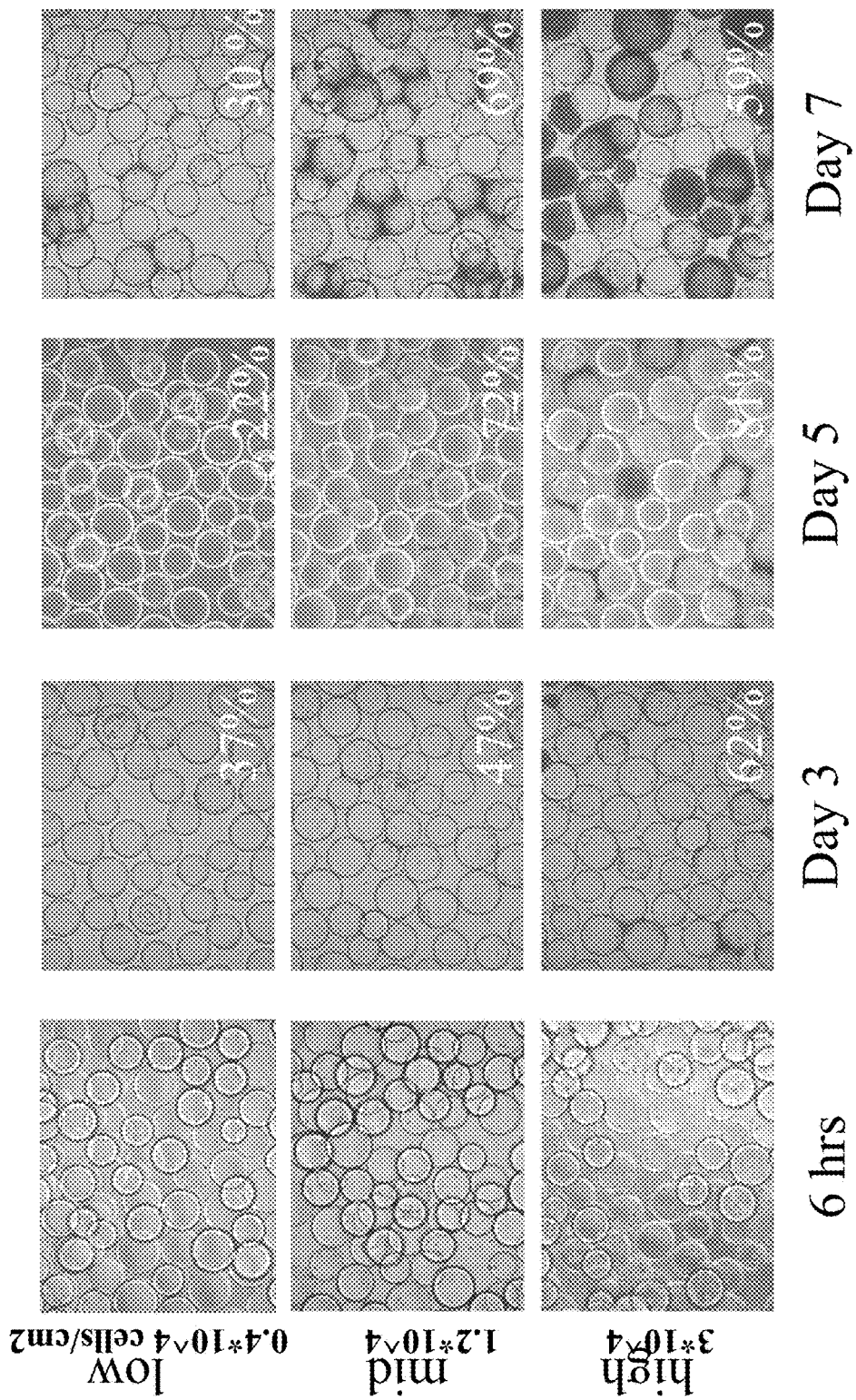
FIG. 9: Determination of cell attachment to micro-carriers at different seeding densities in spinner flasks. H1 cells were seeded onto Cytodex 3® (GE Healthcare Life Sciences, NJ) micro-carriers at the densities listed on the left; Low (0.4×10$^4$ cells/cm$^2$), Mid (1.2×10$^4$ cells/cm$^2$) or High (3×10$^4$ cells/cm$^2$). At 3, 5 and 7 days the cells were imaged and the percentage of micro-carriers with cells attached was determined (embedded in image).
Figure 10:
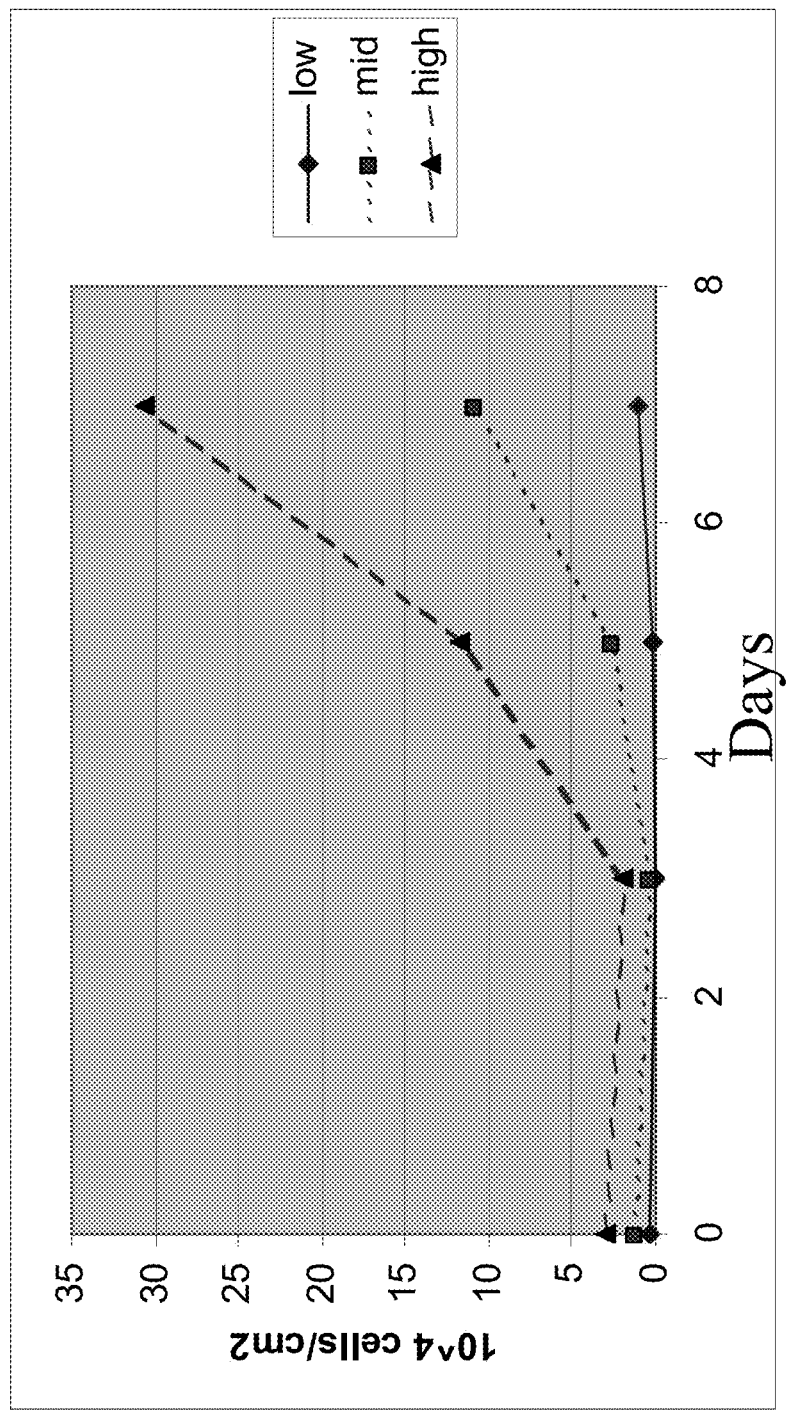
FIG. 10: Cell growth on micro-carriers in spinner flasks is affected by the initial seeding densities. H1 cells were seeded onto Cytodex 3® (GE Healthcare Life Sciences, NJ) micro-carriers at the densities listed on the left; Low (0.4×10$^4$ cells/cm$^2$), Mid (1.2×10$^4$ cells/cm$^2$) or High (3×10$^4$ cells/cm$^2$). At 3, 5 and 7 days the cells were dissociated from the micro-carriers and counted.
Figure 11:
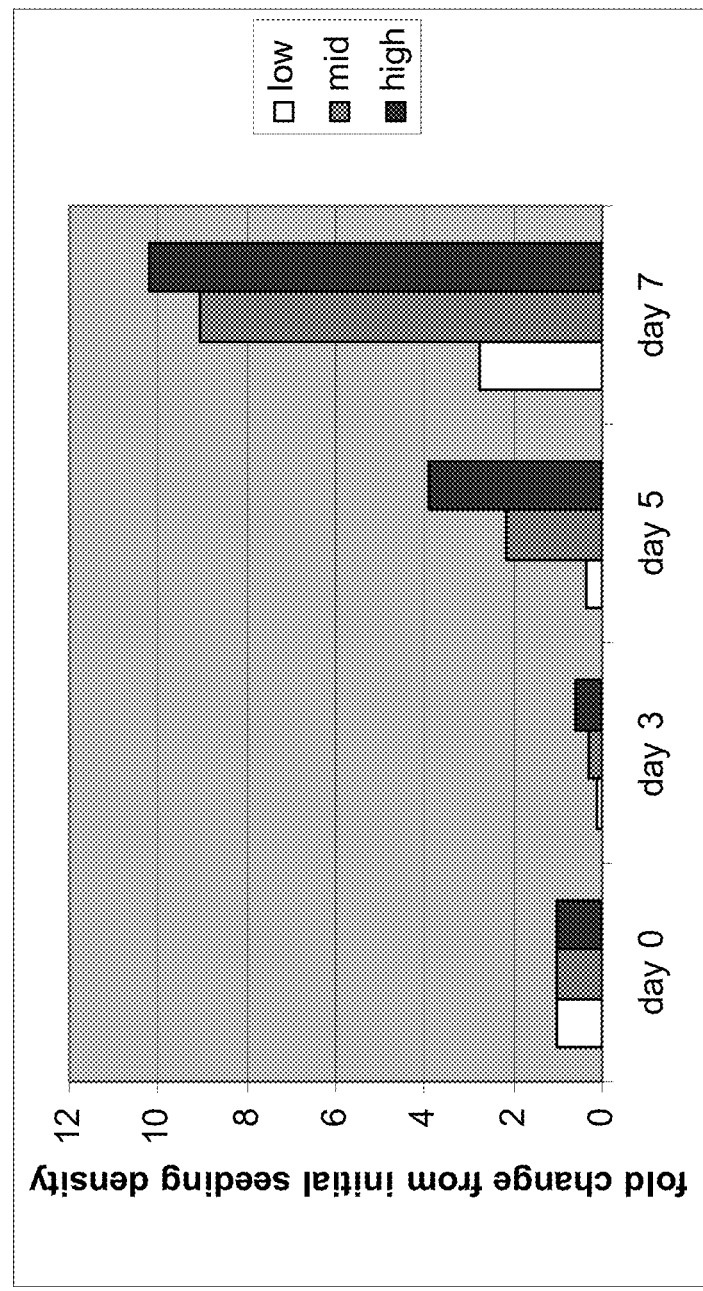
FIG. 11: Determination of cell growth rate on micro-carriers at different seeding densities in spinner flasks. H1 cells were seeded onto Cytodex 3® (GE Healthcare Life Sciences, NJ) micro-carriers at different densities (day 0); Low (0.4×10$^4$ cells/cm$^2$), Mid (1.2×10$^4$ cells/cm$^2$) or High (3×10$^4$ cells/cm$^2$). At 3, 5 and 7 days the cells were dissociated from the micro-carriers and counted. The fold increase in cell number is shown versus initial seeding density.

Example 3: Effect of Cell Density on Attachment and Growth on Micro-Carriers Improving the seeding density is a method to reduce the total number of cells needed. To determine the proper seeding density, the number of micro-carriers per 4× objective field was counted. H1 cells were seeded at $0.4 \times 10^4$ cells/cm² (low), $1.2 \times 10^4$ cells/cm² (mid), or $3 \times 10^4$ cells/cm² (high) densities into a 10 cm plate with Cytodex 3 micro-carriers (GE Healthcare Life Sciences, NJ) in MEF-CM plus 10 μM Y27632 (Sigma-Aldrich, MO). The plate was then agitated every 45 minutes for 6 hours at 37° C. The cells and micro carriers were transferred to a spinner flask (described in Example 5) at 37° C. at 30 rpm in 50 ml MEF-CM plus 10 μM Y27632 (Sigma-Aldrich, MO). After 24 hours 25 ml of MEFCM with 5 μM Y27632 (Sigma-Aldrich, MO) was added. After 24 hours the speed of rotation was increased to 40 rpm. On day 3 and 5 of culture, 50 ml of 75 ml was removed and replaced with MEF-CM. Images were taken of an aliquot from the spinner flasks at 6 hours, 3 days, 5 days and 7 days. The percentage of micro-carriers with cells attached is stated in the lower right corner in FIG. 9 images. At 3 days post seeding, the number of micro-carriers coated with cells corresponds to the original seeding density but at days 5 and 7 the number of micro-carriers coated with cells did not increase for the lower density seeded cells. This suggests that $0.4 \times 10^4$ cells/cm² is not a sufficient number of cells to allow incorporation of micro-carriers into the aggregates. At $3 \times 10^4$ cells/cm² the number of micro-carriers with cells attached is similar to $1.2 \times 10^4$ cells/cm² seeded at days 5 and 7 (FIG. 9). When looking at the cell number, it is clear that more cells are attached to micro-carriers from high density cell seeding (FIG. 10). Analysis of the fold change compared to the starting seeding cell number reveals a higher number of cells attached at 3 and 5 days in the high density seeded cultures (FIG. 11). By day 7, the control and high density seeded cultures have similar fold change in cell number from their starting seeding density. From these data, it is concluded that $1.2 \times 10^4$ cells/cm² is the minimum cell number for efficient attachment and growth of H1 cells on micro-carriers. Moving to higher seeding densities may aid in decreasing the number of days required for cell expansion.

Example 4: Dissociation of Cells From Micro-Carriers

Figure 12:
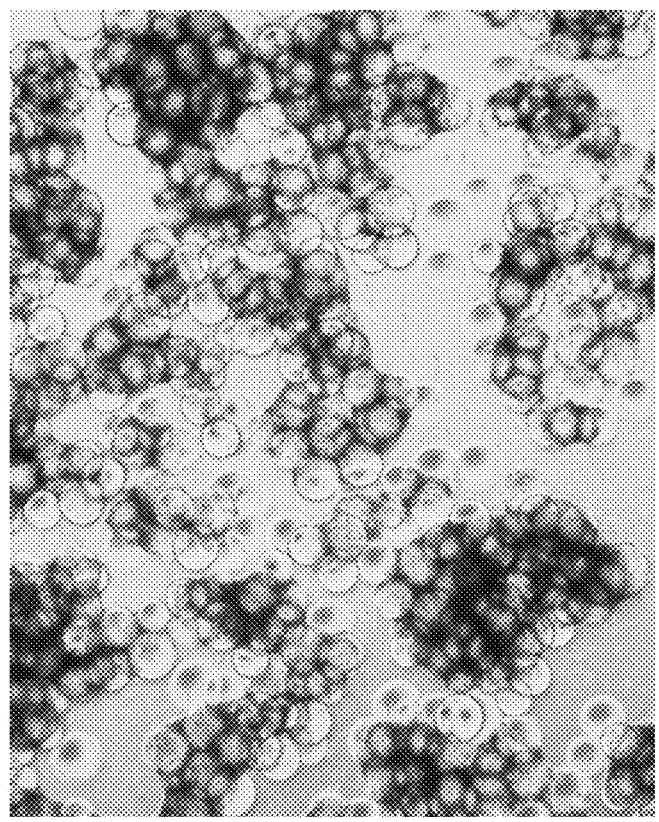
FIG. 12: H1 cells grown on Cytodex 3® micro-carriers (GE Healthcare Life Sciences, NJ) were imaged after 7 days in culture. The cells received MEF-CM without Rho kinase inhibitor from day 3 onward. The cells remained attached to the micro-carriers.
Figure 13:
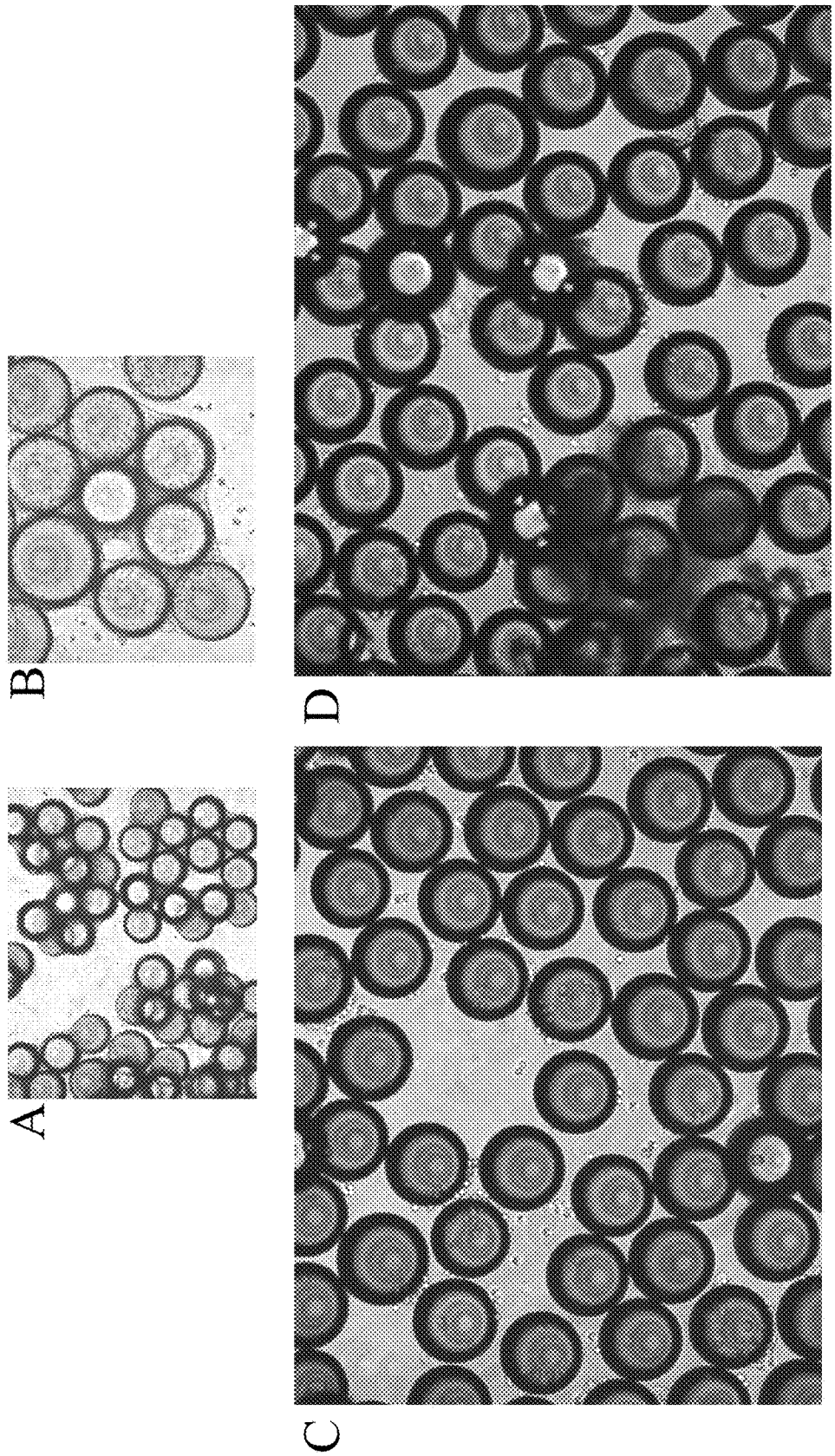
FIG. 13: H9 cells growth and dissociation of H9 cells on HILLEX®II micro-carriers (Solohill, MI). A, B 10× and 20× images of H9 cells grown for 6 days on HILLEX®II micro-carriers (Solohill, MI). C, 20× image of cells dissociated from HILLEX®II micro-carriers (Solohill, MI) for 10 minutes with 0.05% Trypsin/EDTA. D, 20× image of cells dissociated from HILLEX®II micro-carriers (Solohill, MI) for 10 minutes with TrypLE™ Express.
Figure 14:
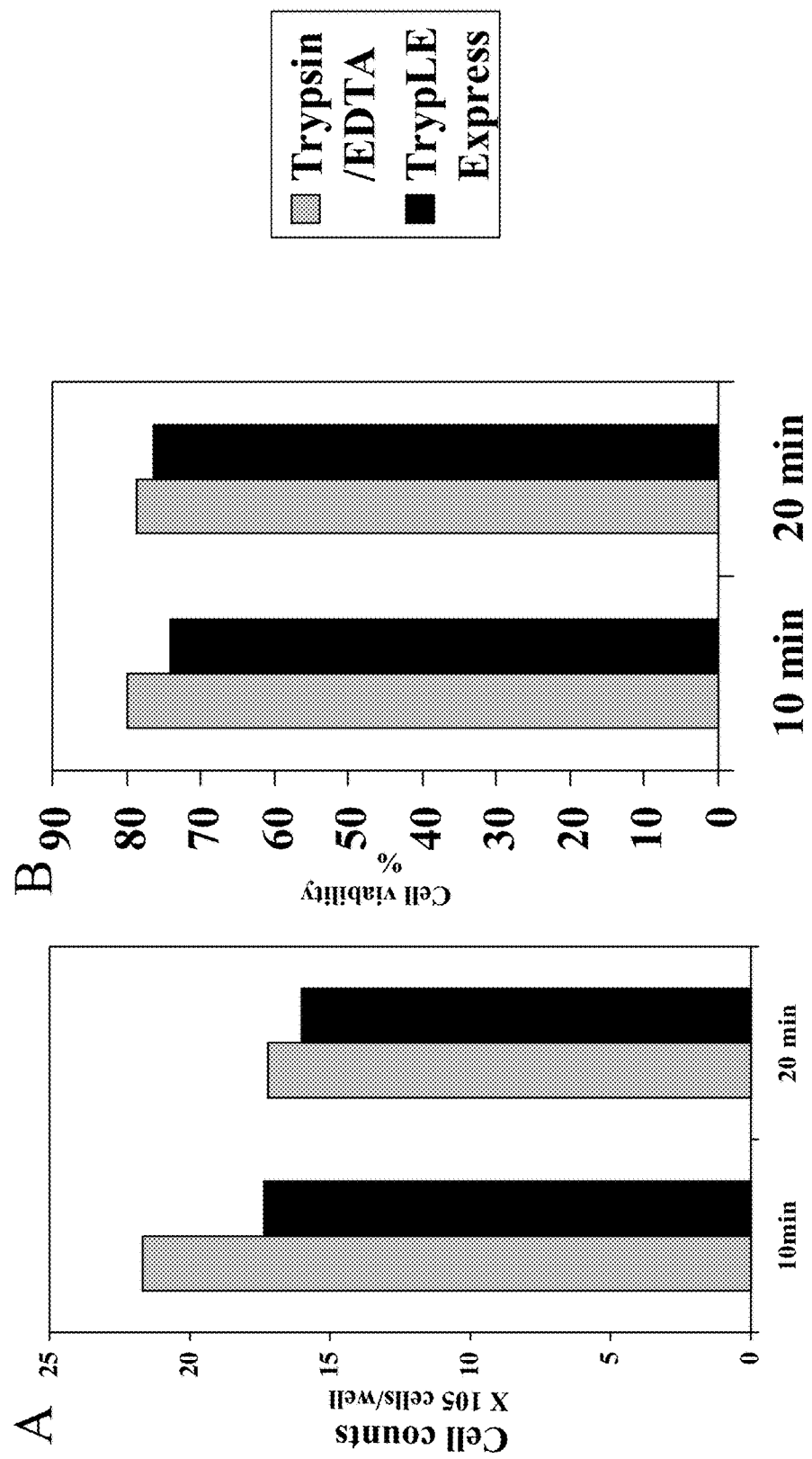
FIG. 14: Dissociation of H9 cells from micro-carriers. H9 cells grown on HILLEX®II (Solohill, MI) on a rocking platform, were dissociated with TrypLE™ Express or 0.05% Trypsin/EDTA. The number of cells and their viability is shown, A and B respectively.

In order to determine growth rates it was necessary to dissociate the cells from the micro-carriers. Removal of the Rho kinase inhibitor Y27632 (Sigma-Aldrich, MO) did not cause the H1 cells to dissociate from the micro-carriers (Example 2, FIG. 12). H9 cells on HILLEX®II micro-carriers (Solohill, MI) were imaged at 10× and 20× magnification before dissociation of the cells from the micro-carriers (FIG. 13A, B respectively). Enzymatic treatment of the H9 cells on HILLEX®II micro-carriers (Solohill, MI) allowed for detachment of viable cells (FIGS. 13C, D and 14). The H9 cells were grown for 6 days in a 6 well dish with HILLEX®II micro-carriers (Solohill, MI) on a rocking platform at 37° C. The cells attached to micro-carriers were placed in a 15 ml conical tube and the medium was aspirated after allowing the micro-carriers to settle. The settled micro-carriers were washed three times with 4 ml PBS (without magnesium and calcium ions) allowing the micro-carriers to settle by gravity sedimentation. The PBS was aspirated and 1 ml of PBS was added. The micro-carriers with cells were transferred into a single well of a 12 well non-tissue culture treated plate. The plate was allowed to rest at an angle to allow the micro-carriers to settle. The PBS was aspirated and 1 ml TrypLE™ Express (Invitrogen, CA) or 0.05% Trypsin/EDTA was added to the well. The plate was placed at 37° C. on the rocking platform for 10 or 20 minutes. The plate was removed and 3 ml DMEM/F12 or MEF-CM was added to the well. The medium was vigorously pipetted, releasing the cells (FIG. 13C, D). Observation of the micro-carriers under a microscope determined detachment of the cells from the micro-carriers. The cells were then centrifuged at 200× g for 5 minutes. The medium was aspirated and the pellet was resuspended in 1 ml DMEM/F12 or MEF-CM medium. The cells were then counted on a Guava PCA-96 (Guava Technologies, Hayward, Calif.) with Viacount dye. Specifically, a 200 µl volume of cells in appropriate dilution of medium, was incubated with 2 µl of Viacount for 10 minutes. The viability and cell number were determined (FIG. 14). Both TrypLE™ Express and Trypsin/EDTA dissociated the cells effectively from micro-carriers.

Figure 15:
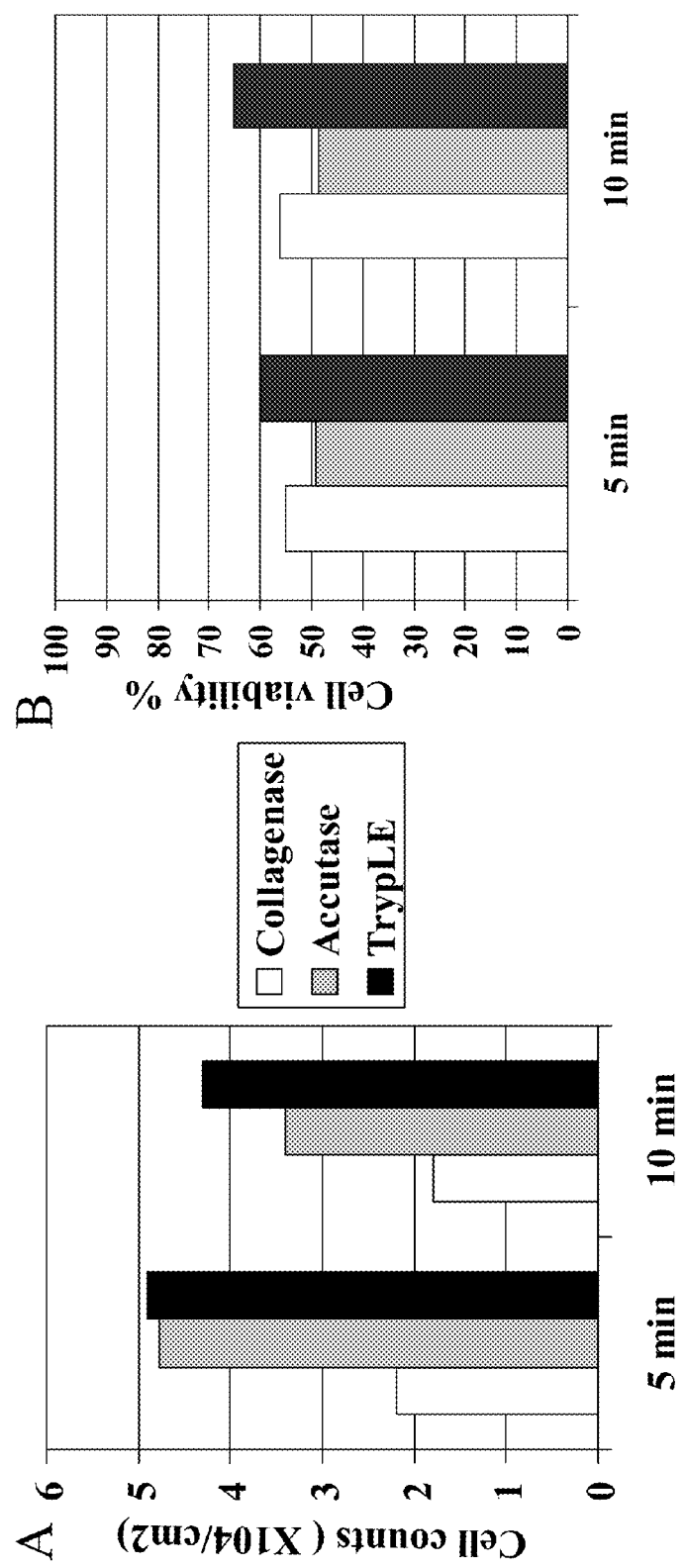
FIG. 15: Dissociation of H1 cells from micro-carriers. H1 cells grown on Cytodex 3® (GE Healthcare Life Sciences, NJ) in a spinner flask were dissociated with TrypLE™ Express (Invitrogen, CA), Accutase™ or Collagenase (10 mg/ml). The number of cells and their viability is shown, A and B respectively.

Since TrypLE™ Express released the cells from the micro-carriers and is available as a GMP product, it was tested against other possible dissociation agents, specifically Collagenase and Accutase™ (Sigma-Aldrich, MO). H1p48 cells were grown in a spinner flask (Example 5) for 10 days. The micro-carriers were then collected and transferred to a 50 ml conical tube. The cells were washed in PBS as above and transferred to a 12 well plate. PBS was aspirated and 1 ml of TrypLE™ Express, Accutase™ or Collagenase (10 mg/ml) was added to the well and placed on a rocking platform at 37° C. for 5 or 10 minutes. The cells/micro-carriers were vigorously resuspended in DMEM/F12, and then the dissociated cells and micro-carriers were passed through a 40 µm cell strainer over a 50 ml conical tube. The well was washed with an additional 2 ml medium, also added to the strainer before centrifuging at 200× g for 5 minutes. The cells were then resuspended in 1 ml DMEM/F12 and diluted for cell counting, as above. Cell viability was similar with all tested enzymes. Accutase™ and TrypLE™ Express released similar cell numbers over 5 and 10 minute incubations (FIG. 15). This illustrates the suitability of Accutase™ and TrypLE™ Express as cell dissociation regents for human embryonic stem cells on micro-carriers.

Figure 16:
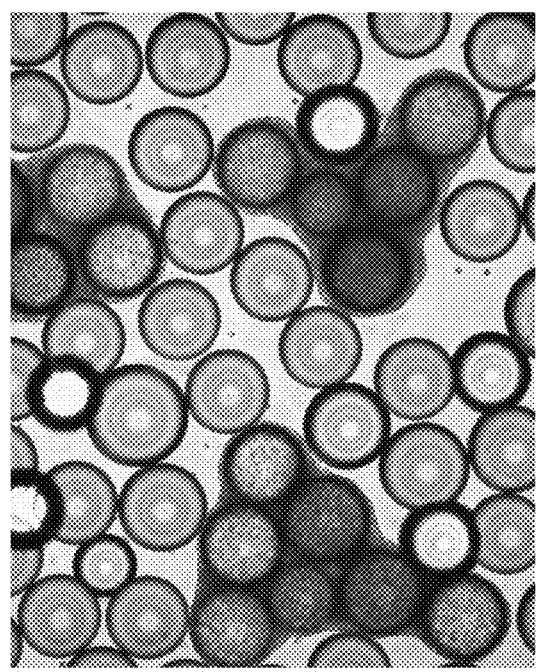
FIG. 16: H9 cells grown on HILLEX®II (Solohill, MI) micro-carriers do not transfer between micro-carriers.

Example 5: Propagation of Undifferentiated Pluripotent Stem Cells on Micro-Carriers In order to expand cells on micro-carriers, cells must be able to detach or be enzymatically dissociated from the micro-carriers and reattach to new micro-carriers. Typical methods of cell propagation on micro-carriers rely on the property of cells to detach and reattach. The following experiment showed that this was not a characteristic of human embryonic stem cells. Specifically, H9 p43 cells were seeded onto HILLEX®II micro-carriers (Solohill, MI) and incubated in a 125 ml spinner flask (see below). Phenol red present in the medium and was taken up by the HILLEX®II micro-carriers (Solohill, MI). After 8 days of growth, a 10 ml aliquot of the cells on micro-carriers was placed in a new spinner flask containing phenol red-free MEF-CM, 440 mg of HILLEX®II micro-carriers, and 5 µM Y27632 (Sigma-Aldrich, MO). After 5 days incubation at 37° C. with 30 rpm rotation, the micro-carriers were removed and images were acquired (FIG. 16). The dark micro-carriers shown are the micro-carriers covered with H9 cells grown in medium containing phenol red. The light micro-carriers are the newly added micro-carriers. It was expected that the H9 cells would detach and reattach to new micro-carriers, however, instead the cells formed aggregates with the new micro-carriers. No light micro-carriers had cells attached that are not also in aggregates with the dark micro-carriers, suggesting that the cells were not able to detach and reattach to micro-carriers. In order to propagate cells grown on micro-carriers, the cells must be enzymatically dissociated from the micro-carriers (see Example 4).

Figure 17:
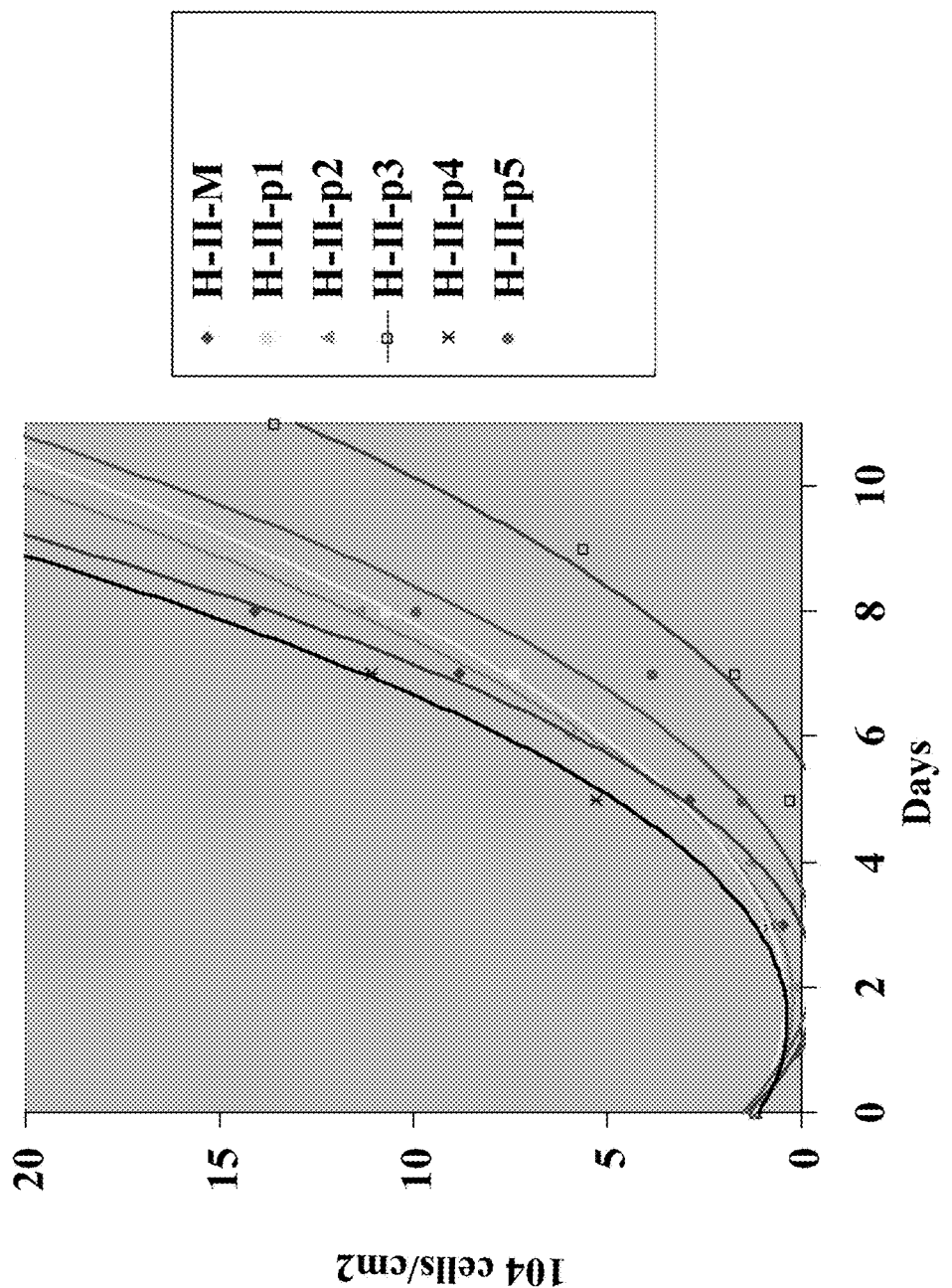
FIG. 17: H9 at passage 43 were grown for 5 passages on HILLEX®II (Solohill, MI) micro-carriers in a spinner flask. Cells were counted every 2 to 3 days and passaged when cells reached 1-2×10$^5$ cells/cm$^2$.
Figure 18:
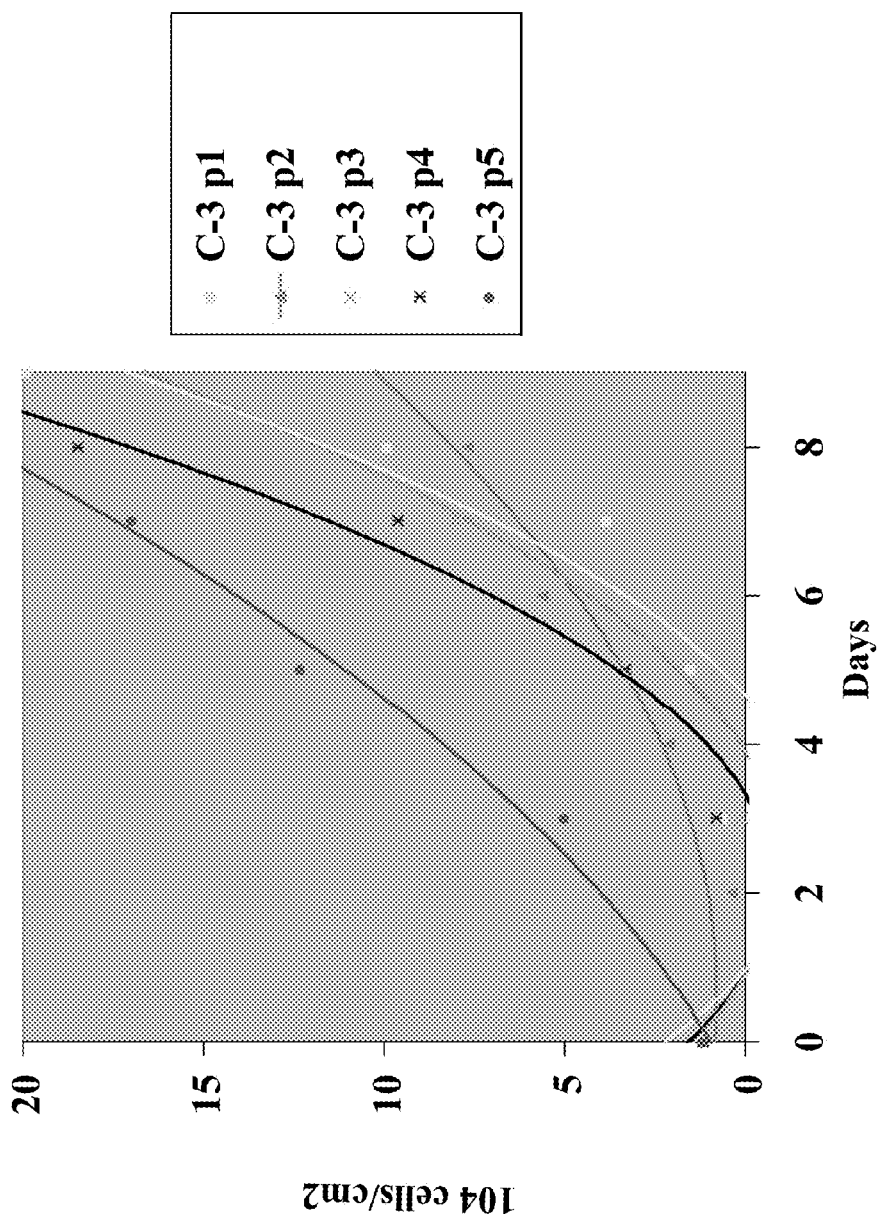
FIG. 18: H9 cells at passage 43 were grown for 5 passages on Cytodex 3® micro-carriers (GE Healthcare Life Sciences, NJ) in a spinner flask. Cells were counted every 2 to 3 days and passaged when cells reached 1-2×10$^5$ cells/cm$^2$.
Figure 19:
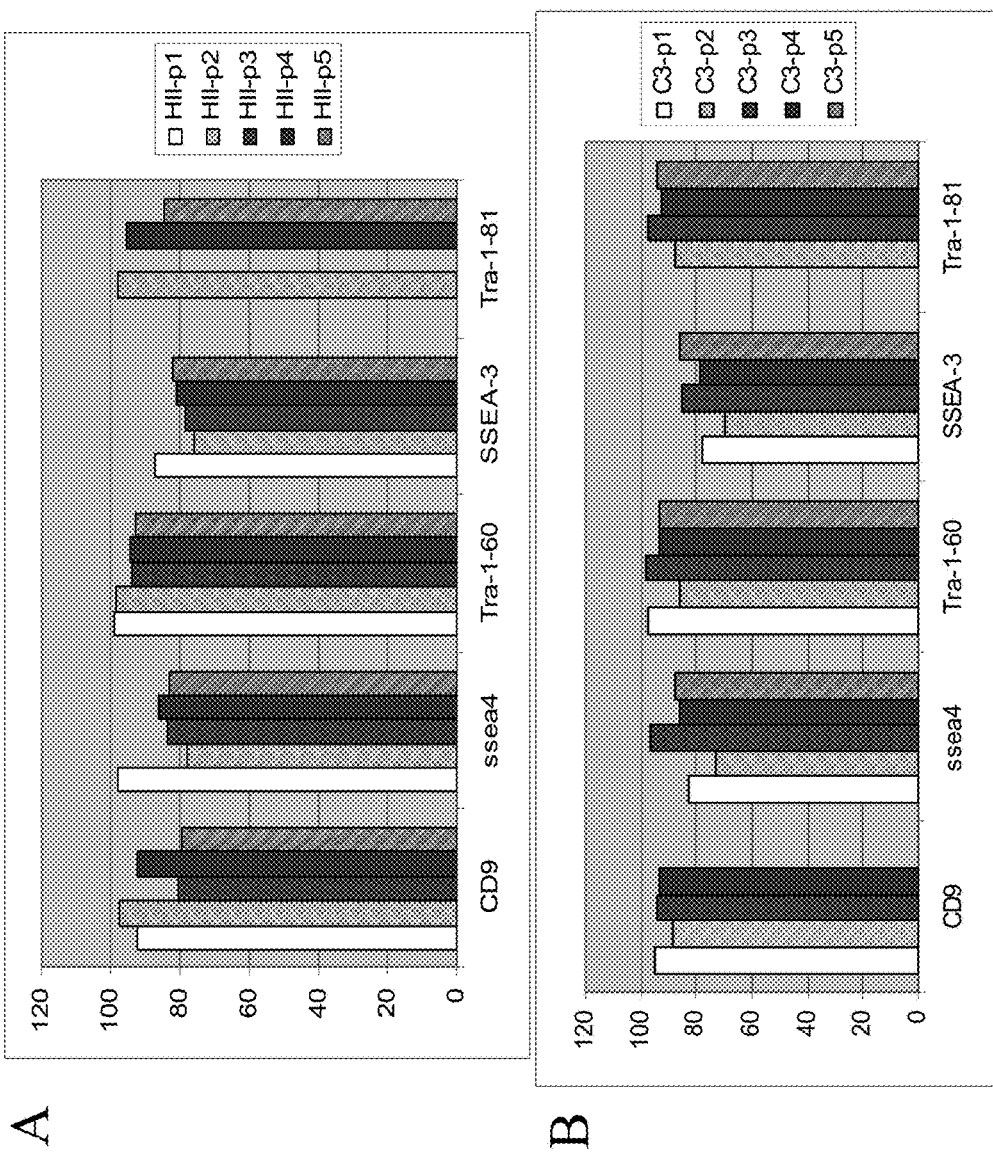
FIG. 19: Fluorescent-activated cell sorting (FACS) shows pluripotency of H9 cells grown in spinner flasks. A, The majority of H9 p43 cells grown on HILLEX®II (Solohill, MI) micro-carriers express of pluripotency proteins. Passage 1 and 3 cells were not evaluated for TRA-1-81. B, The majority of H9 p43 cells grown on Cytodex 3® (GE Healthcare Life Sciences, NJ) micro-carriers express of pluripotency proteins. Passage 1 cells were not evaluated for TRA-1-81.

Since it is now established how human embryonic stem cells can be propagated on micro-carriers it needs to be determined how human embryonic stem cells propagate in larger scale spinner flasks. Spinner flasks allow the expansion of cells in high-density systems. This is space conserving and is considered the first step to expanding cells in bioreactors. To test the ability of human embryonic stem cells to proliferate in spinner flasks, H9 passage 43 cells were seeded into 125 ml spinner flasks. Cells were initially attached to the micro-carriers in a 10 cm plate before transferring to the spinner flask. Specifically, H9 cells were released from the two six-well dishes by a five minute incubation with TrypLE™ Express at 37° C. Prior to passaging with TrypLE™ Express the cells had been passaged with Collagenase (1 mg/ml) and seeded onto 1:30 Growth Factor Reduced MATRIGEL™ (BD Biosciences, CA) coated plates. The cells were resuspended in DMEM/F12 and counted on a Guava instrument with Viacount. After centrifugation, $3 \times 10^6$ cells were seeded into a 10 cm plate containing MEF-CM plus 10 µM Y27632 (Sigma-Aldrich, MO) and 250 $cm^2$ of HILLEX® II micro-carriers (Solohill, MI), prepared according to the manufacturer's instructions. The dish was placed at 37° C. and gently rotated and agitated once every 45 minutes for 4.5 hours. Then the cells, micro-carriers and medium were transferred to a 125 ml spinner flask. The spinner flask was then filled to 50 ml with MEF-CM plus 10 µM Y27632 (Sigma-Aldrich, MO) and placed on a stir plate at 37° C. at 40 rpm. The following day the medium was changed and filled to 75 ml with MEF-CM plus 5 µM Y27632 (Sigma-Aldrich, MO). The rate of stirring was increased to 70 rpm. Medium was changed every other day without addition of Y27632 compound (Sigma-Aldrich, MO). The cells were passaged according to the methods disclosed in Example 4, and $3 \times 10^6$ cells were reseeded onto 250 $cm^2$ of new micro-carriers. The cultures were passaged when they reached a confluence of $1-2 \times 10^5$ cells/$cm^2$. This was conducted for 5 passages (FIG. 17). At each passage pluripotent marker expression was evaluated showing 80-95% of cells expressed the pluripotency markers CD9, SSEA4, SSEA3, TRA-1-60 and TRA-1-81 (FIG. 19A). A similar experiment was conducted with H9 p43 cells on Cytodex 3® micro-carriers ((GE Healthcare Life Sciences, NJ), FIGS. 18, 19B). Overall, the cells proliferated well on both HILLEX®II (Solohill, MI) and Cytodex 3® (GE Healthcare Life Sciences, NJ) micro-carriers and remained pluripotent. Karyotypic analysis was conducted after 5 passages in spinner flasks and showed an abnormal trisomy in chromosome 12 in 1.5% of the cells. Since these cells were nearing passage 50 at the conclusion of the experiment, it may be a common occurrence to observe such abnormalities. Beginning with a lower cell passage number may allow this premise to be tested.

Figure 20:
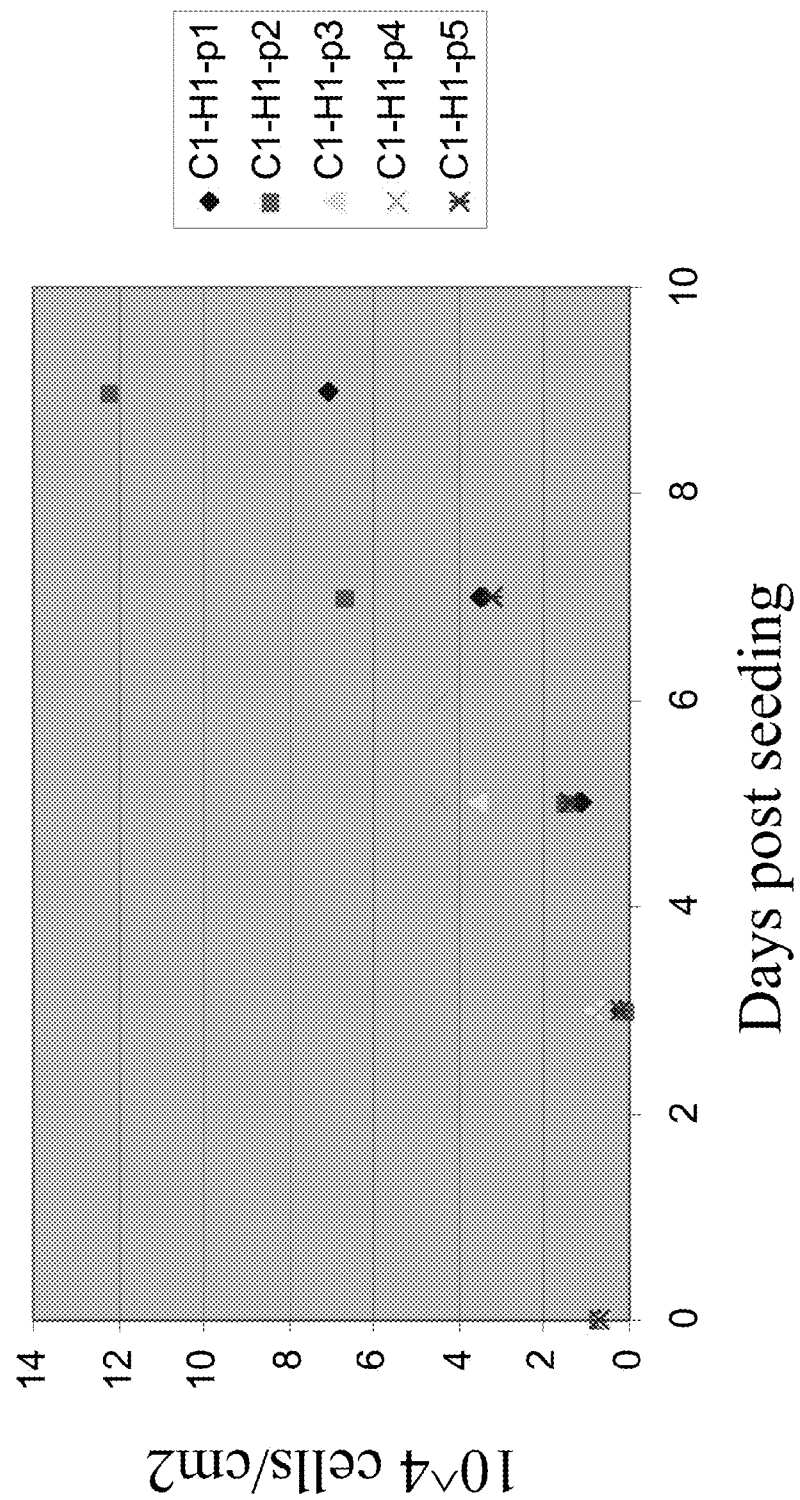
FIG. 20: H1p49 cells were grown for 5 passages on Cytodex 1® micro-carriers (GE Healthcare Life Sciences, NJ) in a spinner flask. Cells were counted every 2 to 3 days and passaged when cells reached 4-8×10$^4$ cells/cm$^2$.
Figure 21:
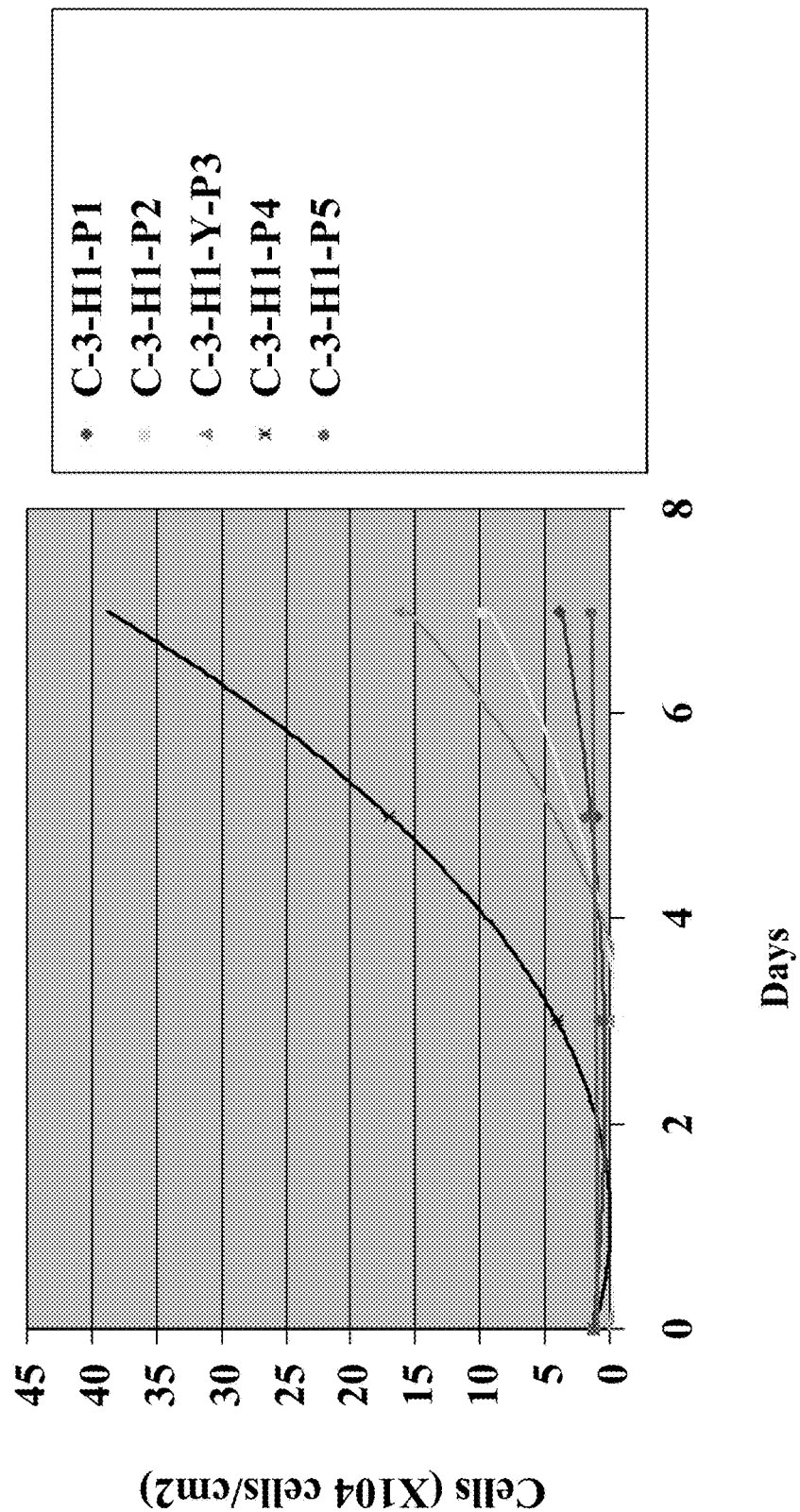
FIG. 21: H1 cells at passage 49 were grown for 5 passages on Cytodex 3® micro-carriers (GE Healthcare Life Sciences, NJ) in a spinner flask. Cells were counted every 2 to 3 days and passaged when cells reached 1-2×10$^5$ cells/cm$^2$.
Figure 22:
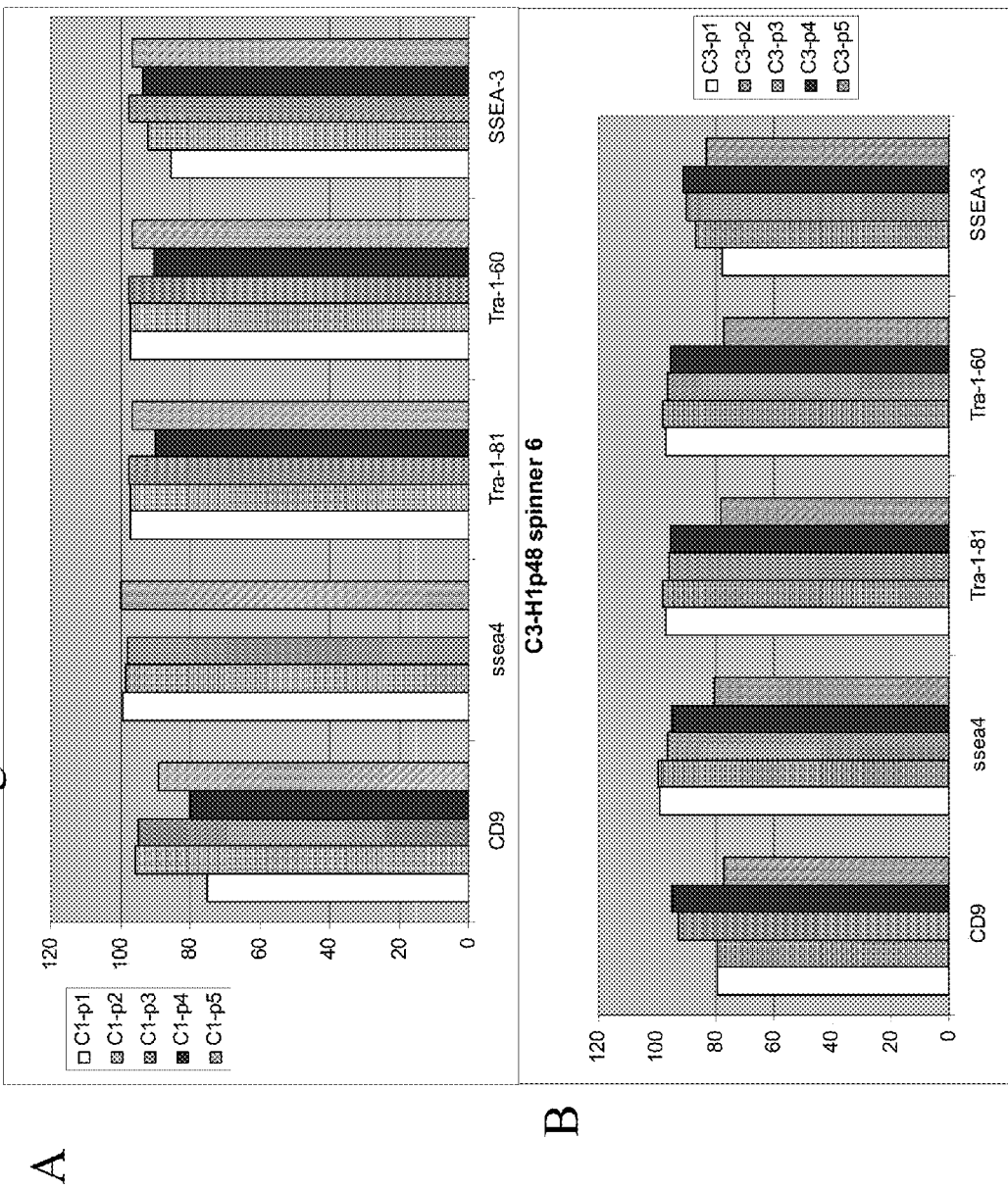
FIG. 22: Fluorescence activated cell sorting (FACS) shows pluripotency of H1 cells grown in spinner flasks.
Figure 23:
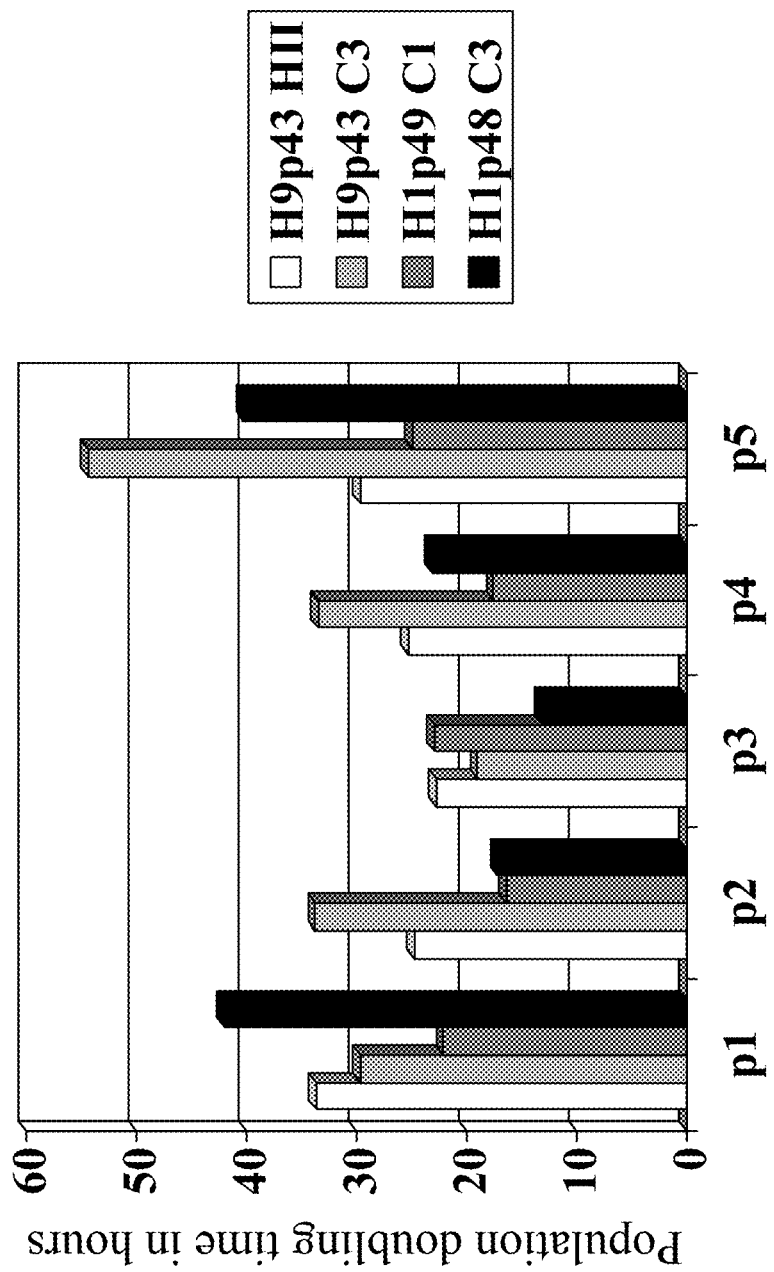
FIG. 23: Population doublings of H1 and H9 cells on micro-carriers. Population doubling times were calculated from day 3 to the day of passaging (day 5, 6 or 7).

Similar experiments were conducted with the H1 line at p48 and p49. All parameters remained the same except the rotation speed and seeding density. The rotation speed for the spinner flask was 30 rpm over-night on day 1 and increased to 40 rpm for all additional days. The seeding density for Cytodex 3® micro-carriers (GE Healthcare Life Sciences, NJ) was about 11,000 cells/$cm^2$ while the seeding density for Cytodex 1® micro-carriers (GE Healthcare Life Sciences, NJ) was about 7,000 cells/$cm^2$. The cell number seeded was held constant at $3 \times 10^6$ cells per spinner flask. The weight of micro-carriers was held constant at 100 mg for Cytodex 1® and Cytodex 3®. One advantage of Cytodex 1® and Cytodex 3® over HILLEX®II micro-carriers is their larger surface area. FIGS. 20 and 21 show the expansion of H1 cells on Cytodex 1® and Cytodex 3® respectively. The cells remained pluripotent over the five passages (FIG. 22). Karyotype analysis of H1 cells on Cytodex 3® microcarriers revealed duplication of the Y chromosome in 10% of the cells tested. These H1 cells were passaged onto micro-carriers at p48 and were analyzed 5 passages later. H1p55 cells grown on MATRIGEL™ (BD Biosciences, CA) on a planar surface had a normal karyotype. Analysis of the doubling rates for these cells between day 3 and the day of passaging (day 5, 6 or7) showed no overall change in doubling times (FIG. 23). H1 cells grown on Cytodex 1® micro-carriers and H9 grown on HILLEX®II micro-carriers (Solohill, MI) showed the most consistent doubling times (Table 3).

Figure 24:
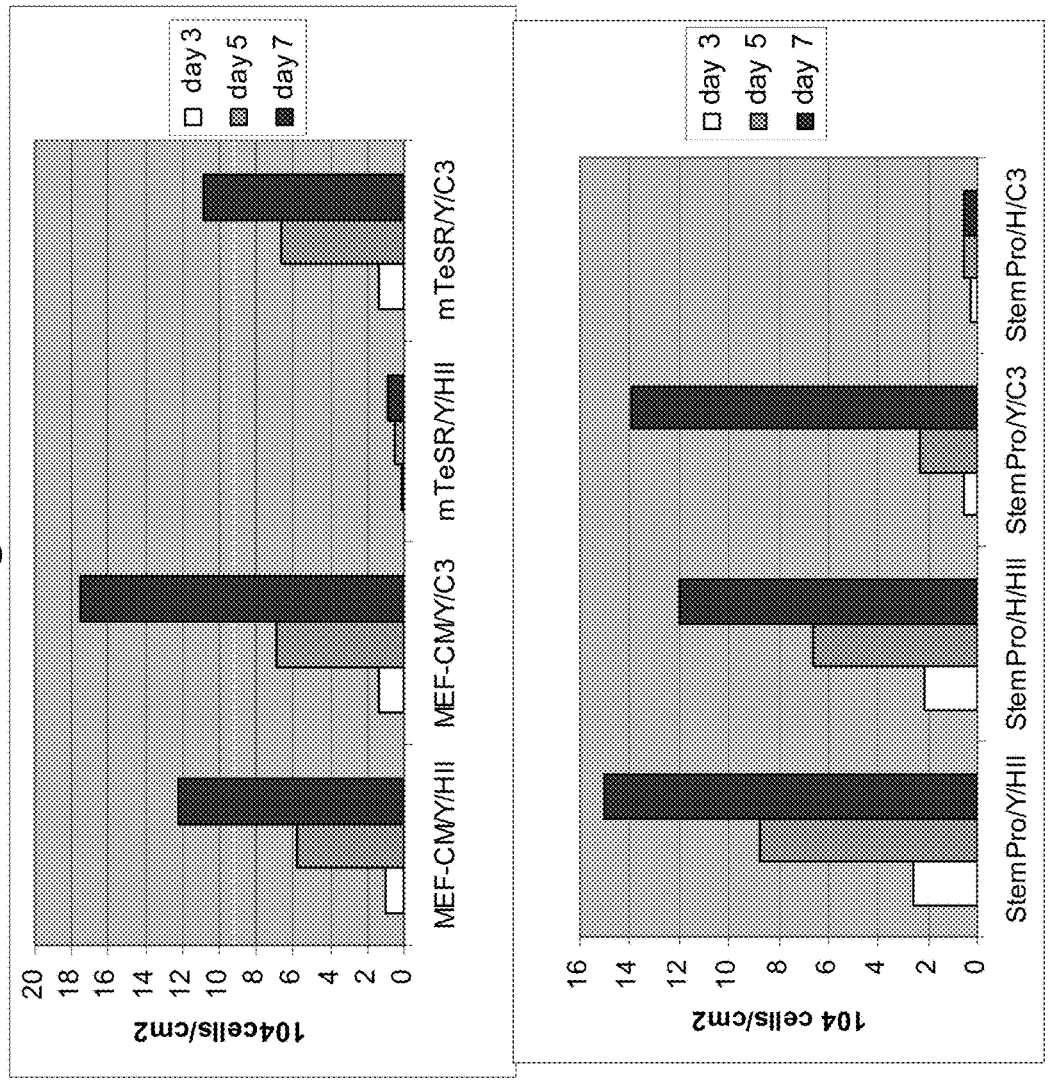
FIG. 24: H9 cells cultured on micro-carriers in defined media. The cells were cultured on HILLEX®II (HII, (Solohill, MI)) or Cytodex 3® (C3, (GE Healthcare Life Sciences, NJ)). Cells were cultured on micro-carriers in one of the following media; mTESR (StemCell Technologies, Vancouver, Canada), StemPro or MEF-CM. 10 µM Y27632 (Y, (Sigma-Aldrich, MO)) or 2.5 µM Glycyl-H 1152 dihydrochloride (H, (Tocris, MO)) was added to the media. Growth rate at 3, 5 and 7 days post seeding was determined.

Example 6: Proliferation of Human Embryonic Stem Cells on Micro-Carriers in Defined Medium To manufacture a therapeutic product, it is desirable to remove any animal components from the human embryonic stem cell culture medium. Currently human embryonic stem cells are maintained on MATRIGEL™ (BD Biosciences, CA) in medium conditioned using mouse embryonic fibroblasts (MEF-CM). Both MATRIGEL™ (BD Biosciences, CA) and MEF-CM are derived from mouse cells. Additionally, MEF-CM is an expensive and time-consuming medium to generate. To determine if human embryonic stem cells can be sustained on micro-carriers with defined medium, H9 cells were seeded onto Cytodex 3® (GE Healthcare Life Sciences, NJ) and HILLEX®II (Solohill, MI) micro-carriers in the presence of Rho kinase inhibitors, 10 µM Y27632 (Sigma-Aldrich, MO) or 2.5 µM Glycyl-H 1152 dihydrochloride (Tocris, MO) in Stem Pro (Invitrogen, CA), mTESR (StemCell Technologies, Vancouver, Canada) or MEF-CM. The cells were placed in a 12 well dish on a rocking platform at 37° C. The cells were counted at days 3, 5 and 7. H9 p39 cells grown in MEF-CM on both bead types showed typical expansion characteristics (FIG. 24). Similar cells grown in mTESR (StemCell Technologies, Vancouver, Canada) proliferated well on Cytodex 3® micro-carriers in the presence of 10 µM Y27632 (Sigma-Aldrich, MO) but exhibited a slow growth rate on HILLEX®II micro-carriers. Cells of the human embryonic stem cell line H9 at passage 64 (H9 p64) cells that had been acclimated to StemPro medium for over 20 passages proliferated well on both HILLEX®II and Cytodex 3® in the presence of 10 µM Y27632 (Sigma-Aldrich, MO). Surprisingly, these cells did not proliferate well in the presence of 2.5 µM Glycyl-H 1152 dihydrochloride (Tocris, MO) on Cytodex 3® micro-carriers. Therefore the micro-carrier type, Rho kinase inhibitor, and medium all play a role in determining the ability of human embryonic stem cells to proliferate.

Figure 25:
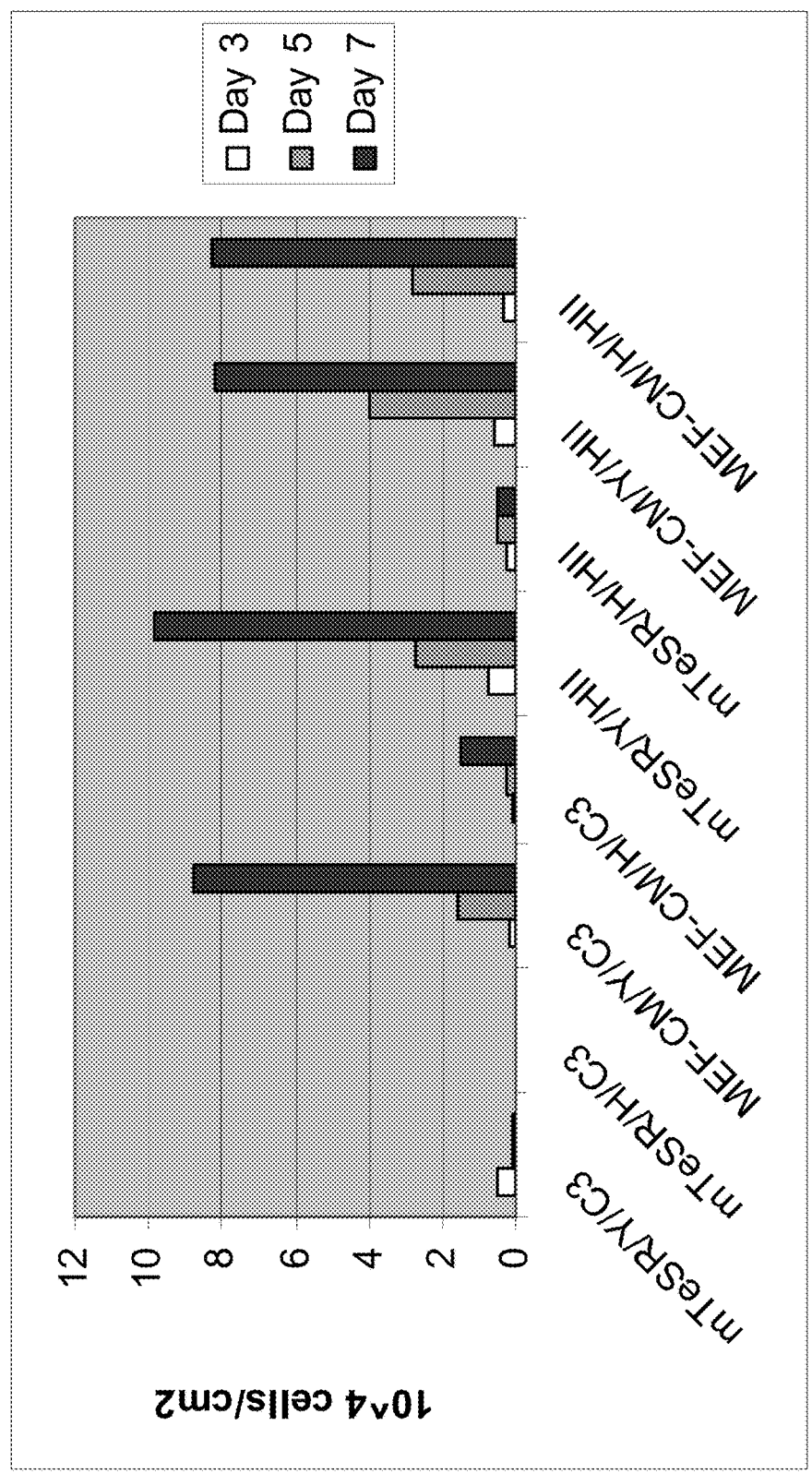
FIG. 25: H1 cells at passage 38 were cultured on micro-carriers in defined media. The cells were cultured on HILLEX®II (HII, (Solohill, MI)) or Cytodex 3® (C3, (GE Healthcare Life Sciences, NJ)) micro-carriers. Cells were cultured on micro-carriers in one of the following medias; mTESR (StemCell Technologies, Vancouver, Canada), StemPro and MEF-CM. 10 µM Y27632 (Y, (Sigma-Aldrich, MO)) or 2.5 µM Glycyl-H 1152 dihydrochloride (H, (Tocris, MO)) was added to the media. Growth rate at 3, 5 and 7 days post seeding was determined.

H1 human embryonic stem cells at passage 38 were seeded onto either Cytodex 3® or HILLEX®II micro-carriers in the presence of Rho kinase inhibitors, 10 µM Y27632 (Sigma-Aldrich, MO) or 2.5 µM Glycyl-H 1152 dihydrochloride in mTESR (StemCell Technologies, Vancouver, Canada) or MEF-CM in a 12 well dish. The cells were placed on a rocking platform at 37° C. The cells were counted at days 3, 5 and 7. Cells grown in MEF-CM on both micro-carrier types showed typical expansion characteristics in the presence of Y27632 (Sigma-Aldrich, MO) but exhibited poor growth with Glycyl-H 1152 dihydrochloride (Tocris, MO) on Cytodex 3® (FIG. 25). mTESR medium (StemCell Technologies, Vancouver, Canada) allowed the H1 cells to proliferate on HILLEX®II micro-carriers in the presence of both Rho kinase inhibitors but exhibited low growth rate on Cytodex 3® micro-carriers.

Figure 26:
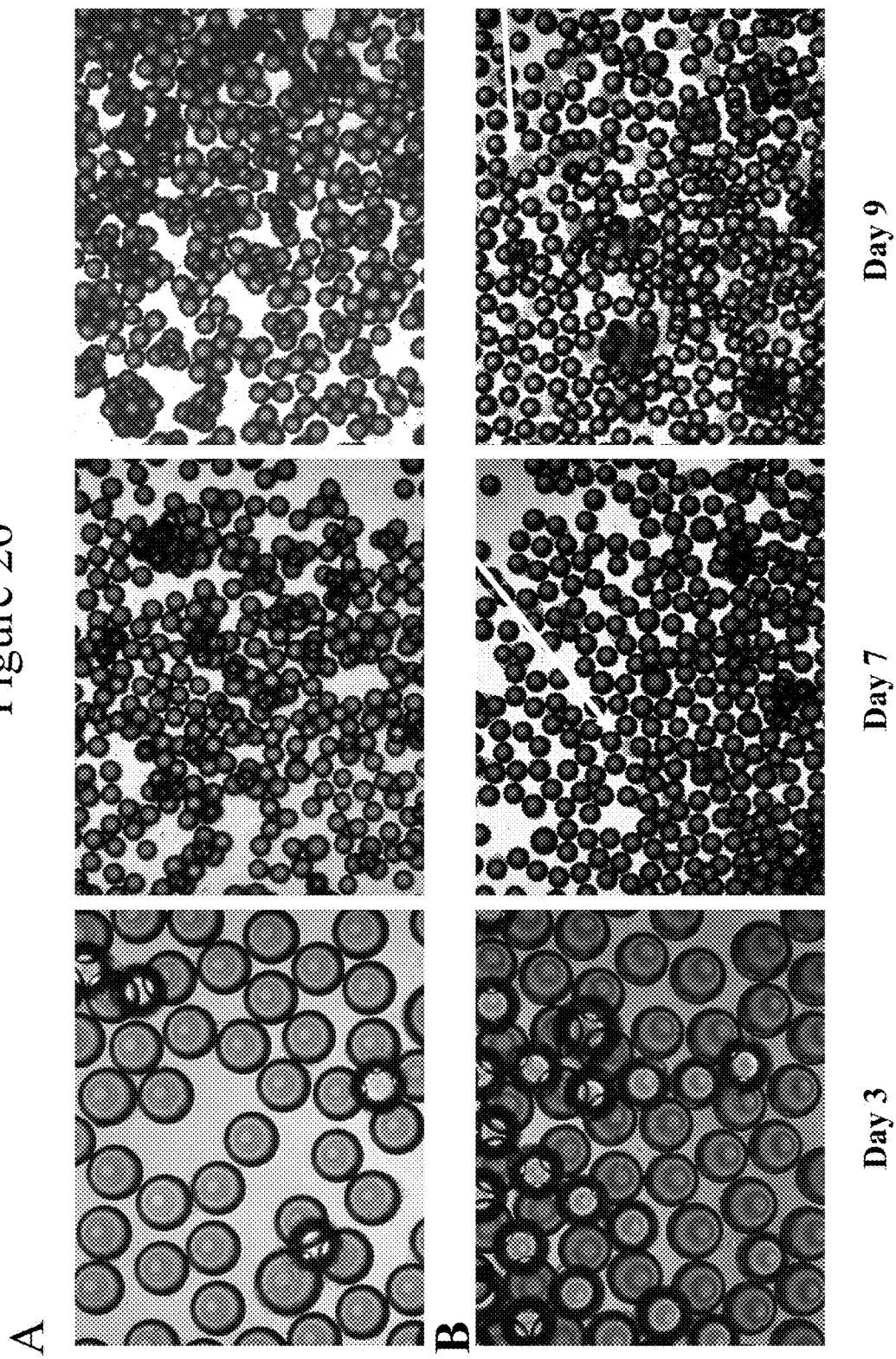
FIG. 26: H1 cells at passage 50 were cultured on HILLEX®II (Solohill, MI)) micro-carriers with defined medium in a spinner flask. A, Images of H1p50 cells grown in MEF-CM after 3, 7, or 9 days in a spinner flask. B, Images of H1p50 cells grown in mTESR (StemCell Technologies, Vancouver, Canada) after 3, 7, or 9 days. Arrows identify cell clusters not attached to the micro-carriers.

Given that H1p50 cells proliferated well in mTESR (StemCell Technologies, Vancouver, Canada) on HILLEX®II micro-carriers, $3\times10^6$ cells were seeded onto 250 cm$^2$ HILLEX®II micro-carriers. Cells were incubated at 37° C. in a 10 cm$^2$ dish for 5 hours with agitation by hand every 45 minutes. mTESR (StemCell Technologies, Vancouver, Canada) plus 10 µM Y27632 (Sigma-Aldrich, MO) was changed every other day. This was conducted in parallel with cells grown in MEF-CM (Example 5). Unlike cells grown in MEF-CM, the cells grown in mTESR medium (StemCell Technologies, Vancouver, Canada) began to detach from the HILLEX®II micro-carriers after 7 days (FIG. 26A vs. 26B). This indicates that additional supplements needed to be added to mTESR (StemCell Technologies, Vancouver, Canada) in order for the human embryonic stem cells to remain attached and proliferate on HILLEX®II micro-carriers (Solohill, MI).

Example 7: Differentiation of Human Embryonic Stem Cells on Micro-Carriers

Figure 27:
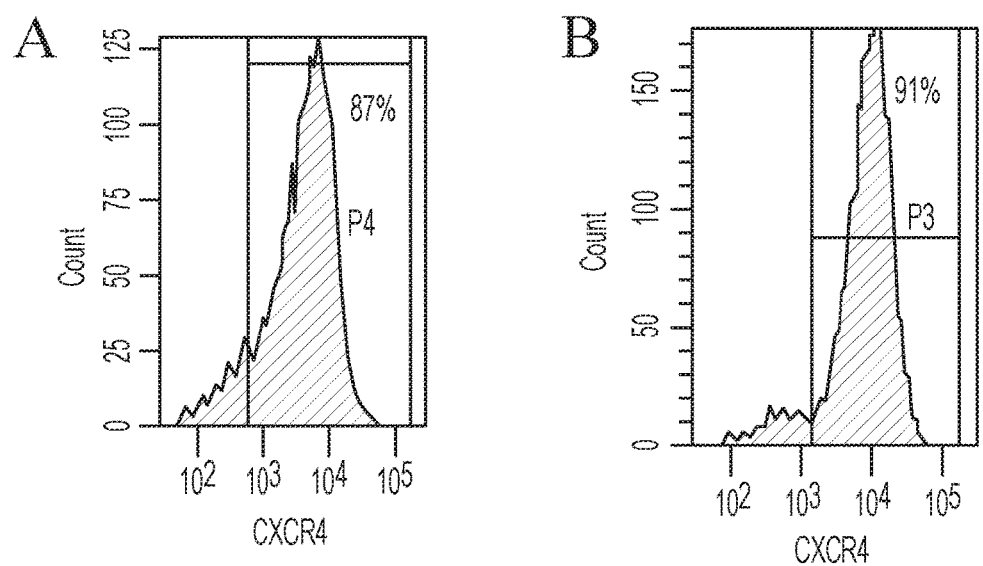
FIG. 27: Differentiation of human embryonic stem cells passaged five times in spinner flasks. A, H9 cells at passage 43 were passaged five times on Cytodex 3® micro-carriers (GE Healthcare Life Sciences, NJ). B, H1 cells at passage 49 were passaged five times on Cytodex 1® micro-carriers (GE Healthcare Life Sciences, NJ). Both cell types were released from the micro-carriers and seeded onto MATRIGEL (BD Biosciences, CA) coated plates. At 80-90% confluency the cells were exposed to a protocol that is capable of differentiating embryonic stem cells to definitive endoderm. The cells were then analyzed by FACS for the percentage of cells expressing CXCR4, a definitive endoderm marker. The percent of CXCR4 positive cells is in the upper right corner of the plot.

Since the human embryonic stem cells can be expanded on micro-carriers, the differentiation potential of these cells must be determined. Cells of the human embryonic stem cell line H9 at passage 43 were passaged five times on Cytodex 3® micro-carriers (GE Healthcare Life Sciences, NJ). At passage 5, the cells were grown for 6 days on the micro-carriers before being dissociated from the micro-carriers with TrypLE™ Express (see Example 4). The cells were then plated on 1:30 MATRIGEL™: DMEM/F12 coated plates. After the cells became 80 to 90% confluent on the plates they were exposed to differentiating agents. Differentiation of the human embryonic stem cells to definitive endoderm was conducted by treating the cells for 2 days with 2% Albumin Bovine Fraction V Fatty Acid Free (FAF BSA, MP Biomedicals, Ohio) in RPMI plus 100 ng/ml Activin A (PeproTech, NJ), 20 ng/ml Wnt3a (R&D Biosciences, MN) and 8 ng/ml bFGF (PeproTech, NJ). The cells were treated for an additional 2 days in 2% FAF BSA in RPMI plus 100 ng/ml Activin A (PeproTech, NJ) and 8 ng/ml bFGF (PeproTech, NJ). Medium was changed daily. FACS analysis conducted for the definitive endoderm cell surface marker CXCR4, showed that 87% of the cells expressed the protein (FIG. 27A). A similar experiment was conducted with cells of the human embryonic stem cell line H1 at passage 49 grown on Cytodex 1® micro-carriers (GE Healthcare Life Sciences, NJ) for 5 passages, revealing that 91% of the cells differentiated on the micro-carriers expressed CXCR4 (FIG. 27B). This demonstrates that the cells grown on micro-carriers are capable of differentiating into definitive endoderm, the first step to becoming insulin-producing cells.

Figure 28:
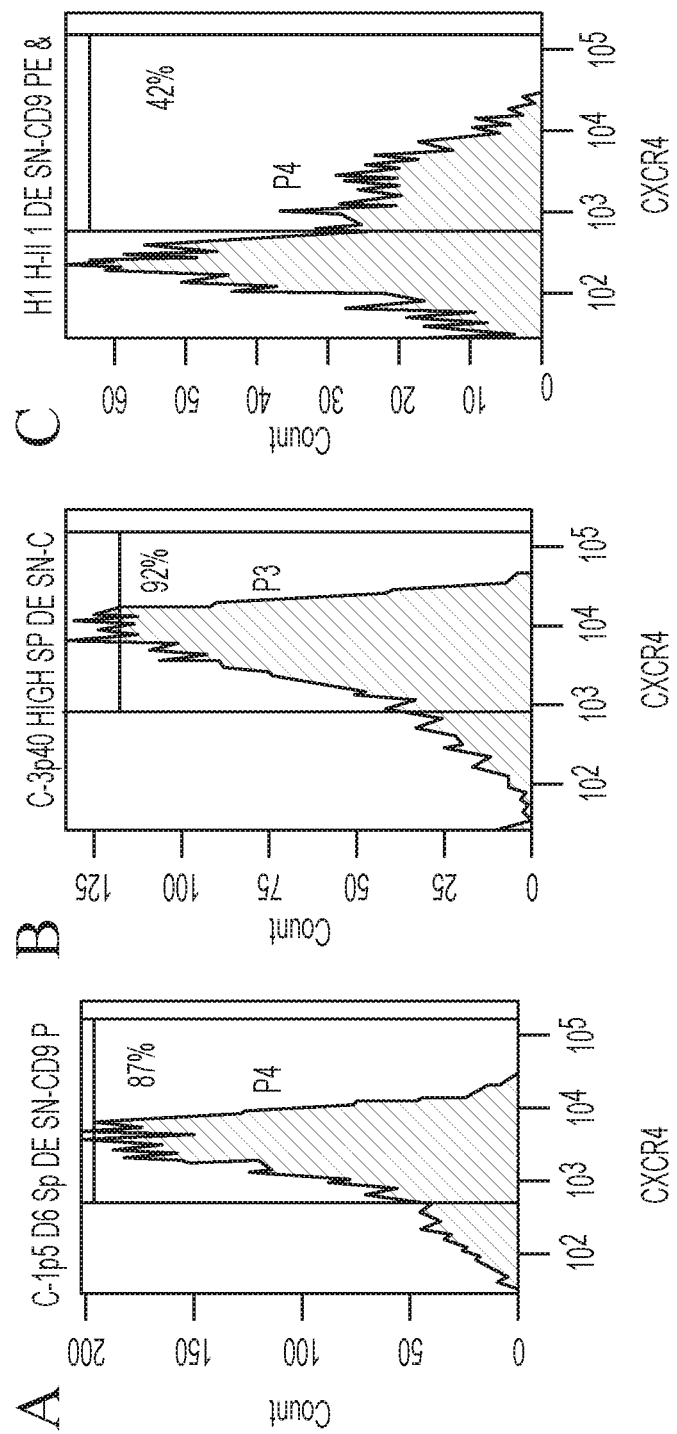
FIG. 28: Differentiation of H1 cells on micro-carriers to definitive endoderm. Here FACS plots display the percentage of cells expressing the definitive endoderm marker CXCR4. Percent positive is in the upper right corner. Cells were all expanded on micro-carriers in spinner flasks prior to treatment. A, H1 cells at passage 40 were grown on Cytodex 1® micro-carriers (GE Healthcare Life Sciences, NJ) for 6 days after passage 5 prior to differentiation. B, H1 cells at passage 40 were grown on Cytodex 3® micro-carriers (GE Healthcare Life Sciences, NJ) for 8 days after passage 1 prior to differentiation. C, H1 cells at passage 50 were grown on HILLEX®II micro-carriers (Solohill, MI) for 6 days after passage 1 prior to differentiation.

Three types of micro-carriers, Cytodex 1®, Cytodex 3® (GE Healthcare Life Sciences, NJ) and HILLEX®II (Solohill, MI), allow attachment and growth of H1 cells. Differentiation of H1 cells on these three micro-carriers was conducted. The cells were grown on these micro-carriers in spinner flasks (Example 5) for various passage numbers (1 to 5). Six to eight days after the last passage aliquots of the micro-carriers plus cells in suspension were transferred to 6 or 12 well plates. A total of 15 cm$^2$ of micro-carriers plus cells per 12 well plate well or 30 cm$^2$ micro-carriers plus cells per 6 well plate was transferred. Differentiation medium was then added to the plate wells and the plate was placed on a rocking platform at 37° C. Differentiation of the human embryonic stem cells to definitive endoderm was conducted by treating the cells for 2 days with 2% Albumin Bovine Fraction V Fatty Acid Free (MP Biomedicals, Ohio) in RPMI plus 100 ng/ml Activin A (PeproTech, NJ), 20 ng/ml Wnt3a (R&D Biosciences, MN) and 8 ng/ml bFGF (PeproTech, NJ). The cells were treated for an additional 2 days in 2% FAF BSA in RPMI plus 100 ng/ml Activin A (PeproTech, NJ) and 8 ng/ml bFGF (PeproTech, NJ). Medium was changed daily. FACS analysis was conducted for the definitive endoderm cell surface marker CXCR4 (FIG. 28). Cells grown on Cytodex 1®, and Cytodex 3® micro-carriers supported differentiation to definitive endoderm (87% and 92% respectively while HILLEX®II micro-carriers did not support differentiation as to the same extent as the other micro-carriers tested in this experiment (42%).

Figure 29:
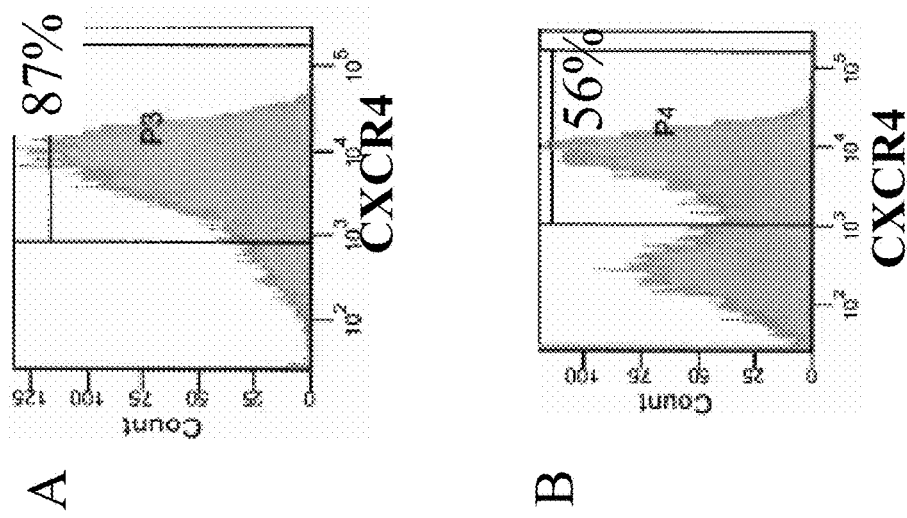
FIG. 29: Differentiation of H1 cells on Cytodex 3® micro-carriers (GE Healthcare Life Sciences, NJ) to definitive endoderm. A, H1 cells at passage 40 were grown on micro-carriers for eight days. B, H1 cells at passage 40 were grown on micro-carriers for 11 days. Both cell population were then differentiated to definitive endoderm on a rocking platform at 37° C. Here FACS plots display the percentage of cells expressing the definitive endoderm marker CXCR4. Percent positive is in the upper right corner.

To determine if the cell density affects differentiation of the cells on micro-carriers, cells of the human embryonic stem cell line H1 at passage 40 were grown on Cytodex 3® micro-carriers in a spinner flask for either 8 days or 11 days. Then the equivalent of about 15 cm² of micro-carriers plus cells was placed in a 6 well dish and placed on a rocking platform. The cells were then incubated in definitive endoderm differentiating medium as above. After 4 days the cells were analyzed by FACS for CXCR4 expression. 87% of the cells grown for 6 days in spinner flask expressed CXCR4 while 56% of cells grown for 11 days in the spinner flask expressed CXCR4 (FIG. 29). This demonstrates that the number of days that the cells are in culture is important prior to differentiation, specifically, if the cell density is too high it may not allow the cells to efficiently differentiate.

To determine if human embryonic stem cells could be differentiated into pancreatic endoderm cells on all three micro-carrier types determined sufficient for attachment and growth, cells of the human embryonic stem cell line H1 at passage 41 (H1p41) were seeded on to Cytodex 1®, Cytodex 3® micro-carriers (GE Healthcare Life Sciences, NJ) and HILLEX®II micro-carriers (Solohill, MI) (see Example 1). Micro-carriers were prepared according to the manufactures instructions. 30 cm² of micro-carriers were transferred to low attachment 6 well plates. The H1 cells were dissociated from two 10 cm² plates with TrypLE™ Express according to manufacturer's instructions. Cell were seeded at 5×10⁵ cells per well. Attachment of the cells to the beads was carried out according to the methods described in Example 3. Briefly, the cells and micro-carriers were incubated in MEF conditioned media with 10 µM Y27632 at 37° C. for four hours with brief agitation each hour. The cells on HILLEX®II and Cytodex 1® micro-carriers were placed on a rocking platform. The cells on Cytodex 3® micro-carriers were allowed to sit undisturbed overnight. The media was changed daily and no longer included Y27632.

Figure 30:
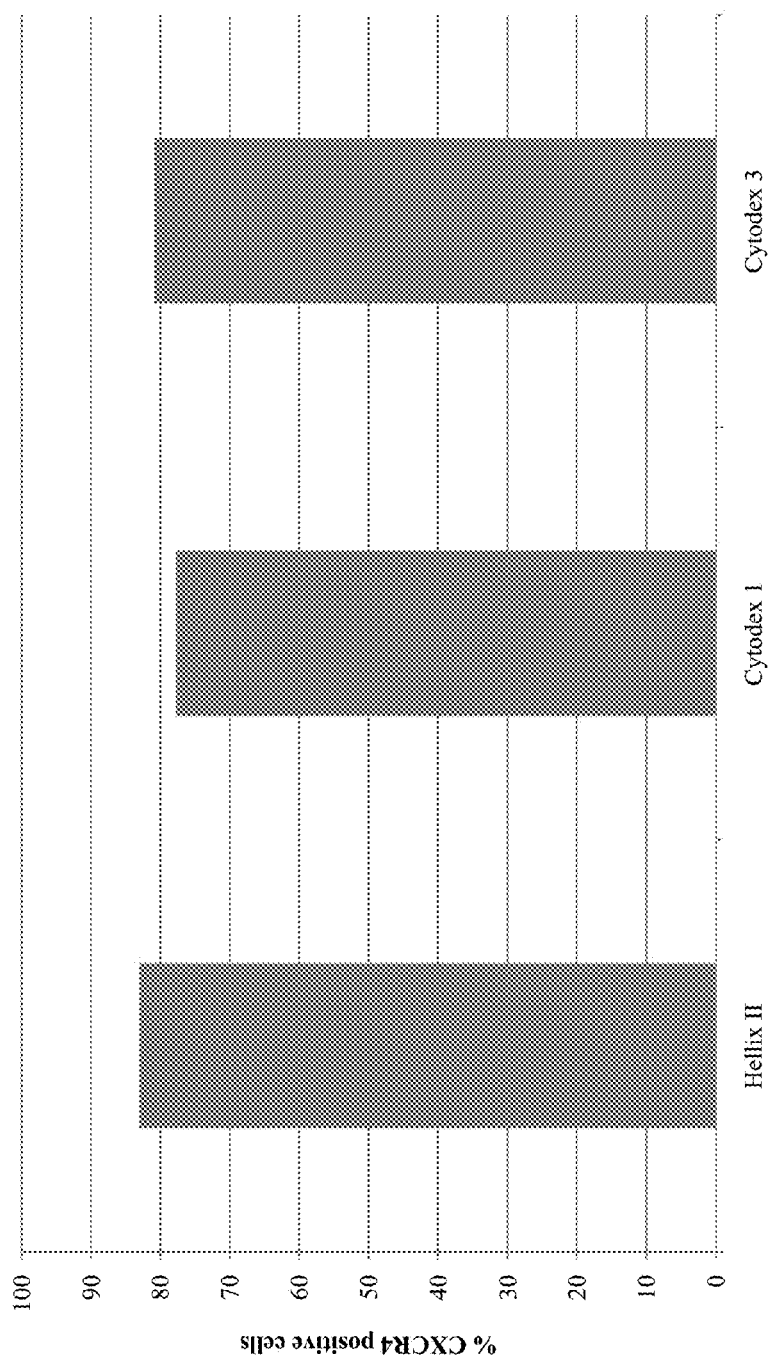
FIG. 30: Differentiation of cells of the human embryonic stem cell line H1, cultured on micro-carriers to definitive endoderm. FACS results for the percent positive CXCR4 cells are shown on the Y-axis. H1 cells were grown on HILLEX®II, Cytodex 1® or Cytodex 3® micro-carriers prior to and during differentiation.

Due to poor attachment in this experiment, the majority of cells in the Cytodex 1® plate were no longer attached to the micro-carriers. However, longer attachment time and/or slower rocking speed may improve the cell attachment. After 7 days, the cells were differentiated to definitive endoderm with 2% fatty acid free (FAF) BSA (Proliant, Iowa) in RPMI and the following growth factors: bFGF (8 ng/ml, (PeproTech, NJ)), Activin A (100 ng/ml, (PeproTech, NJ)), Wnt3a (20 ng/ml, (R&D Biosciences, MN)). For the second through fourth day of differentiation, the cells were treated with the same media lacking Wnt3a. FACS analysis of duplicate samples after 4 days revealed CXCR4 levels of 77-83% positive cells. Definitive endoderm expression was equivalent between cells grown on the different micro-carriers. See FIG. 30.

Figure 31:
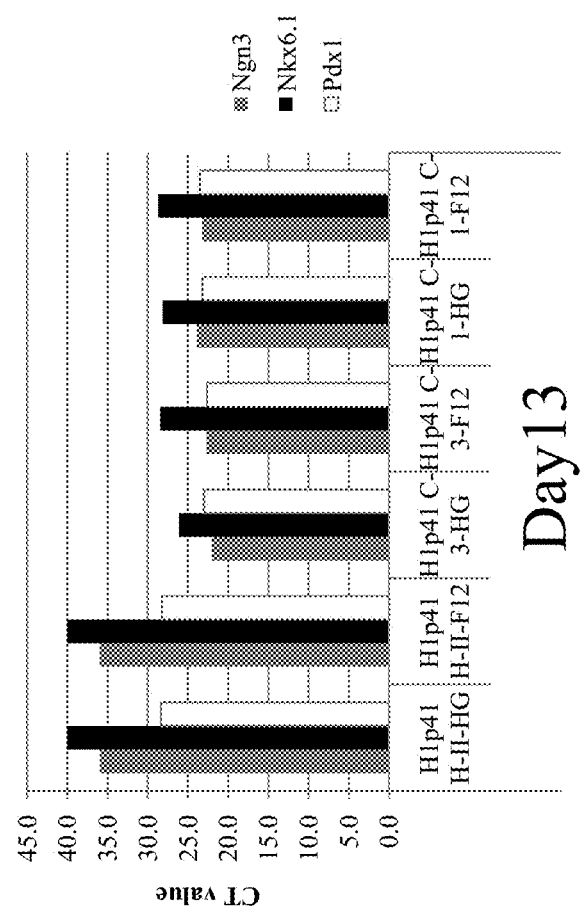
FIG. 31: Differentiation of cells of the human embryonic stem cell line H1 cultured on micro-carriers to pancreatic endoderm cells. CT values are shown on the Y-axis for pancreatic endodermal markers, Ngn3, Nkx6.1 and Pdx1. H1 cells were differentiated on HILLEX®II (HII), Cytodex 1® (C1) or Cytodex 3® (C3) micro-carriers in either DMEM-High Glucose (HG) or DMEM-F12 (F12) media. The differentiation protocol lasted 13 days.

The cells were then differentiated further for 2 days with FGF7 (50 ng/ml, (R&D Systems, MN)), KAAD-Cyclopamine (0.25 µM, (Calbiochem, NJ)) in DMEM/F12 or DMEM-HG plus 2% FAF BSA (Proliant, Iowa). This was followed by four days of treatment with Noggin (100 ng/ml, (R&D Biosciences, MN)), FGF7 (50 ng/ml, (R&D Systems, MN)), Retinoic Acid (2 µM, (Sigma-Aldrich, MO)), and KAAD-Cyclopamine (0.25 µM, (Calbiochem, NJ)) in DMEM/F12 or DMEM-HG with 1% B-27 supplement (Invitrogen, CA). The cells were then differentiated for three days with Noggin (100 ng/ml, (R&D Biosciences, MN)), DAPT (1 µM, (Sigma-Aldrich, MO)), Alk5 inhibitor II (1 µM, (Axxora, CA)) in DMEM/F12 or DMEM-HG with 1% B-27 supplement (day 13, pancreatic endoderm, (Invitrogen, CA)). FIG. 31 shows the expression level by Q-PCR for the pancreatic specific genes, NKX6.1, PDX1 and NGN3. CT values clearly show that cells differentiated on HILLEX®II micro-carriers do not differentiate efficiently to express the necessary beta cell precursor cell markers. Although the cells differentiated efficiently to definitive endoderm on all three micro-carrier types further differentiation to pancreatic progenitors is not efficient on HILLEX®II micro-carriers.

Figure 32:
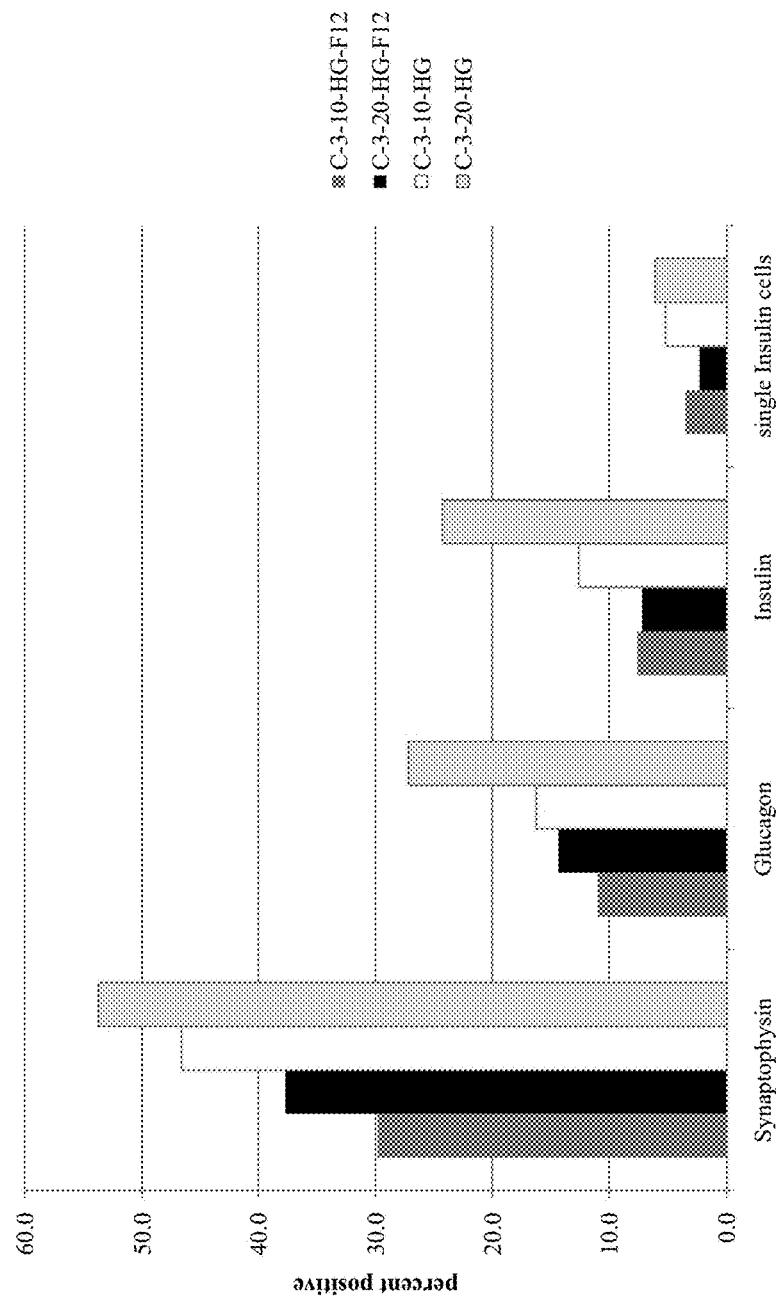
FIG. 32: Differentiation of cells of the human embryonic stem cell line H1 cultured on micro-carriers to hormone producing pancreatic cells. Percent positive cells were determined by FACS shown on the Y-axis for pancreatic hormone cell markers, Synaptophysin, Glucagon and Insulin. H1 cells were seeded at two different concentrations $10 \times 10^5$ (10) or $20 \times 10^5$ (20) onto Cytodex 3® (C-3) micro-carriers. The cells were differentiated in DMEM-High Glucose (HG) during days four to nine and further differentiated in either HG or DMEM-F12 (F12) media from days 10 through 24.

To determine if the human embryonic stem cells could be further differentiated into insulin producing cells, H1p45 cells were grown on Cytodex 3® micro-carriers (GE Healthcare Life Sciences, NJ) and differentiated similar to above. Briefly, H1 cells were dissociated from 10 cm² plates with TrypLE™ Express according to manufacturer's instructions. Cells were seeded at 1 or 2×10⁶ cells per 6 well plate well. Attachment of the cells to the beads is described in Example 3. Briefly, the cells and micro-carriers were incubated in MEF conditioned media with 10 µM Y27632 at 37° C. for four hours with brief agitation each hour. The cells were then allowed to incubate overnight undisturbed. On day 2 the media was replaced with MEF conditioned media plus 5 uM Y27632 and the plates were placed on a rocking platform. The media was changed each subsequent day without Y27632. On day five, the media was replaced with definitive endoderm differentiation media, 2% fatty acid free (FAF) BSA (Proliant, Iowa) in RPMI with the following growth factors: bFGF (8 ng/ml, (PeproTech, NJ)), Activin A (100 ng/ml, (PeproTech, NJ)), Wnt3a (20 ng/ml, (R&D Biosciences, MN)). For the second and third day of differentiation, the cells were treated with the same media lacking Wnt3a. FACS analysis of duplicate samples after 3 days revealed CXCR4 levels of 97-98% positive cells. The cells were then differentiated further for 2 days with FGF7 (50 ng/ml, (R&D Systems, MN)), KAAD-Cyclopamine (0.25 µM, (Calbiochem, NJ)) in DMEM-High Glucose (HG) plus 2% FAF BSA (Proliant, Iowa). This was followed by four days of treatment with Noggin (100 ng/ml, (R&D Biosciences, MN)), FGF7 (50 ng/ml, (R&D Systems, MN)), Retinoic Acid (2 µM, (Sigma-Aldrich, MO)), and KAAD-Cyclopamine (0.25 µM, (Calbiochem, NJ)) in DMEM-HG with 1% B-27 supplement (Invitrogen, CA). The cells were then differentiated for three days with Noggin (100 ng/ml, (R&D Biosciences, MN)), DAPT (1 µM, (Sigma-Aldrich, MO)), Alk5 inhibitor II (1 µM, (Axxora, CA)) in DMEM-HG or DMEM-F12 with 1% B-27 supplement (Invitrogen, CA). This was followed by differentiation in DMEM-HG or DMEM-F12 with Alk5 inhibitor II (1 µM, (Axxora, CA)) for seven days. Final differentiation was for five days in DMEM-HG or DMEM-F12 respectively. This is a total of 24 days of differentiation leading to expression of pancreatic endocrine hormones. FIG. 32 shows the FACS analysis results of the cells at this end point. Cells with the highest seeding density and differentiated in DMEM-HG from days 6 through 24 had the highest levels of insulin expression (FIG. 32).

Figure 33:
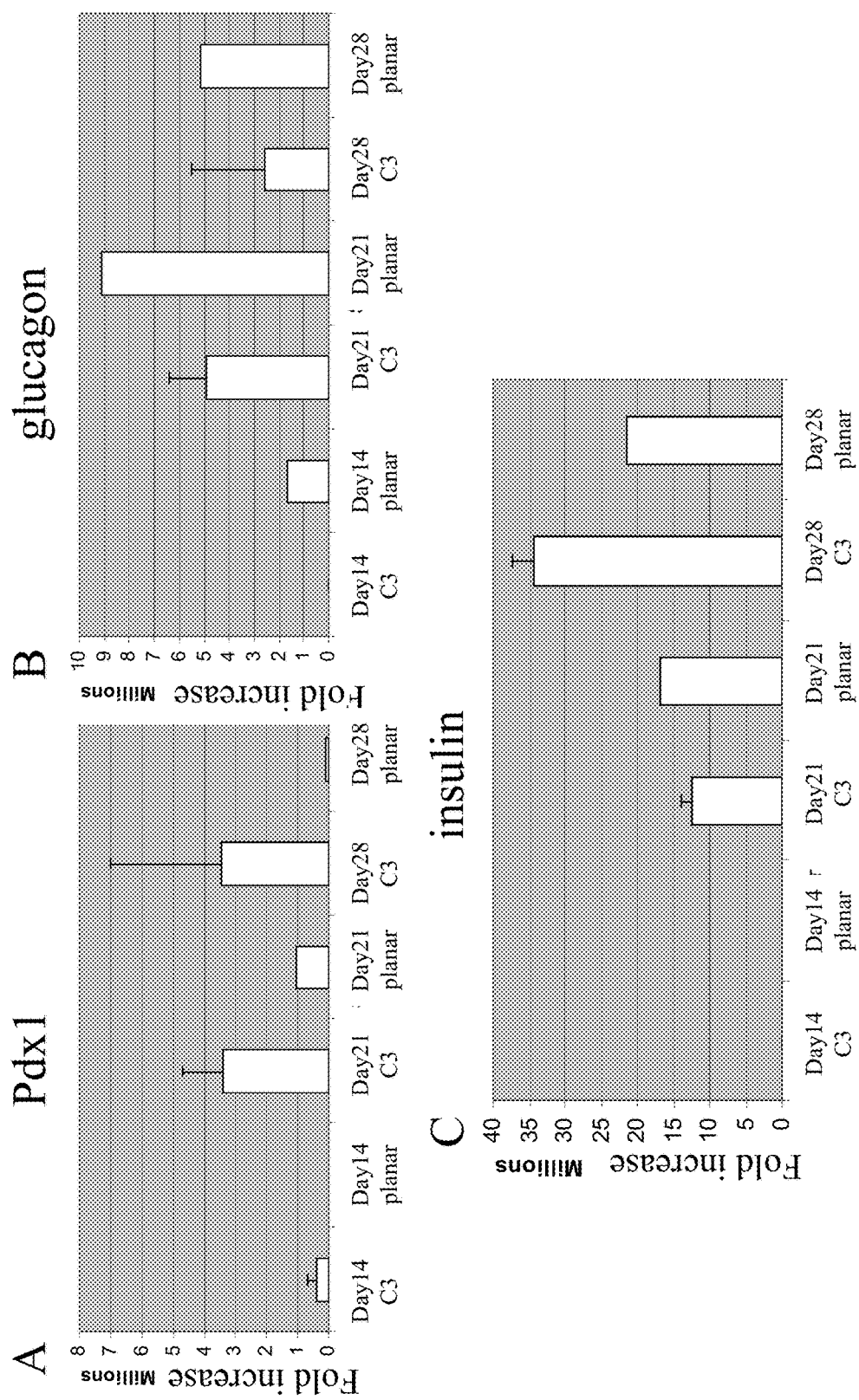
FIG. 33: Differentiation of H1 cells on Cytodex 3® micro-carriers (GE Healthcare Life Sciences, NJ) to endocrine cells. H1 cells were differentiated to pancreatic endocrine cells through pancreatic endoderm (Day 14), pancreatic endocrine cells (Day 21) to insulin-expressing cells (Day 28). Gene expression levels of Pdx1, Glucagon, and Insulin were measured (A, B, C respectively). H1 cells grown and differentiated on Cytodex 3® micro-carriers (GE Healthcare Life Sciences, NJ) (C3) were compared to those grown and differentiated on MATRIGEL (BD Biosciences, CA) coated 6 well dishes (planar). The gene expression values for cells grown on Cytodex 3® micro-carriers (GE Healthcare Life Sciences, NJ) was performed in triplicate.

Alternatively, to determine if the human embryonic stem cells could be differentiated into insulin producing cells, H1p44 cells were grown in a spinner flask for 7 days on Cytodex 3® micro-carriers (see Example 5). The cells plus micro-carriers were transferred to a 12 well plate at 15 cm$^2$/well and placed on a rocking platform at 37° C. The cells were differentiated to definitive endoderm as above but with DMEM/F12 instead of RMPI. FACS analysis after 4 days revealed CXCR4 levels of 75 to 77% positive cells in a triplicate analysis. The cells were then differentiated further with 3 days of treatment with FGF7 (50 ng/ml, (R&D Systems, MN)), KAAD-Cyclopamine (0.25 µM, (Calbiochem, NJ)) in DMEM/F12 plus 2% Albumin Bovine Fraction V Fatty Acid Free. This was followed by four days of treatment with Noggin (100 ng/ml, (R&D Biosciences, MN)), FGF7 (50 ng/ml, (R&D Systems, MN)), Retinoic Acid (2 µM, (Sigma-Aldrich, MO)), and KAAD-Cyclopamine (0.25 µM, (Calbiochem, NJ)) in DMEM/F12 with 1% B-27 supplement (Invitrogen, CA). The cells were then differentiated for three days with Noggin (100 ng/ml, (R&D Biosciences, MN)), Netrin4 (100 ng/ml, (R&D Biosciences, MN)), DAPT (1 µM, (Sigma-Aldrich, MO)), Alk5 inhibitor II (1 µM, (Axxora, CA)) in DMEM/F12 with 1% B-27 supplement (day 15, pancreatic endoderm, (Invitrogen, CA)). This was followed by six days of treatment with Alk5 inhibitor II (1 µM, (Axxora, CA)) in DMEM/F12 with 1% B-27 supplement (day 21, pancreatic endocrine cells, (Invitrogen, CA)). The final treatment for seven days was DMEM/F12 with 1% B-27 supplement (day 28, insulin-expressing cells, (Invitrogen, CA)). FIG. 33 shows the expression level by Q-PCR for the pancreatic specific genes, insulin, Pdx1 and glucagon. The data on micro-carriers is compared to previous data of H1p42 cells differentiated on a MATRIGEL™ (BD Biosciences, CA) coated planar surface. The expression level of these pancreas specific genes is similar or better for micro-carrier differentiated cells compared to cells differentiated on planar surfaces.

Figure 34:
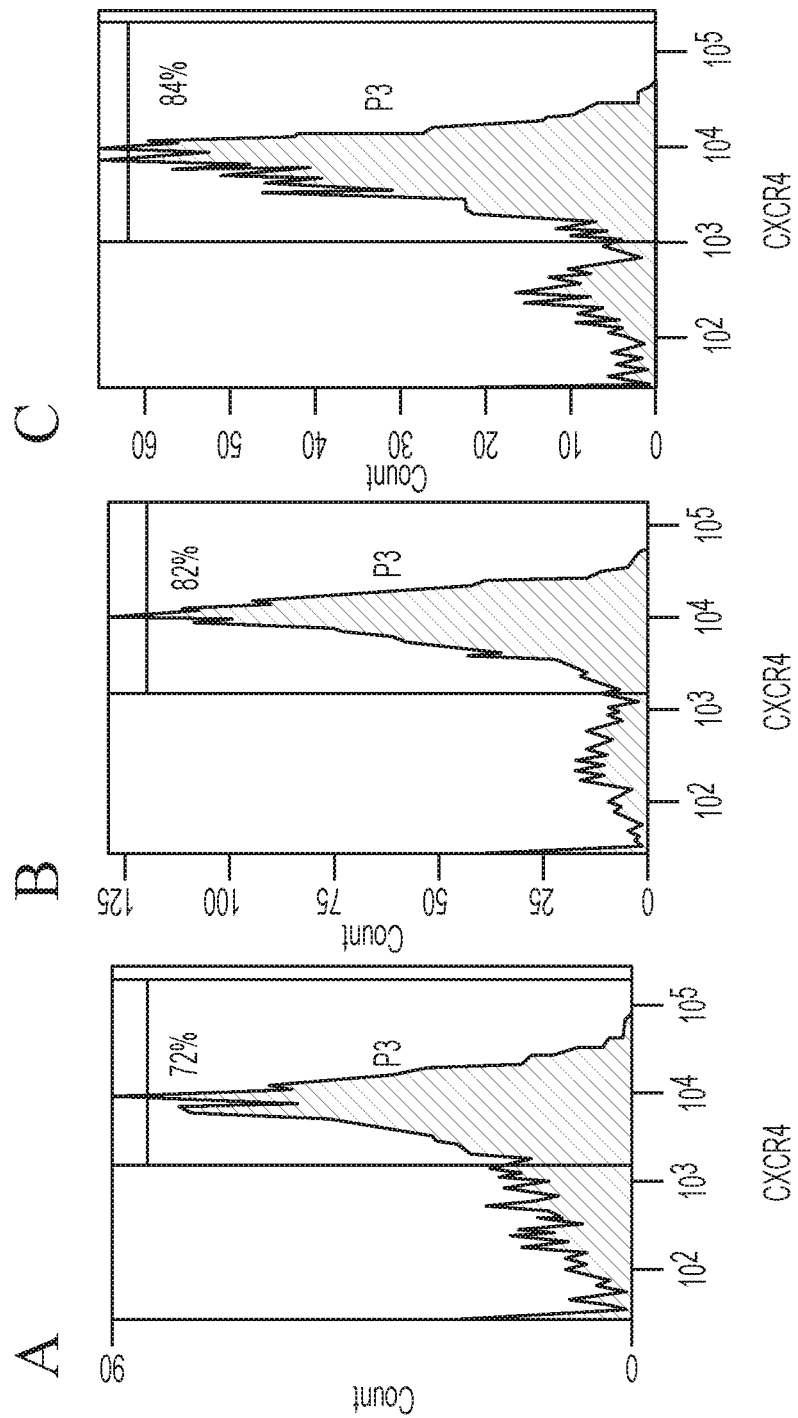
FIG. 34: H9 cells were differentiated on Cytodex 3® micro-carriers (GE Healthcare Life Sciences, NJ) to definitive endoderm (DE). FACS plots of CXCR4 expression. Percent of definitive endoderm marker CXCR4 positive cells is stated in upper right corner. A, H9 cells at passage 39 were grown on a MATRIGEL (BD Biosciences, CA) coated 6 well dishes and differentiated to DE. B, C Duplicate samples of H9 cells on Cytodex 3® micro-carriers (GE Healthcare Life Sciences, NJ) from spinners were placed in a 12 well dish and incubated on a rocking platform.
Figure 35:
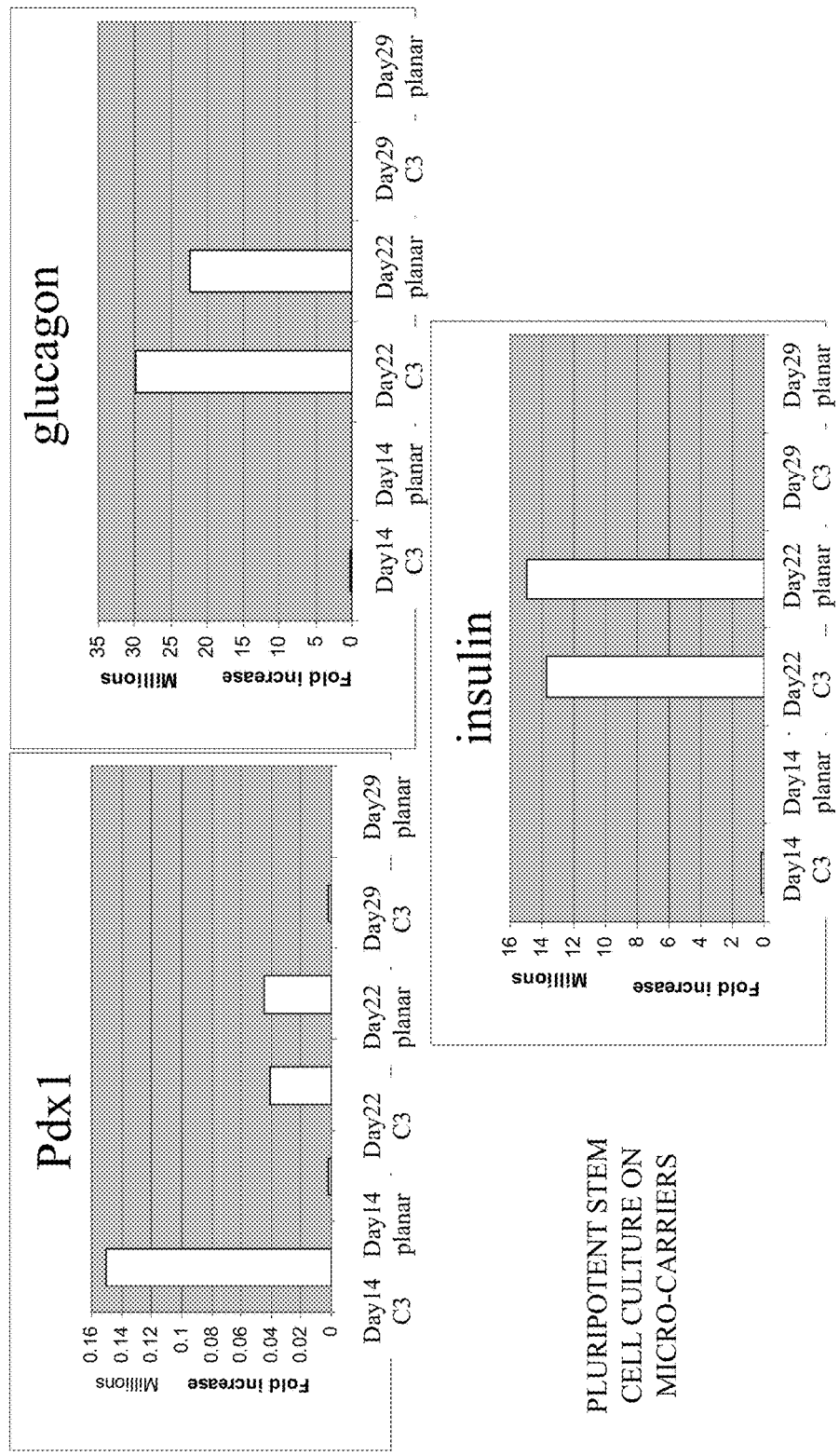
FIG. 35: Differentiation of H9 cells on Cytodex 3® micro-carriers (GE Healthcare Life Sciences, NJ) to insulin-expressing cells. H9 cells were differentiated to pancreatic endocrine cells through pancreatic endoderm (Day 14), Endocrine cells (Day 22) to Insulin-expressing cells (Day 29). Gene expression level of Pdx1, Glucagon, and Insulin was measured (A, B, C respectively). H9 cells grown and differentiated on Cytodex 3® micro-carriers (GE Healthcare Life Sciences, NJ) (C3) were compared to those grown and differentiated on MATRIGEL (BD Biosciences, CA) coated 6 well dishes (planar).

Similar experiments were conducted with H9 p38 cells passaged onto Cytodex 3® micro-carriers and expanded in a spinner flask. An aliquot of 15 cm$^2$ of micro-carriers plus cells was placed in a 12 well plate and placed on a rocking platform with differentiation medium. This was compared to cells plated on a 6 well plate coated with MATRIGEL™ (BD Biosciences, CA). Differentiation of the cells to definitive endoderm in RPMI and supplements was achieved, with an average of 83% of the cells expressing CXCR4 (samples in duplicate) compared to 72% of cells expressing CXCR4 on a planar substrate (FIG. 34). Further differentiation to pancreatic endoderm (day 15), pancreatic-endocrine cells (day 22) and insulin-expressing cells (day 29) showed similar expression levels of insulin and glucagon between cells grown on micro-carriers to those grown on a planar substrate (FIG. 35). The medium components were identical to those listed for the above H1 differentiation experiment with one additional day in the endocrine cell differentiating components. At the insulin-expressing stage, cells showed a surprising decrease in insulin expression compared to day 22. Since the decrease was noted in both micro-carrier and planar samples, it is likely not due to the attachment substrate. This shows that H9 cells can also be successfully differentiated to at least pancreatic endocrine cells on micro-carriers.

Overall, two different human embryonic stem cell lines, H1 and H9, can be differentiated to pancreatic endocrine cells on Cytodex 3® micro-carriers, illustrating the potential to expand and differentiate these cells in a large-scale culture system (FIGS. 17, 21, 33, and 35). Human embryonic stem cells were able to attach and proliferate to at least three micro-carrier bead types and the cells could be differentiated to at least definitive endoderm (FIG. 28). These results illustrate a method by which human embryonic stem cells can be expanded and differentiated for therapeutic uses.

Example 8: Human Embryonic Stem Cells Passaged as Single Cells in a 3D Micro-Carrier Based Culture can be Transferred to Culture on an ECM Free Surface While Maintaining Pluripotency H1 human embryonic stem cells were cultured on micro-carriers according to the methods described in Example 5. Cells were removed from micro-carriers and plated to Nunc4, Nunc13, CELLBIND™, or PRIMARIA™ tissue culture polystyrene (TCPS) planar surfaces with MEFCM16 supplemented with 3 µM Glycyl-H 1152 dihydrochloride. The cells were seeded at a density of 100,000 cells/cm$^2$ in six well plates and then cultured for one additional passage on the respective surface. Cells were then either lifted with TrypLE and tested by flow cytometry for pluripotency markers, or lysed in the well with RLT for mRNA purification and qRT-PCR, or differentiated to definitive endoderm. Differentiation was induced by treating the cells with RPMI media supplemented with 2% BSA, 100 ng/ml Activin A, 20 ng/ml Wnt3a, 8 ng/ml bFGF, and 3 µM Glycyl-H 1152 dihydrochloride for 24 hours. Media was then changed to RPMI media supplemented with 2% BSA, 100 ng/ml Activin A, 8 ng/ml bFGF, and 3 µM Glycyl-H 1152 dihydrochloride for an additional 48 hours with daily media change.

Figure 36:
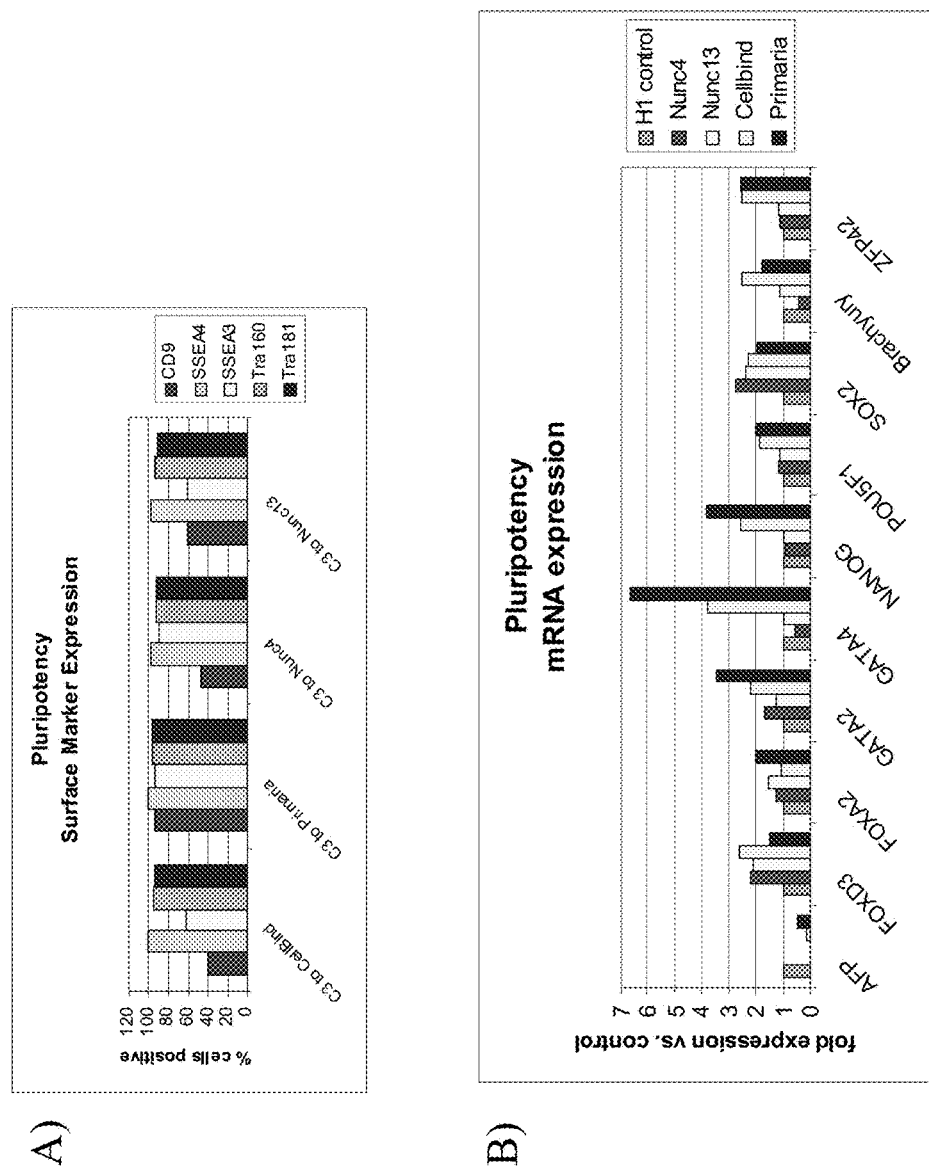
FIG. 36: Maintenance of pluripotency in human embryonic stem cells cultured for 5 passages on Cytodex 3® micro-carriers, then transferred and cultured on the planar substrates indicated and cultured in the presence of a Rho kinase inhibitor. Panel A depicts the expression of the pluripotency markers CD9, SSEA3, SSEA4, Tra-160, and Tra-181 as detected by flow cytometry. Panel B depicts the expression of the pluripotency markers Nanog, Pou5F1, SOX2, and ZFP42 and markers of differentiation: FOXA2, FOXD3, GATA2, GATA4, and Brachyury as detected by real-time PCR.
Figure 37:
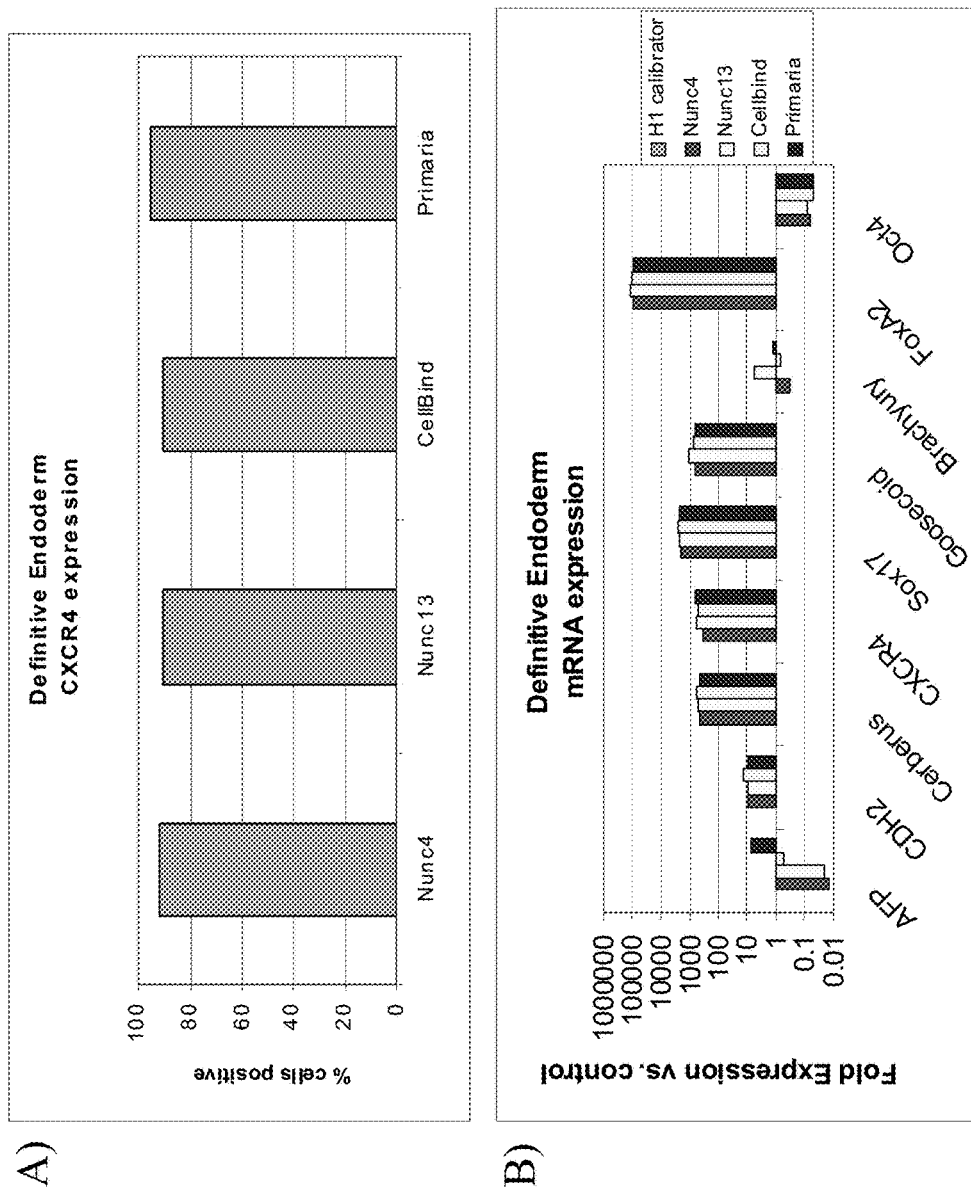
FIG. 37: Formation of definitive endoderm by human embryonic stem cells cultured for 5 passages on Cytodex 3® micro-carriers, then transferred and cultured on the planar substrates indicated and cultured in the presence of a Rho kinase inhibitor. Panel A depicts the expression of CXCR4 as detected by flow cytometry. Panel B depicts the expression of the markers indicated as detected by real-time PCR.
Figure 38:
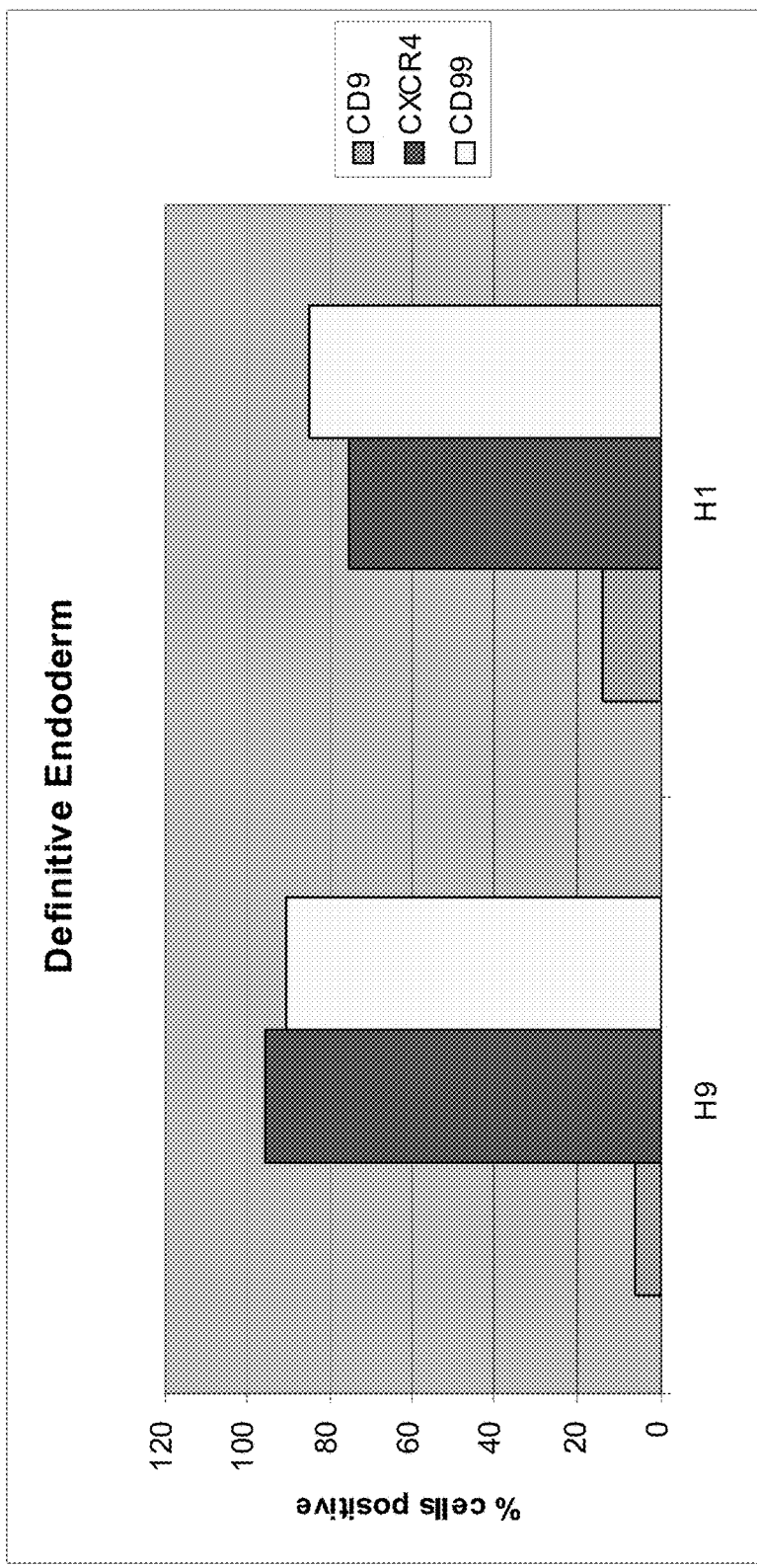
FIG. 38: Formation of definitive endoderm by human embryonic stem cells cultured for 5 passages on Cytodex 3® micro-carriers, then transferred and cultured on a PRIMARIA™ planar substrate. Expression of the genes indicated was determined by flow cytometry.

As measured by pluripotency markers, using either flow cytometry or qRT-PCR, cells cultured on micro-carriers and transferred to culture on Nunc4, Nunc13, CellBIND, or Primaria tissue culture polystyrene (TCPS) planar surfaces maintained pluripotency after two passages on the respective planar surface (FIG. 36). Furthermore, the cells maintained the capacity to differentiate to a definitive endoderm fate as measured by either flow cytometry or qRT-PCR (FIG. 37). Similar results were also obtained in side-by-side tests of H1 and H9 human embryonic stem cells passaged on Cytodex 3® micro-carriers and differentiated to definitive endoderm (FIG. 38).

These results indicate that human embryonic stem cells can be passaged on micro-carriers and then subsequently cultured on another surface while maintaining pluripotency. The cells may also be transferred to another surface and efficiently induced to differentiate.

Example 9: Human Embryonic Stem Cells can be Transferred Directly from a Cluster/Colony Style Culture on Mitotically Inactivated Fibroblast Feeders to Culture as Single Cells on ECM Free Surfaces for at Least 10 Passages Without Loss of Pluripotency and Without Manual Removal of Fibroblast Feeders Human embryonic stem cell lines are currently derived using a method that promotes a colony outgrowth of a single cell or a cluster of a few cells from a blastocyst. This colony outgrowth is then serially passaged and propagated until enough cluster/colonies of cells are available that they constitute a cell line. Once a cell line has been derived, in order to maintain the pluripotent and karyotypically stable characteristics of human embryonic stem cells, the current standard in the art for high quality, reproducible culture of human embryonic stem cells is to maintain the clusters/colonies of human embryonic stem cells on a feeder layer of mitotically inactive fibroblasts and to pass the cells using manual disruption or gentle enzymatic bulk passage with collagenase or neutral protease or a blend thereof. These passage methods maintain human embryonic stem cells clusters and promote colony style growth of human embryonic stem cell. After a stable human embryonic stem cell line is established the cells can be transitioned to an extracellular matrix (ECM) substrate such as MATRIGEL™. However, whether the cells are grown on fibroblast feeders or on an ECM substrate, the recommended passage method for human embryonic stem cells specifically instructs technicians not to fully dissociate human embryonic stem colonies.

The current best practice for large scale culture of mammalian cells is to use a 3-dimensional culture vessel that tightly maintains homeostatic, uniform conditions and can incorporate micro-carriers for support of adhesion dependent cells. However, the current standard methods used for human embryonic stem cell culture-growth on fibroblast feeders or an ECM substrate and cluster/colony style culture pose a technical hurdle to successfully growing and maintaining a pluripotent human embryonic stem cell culture on micro-carriers, since these methods are not easily transferable to large scale culture on micro-carriers. In order to effectively grow human embryonic stem cells on micro-carriers the human embryonic stem cell culture must be able to be passaged as single cells, and not as colonies or clusters, as is currently the standard in the art. Furthermore, the human embryonic stem cells should be able to grow without a layer of feeder cells or ECM substrate.

A method which addresses these technical hurdles is described below. It is demonstrated how to convert human embryonic stem cell cultures from clusters/colonies on a mitotically inactive fibroblast feeder layer directly to a single cell culture system that does not require an underlying fibroblast feeder layer or a surface coated with MATRIGEL or other an extracellular matrix substrate. This method utilizes bulk passage of human embryonic stem without any manual removal of fibroblast feeder cells or selection of pluripotent cells from the total cell population to convert the culture directly from colony style, fibroblast feeder based culture to feeder free/matrix free culture on PRIMARIA in the presence of the Rho Kinase (ROCK) inhibitor, Glycyl-H 1152 dihydrochloride. This method can be completed in a sealed vessel to adhere to regulatory requirements and produces a highly homogeneous human embryonic stem culture that retains pluripotency and the ability to differentiate to definitive endoderm, and does not contain a fibroblast cell population.

Method: Cells were routinely passaged by aspirating media, washing with PBS, and then treating the cells with a dissociation enzyme (collagenase, Accutase™, or TrypLE). Collagenase was used at 1 mg/ml concentration; Accutase™ or TrypLE were used at 1× stock concentration. All enzymes were used after reaching room temperature. A solution of 2% BSA in DMEM/F12 was added to each well and cells were uniformly suspended in the solution after treating the cells with enzyme. Cells were then centrifuged for 5 minutes at 200 g, the cell pellet and additional 2% BSA in DMEM/F12 solution was added to resuspend cells and the cell suspension was distributed to three 50 ml sterile conical tubes and centrifuged for 5 min at 200 g.

Figure 39:
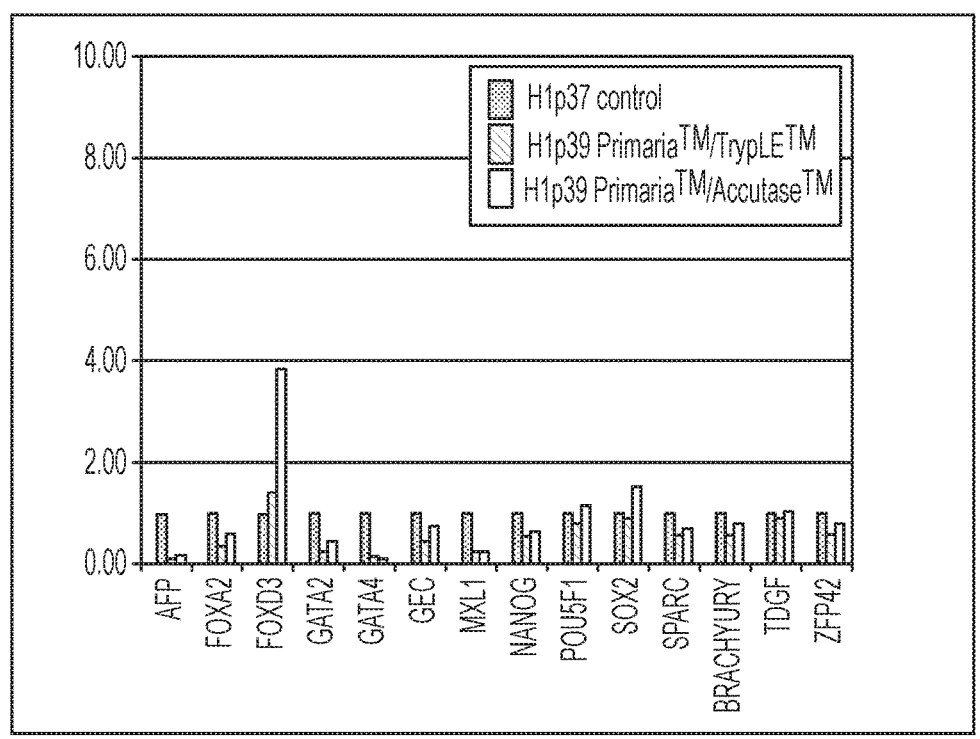
FIG. 39: Human embryonic stem cells cultured on planar substrates maintain pluripotency. mRNA samples from TrypLE™, Accutase™, or Collagenase passaged H1 human ES cells were collected and assayed for mRNA pluripotency gene expression. Cells were grown for either one passage for 4 days in culture on MATRIGEL in MEF conditioned media (A) or one passage on Primaria™ in MEF conditioned media supplemented with Rock Inhibitor (B), or two passages on Primaria™ in MEF conditioned media supplemented with Rock Inhibitor (C).

Using a sequential method, the fibroblast feeders were removed by high density passaging the cluster/colony style human embryonic stem cells to a Primaria surface by treating the MEF based culture with either Accutase™, TrypLE™, or collagenase. At the first passage, cells were plated to T-25 flasks coated with a 1:30 dilution of MATRIGEL™ in mouse embryonic fibroblast (MEF) conditioned media (CM) or the cells were plated to T-25 PRIMARIA™ culture flasks in MEF-CM plus 3 µM Glycyl-H 1152 dihydrochloride. All cells were plated at a split ratio of 1 to 3.5 and cells were exposed to enzyme for 10 minutes. Cell number for cells lifted with TrypLE™ or Accutase™ was determined by counting trypan blue stained cells with a hemocytometer. After plating the cells the media was changed daily, and cells plated in MEF-CM+3 µM Glycyl-H 1152 dihydrochloride were fed daily with MEF-CM+1 µM Glycyl-H 1152 dihydrochloride and samples were assayed for expression of mRNA markers of pluripotency and differentiation. hESCs passaged twice as single cells under Matrix free conditions maintained gene expression of pluripotency genes and inhibited expression of differentiation genes (FIG. 39).

$2^{nd}$ passage: Cells were passaged at a ratio of 1 to 4 using a 10 minutes exposure to TrypLE™ or Accutase™. A shorter enzyme exposure time, which was determined empirically by treating the cells and monitoring for detachment, was also introduced. 3 minute exposure to TrypLE™ and 5 minute exposure to Accutase™ was observed to be sufficient to lift the cells. After treating the cells with enzyme, the cells were passaged as described above and aliquots of cell mRNA were taken for qRT-PCR at the time of passaging.

$3^{rd}$ passage: Upon reaching confluence cells were washed with PBS, disrupted with enzyme for 3 or 10 minutes (TrypLE™) or 5 or 10 minutes (Accutase™), suspended in 2% BSA in DMEM/F12 and centrifuged, washed again with 2% BSA in DMEM/F12, centrifuged, and then resuspended and plated in their respective media. At this passage cells were plated at 1:4 ratio and also at 2 additional split ratios—1:8 and 1:16. Aliquots of cell mRNA were taken for qRT-PCR at each passage.

4 passages+: The conditions adopted for time of exposure to enzyme and passage ratio at passages 2 and 3 were maintained from passage 4 onward. Each time the culture grew to confluence cells were washed with PBS, disrupted with enzyme for the specified time, suspended in 2% BSA in DMEM/F12 and centrifuged, washed again with 2% BSA in DMEM/F12, centrifuged, and then resuspended in their respective media at the specified plating ratio. The media for cells plated to PRIMARIA was supplemented with 3 µM Glycyl-H 1152 dihydrochloride at the time of plating. After plating, media was changed daily and cells plated in MEF-CM+3 µM Glycyl-H 1152 dihydrochloride were fed daily with MEF-CM+1µ Glycyl-H 1152 dihydrochloride. Aliquots of cell mRNA were taken for qRT-PCR at the time of passaging.

Figure 40:
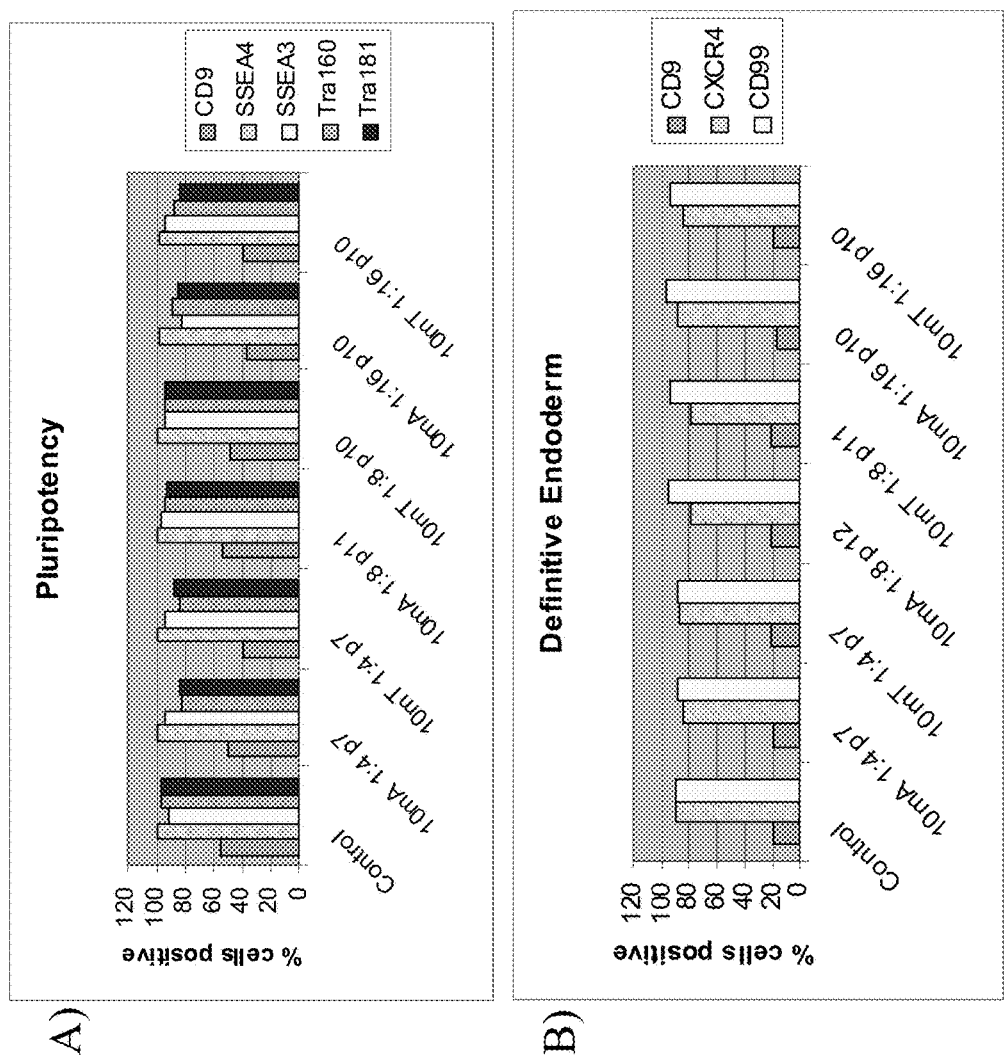
FIG. 40: H1 human embryonic stem cells grown for greater than 7 passages on PRIMARIA (greater than p45) passaged with Accutase™ or TrypLE™ at 1:4, 1:8, or 1:16 split ratios on PRIMARIA in the presence of Rho Kinase inhibitor Glycyl-H 1152 dihydrochloride were tested for pluripotency (A), and the ability to differentiate to Definitive Endoderm (B). The control is H1p48 human embryonic stem cells grown on 1:30 MATRIGEL passaged with collagenase. 10 mA=passaged with 10 minute exposure to Accutase™. 10 mT=passaged with 10 minute exposure to TrypLE™. 1:4, 1:8, or 1:16 indicate the passage ratio. P(X) indicate passage number since moving from MEF feeders to Primaria™ plastic.
Figure 41:
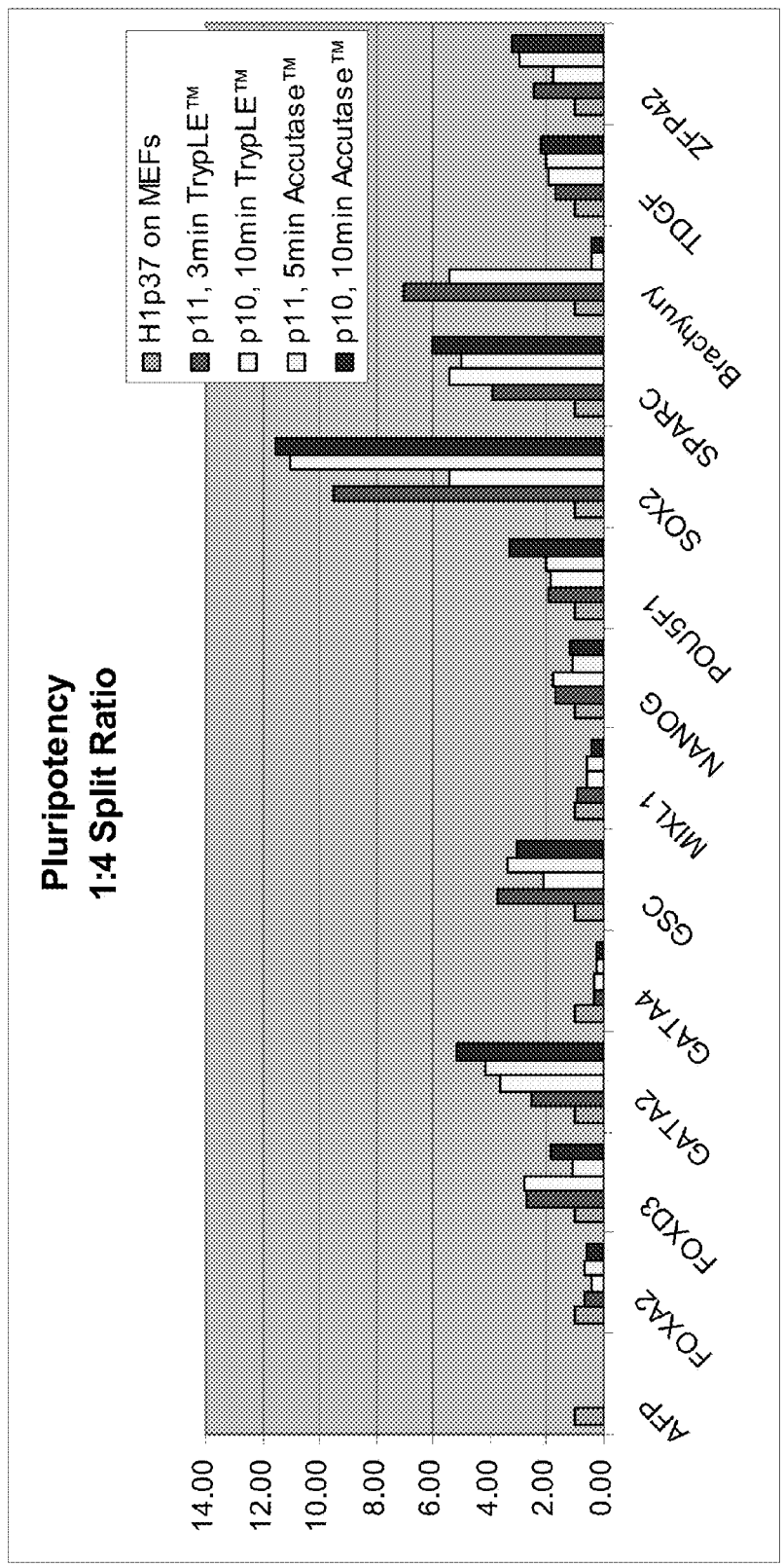
FIG. 41: H1 human embryonic stem cells grown for greater than 7 passages on PRIMARIA (greater than p45) passaged with Accutase™ or TrypLE™ at 1:4 ratio on PRIMARIA in the presence of Rho Kinase inhibitor Glycyl-H 1152 dihydrochloride were tested for mRNA expression of pluripotency and differentiation markers. The control is the starting population of cells at passage 37. 10 min Accutase™=passaged with 10 minute exposure to Accutase™. P(X) indicate passage number since moving from MEF feeders to PRIMARIA™ plastic.
Figure 42:
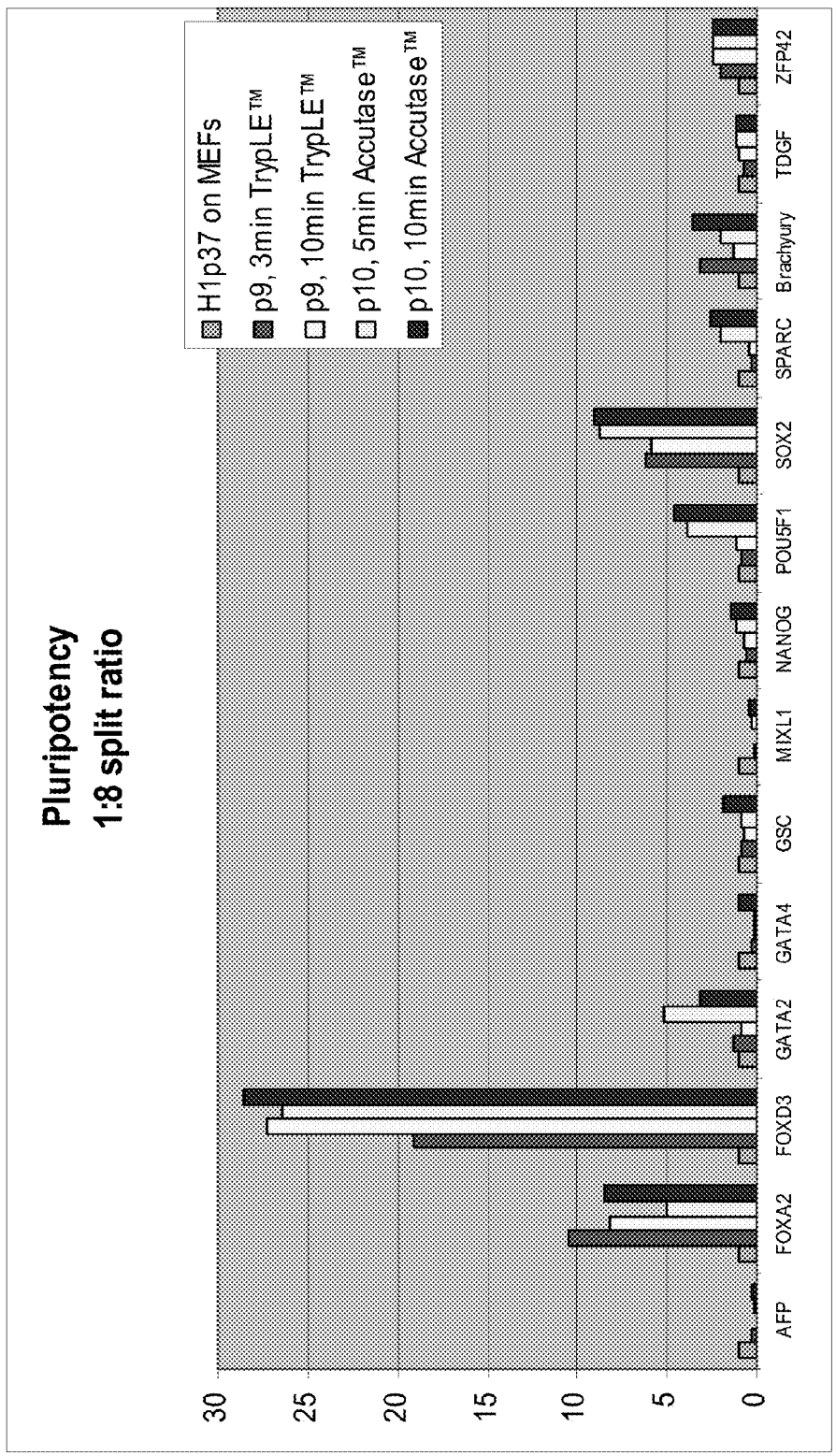
FIG. 42: H1 human embryonic stem cells grown for greater than 7 passages on PRIMARIA™ (greater than p45) passaged with Accutase™ or TrypLE™ at 1:8 ratio on PRIMARIA in the presence of Rho Kinase inhibitor Glycyl-H 1152 dihydrochloride were tested for mRNA expression of pluripotency and differentiation markers. The control is the starting population of cells at passage 37. 10 min Accutase™ passaged with 10 minute exposure to Accutase™. P(X) indicate passage number since moving from MEF feeders to PRIMARIA™ plastic.
Figure 43:
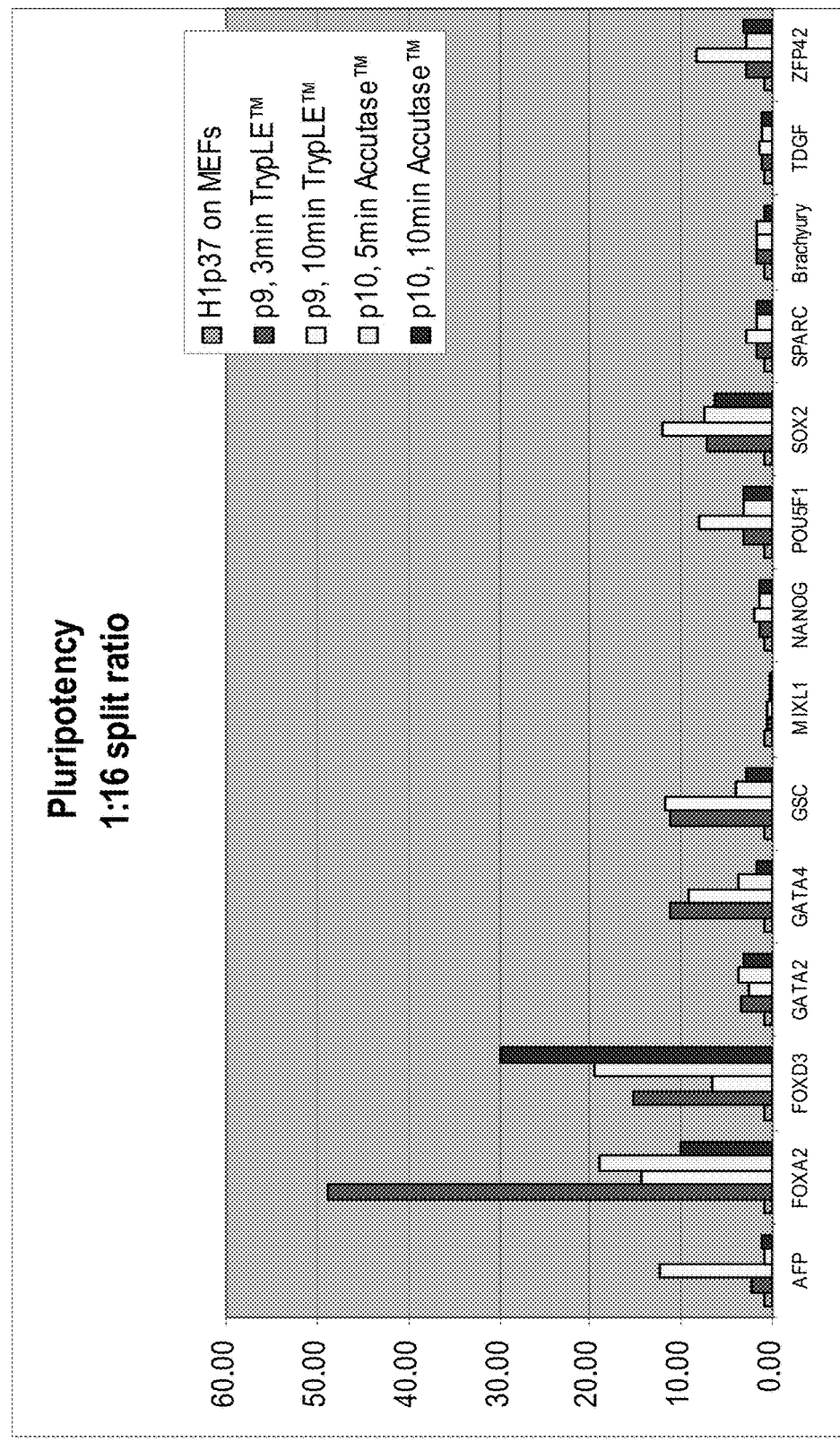
FIG. 43: H1 human embryonic stem cells grown for greater than 7 passages on PRIMARIA™ (greater than p45) passaged with Accutase™ or TrypLE™ at 1:16 ratio on PRIMARIA in the presence of Rho Kinase inhibitor Glycyl-H 1152 dihydrochloride were tested for mRNA expression of pluripotency and differentiation markers. The control is the starting population of cells at passage 37. 10 min Accutase™=passaged with 10 minute exposure to Accutase™. P(X) indicate passage number since moving from MEF feeders to PRIMARIA™ plastic.

At the completion of greater than 8 passages, cells were assayed for pluripotency by flow cytometry for pluripotency surface markers (FIG. 40) and by qRT-PCR for pluripotency and differentiation markers (FIGS. 41, 42, and 43). Cells were also differentiated to definitive endoderm by treating the cells with RPMI media supplemented with 2% BSA, 100 ng/ml Activin A, 20 ng/ml Wnt3a, 8 ng/ml bFGF, and 3 uM Glycyl-H 1152 dihydrochloride for 24 hours. Media was then changed to RPMI media supplemented with 2% BSA, 100 ng/ml Activin A, 8 ng/ml bFGF, and 3 µM Glycyl-H 1152 dihydrochloride for an additional 48 hours with daily media change. Samples differentiated to definitive endoderm were then tested for the presence of the definitive endoderm marker CXCR4 by flow cytometry (FIG. 40).

These results indicate that bulk passage from colony style, fibroblast feeder based culture to feeder free/matrix free culture on PRIMARIA in the presence of the Rho Kinase (ROCK) inhibitor, Glycyl-H 1152 dihydrochloride results in a highly homogeneous human embryonic stem cell culture that retains pluripotency and the ability to differentiate to definitive endoderm, and does not contain a fibroblast cell population.

Figure 44:
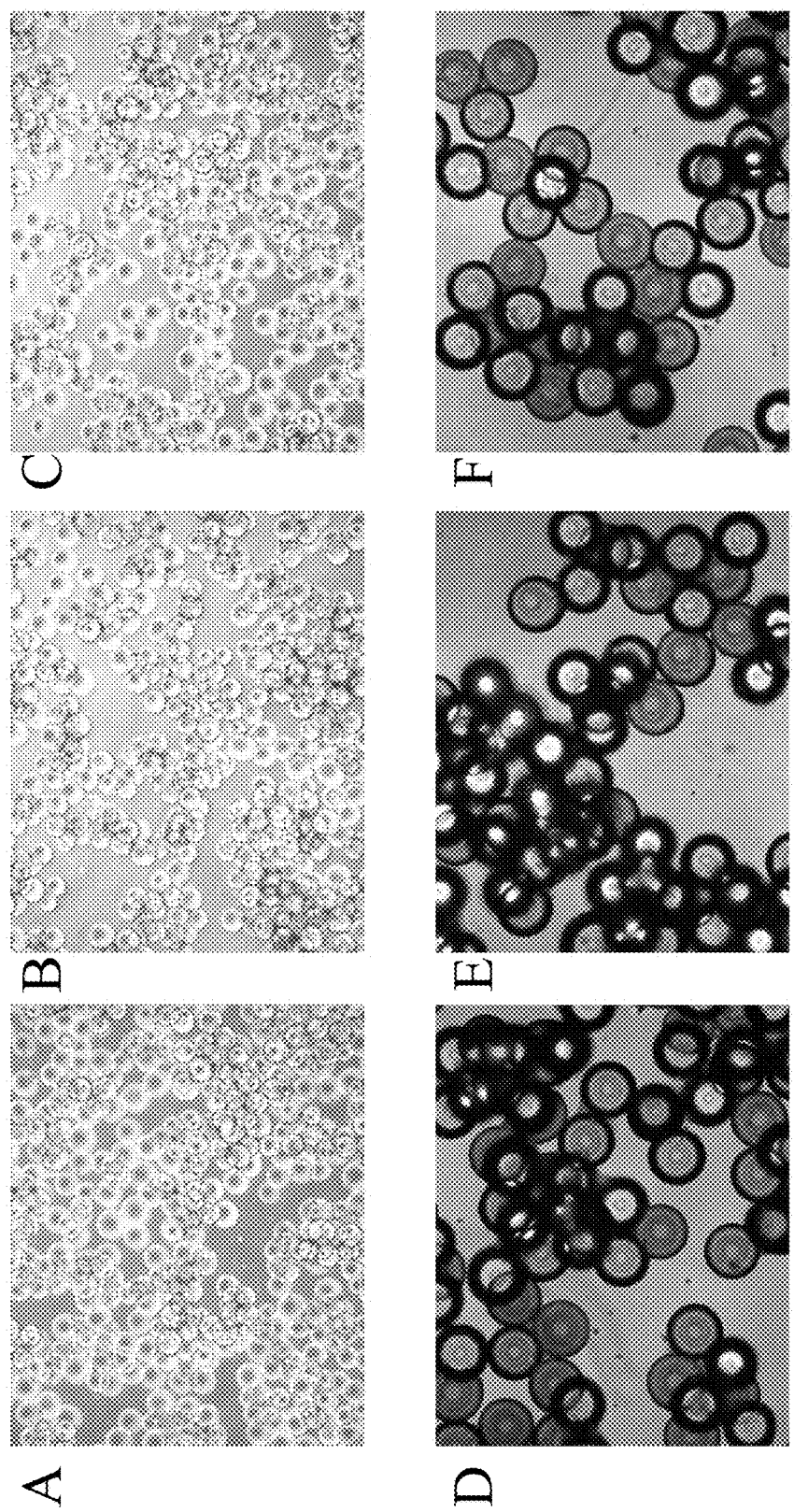
FIG. 44: Images of H1 cells grown on Primaria™ planar substrates (cat. no. 353846, Becton Dickinson, Franklin Lakes, N.J.) then transferred to micro-carriers 3 days after seeding. A-C H1 cells were seeded onto Cytodex 3® (GE Healthcare Life Sciences, NJ) micro-carriers. D-F Cells were seeded onto HILLEX®II micro-carriers (Solohill, MI). A, D H1 cells were passaged on Primaria™ planar substrate (cat. no. 353846, Becton Dickinson, Franklin Lakes, N.J.) plates with 10 minutes of TrypLE™ Express (Invitrogen, CA) treatment prior to transferring onto micro-carriers. A, E H1 cells were passaged on Primaria™ planar substrates (cat. no. 353846, Becton Dickinson, Franklin Lakes, N.J.) plates with 10 minutes of Accutase™ treatment prior to transferring onto micro-carriers. C, F H1 cells at passage 46 were passaged on MATIRGEL (BD Biosciences, CA) coated plates with collagenase (1 mg/ml) prior to transferring onto micro-carriers.
Figure 45:
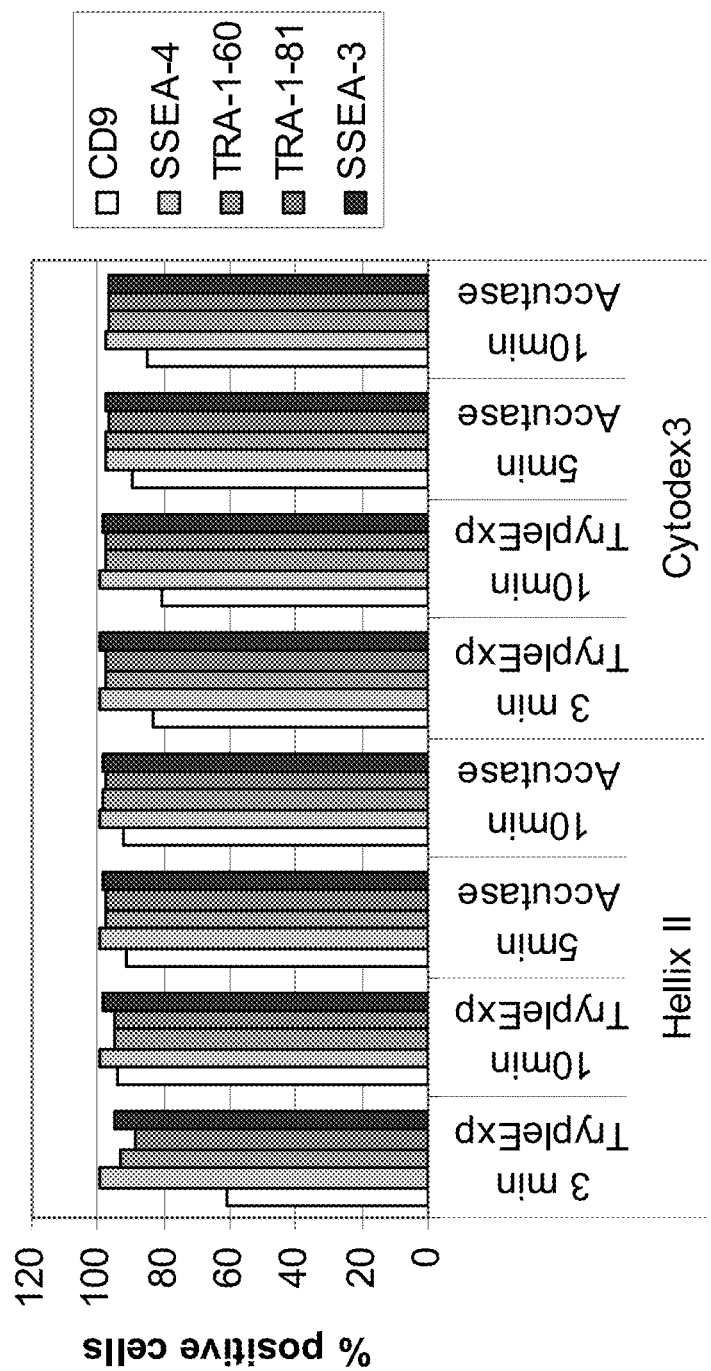
FIG. 45: Pluripotentency of H1 cells grown on Primaria™ planar substrates (cat. no. 353846, Becton Dickinson, Franklin Lakes, N.J.) then transferred to Cytodex 3® (GE Healthcare Life Sciences, NJ) and HILLEX®II micro-carriers. FACS analysis shows expression of pluripotent cell-surface proteins. Cells were treated with Accutase™ or TrypLE™ Express (Invitrogen, CA) for 3 to 10 minutes during passaging on Primaria™ (cat. no. 353846, Becton Dickinson, Franklin Lakes, N.J.).

Example 10: Human Embryonic Stem Cells Transferred from Tissue Culture Plastic to Micro-Carriers H1 cells were cultured on PRIMARIA™ (cat. no. 353846, Becton Dickinson, Franklin Lakes, N.J.) tissue culture plates (method in Example 9) and released by treatment with TrypLE™ Express for 3-5 minutes and seeded into 6 well non-tissue culture treated plates with Cytodex 3® (GE Healthcare Life Sciences, NJ) or HILLEX®II (Solohill, MI) micro-carriers in MEF-CM plus 10 μM Y27632 (Sigma-Aldrich, MO). As a control, H1p46 cells grown on MATRIGEL (BD Biosciences, CA) coated plates and passaged with Collagenase (1 mg/ml) were released and seeded onto micro-carriers in a similar manner. The plates were incubated at 37° C. for 5 hours, agitating by hand every 45 minutes. The plates were then placed on a rocking platform at 37° C. Medium was changed every day with MEF-CM plus 10 μM Y27632 (Sigma-Aldrich, MO). Images show good attachment of cells to the micro-carriers at 3 days (FIG. 44). After 7 days the cells were released (described in Example 4 infra) and analyzed by FACS for the pluripotency markers CD9, SSEA-4, SSEA-3, TRA-1-60, TRA-1-81 (FIG. 45). The majority of pluipotency markers were expressed on 90-100% of the cells. There are no clear differences between cells passaged with Accutase™ (Millipore, MA) and TrypLE™ Express (Invitrogen, CA) nor between growth on with Cytodex 3® (GE Healthcare Life Sciences, NJ) and HILLEX®II (Solohill, MI) micro-carriers. Overall, the cells remained pluripotent when transferred from PRIMARIA™ (cat. no. 353846, Becton Dickinson, Franklin Lakes, N.J.) cell culture plastic onto micro-carriers.

Figure 46:
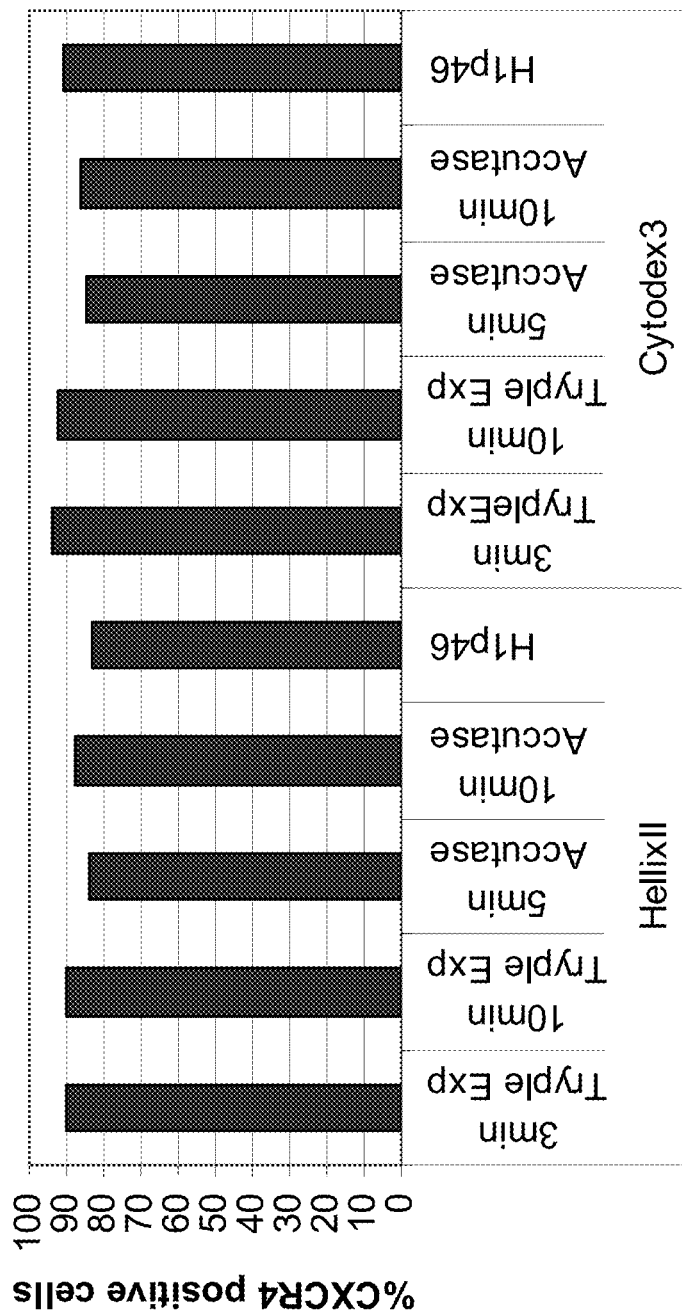
FIG. 46: Differentiation of H1 cells propagated on Primaria™ (cat. no. 353846, Becton Dickinson, Franklin Lakes, N.J.) then transferred to Cytodex 3® micro-carriers (GE Healthcare Life Sciences, NJ). FACS analysis of cell surface expression of CXCR4, definitive endoderm marker. Cells were treated with Accutase™ or TrypLE™ Express (Invitrogen, CA) for 3 to 10 minutes during passaging on Primaria™ (cat. no. 353846, Becton Dickinson, Franklin Lakes, N.J.).

Next these H1 cells on the micro-carriers were differentiated to definitive endoderm. The method is described in Example 7. After 4 days of differentiation, the H1 cells were released from the micro-carriers and underwent FACS analysis showing greater than 82% of the cells expressing CXCR4. See FIG. 46. The cells were efficiently differentiated into definitive endoderm regardless of the micro-carrier type or passaging enzyme on PRIMARIA™ (cat. no. 353846, Becton Dickinson, Franklin Lakes, N.J.). This proves the flexibility of the expansion system and allows for cells to be grown without matrix on plastic and micro-carriers.

Figure 47:
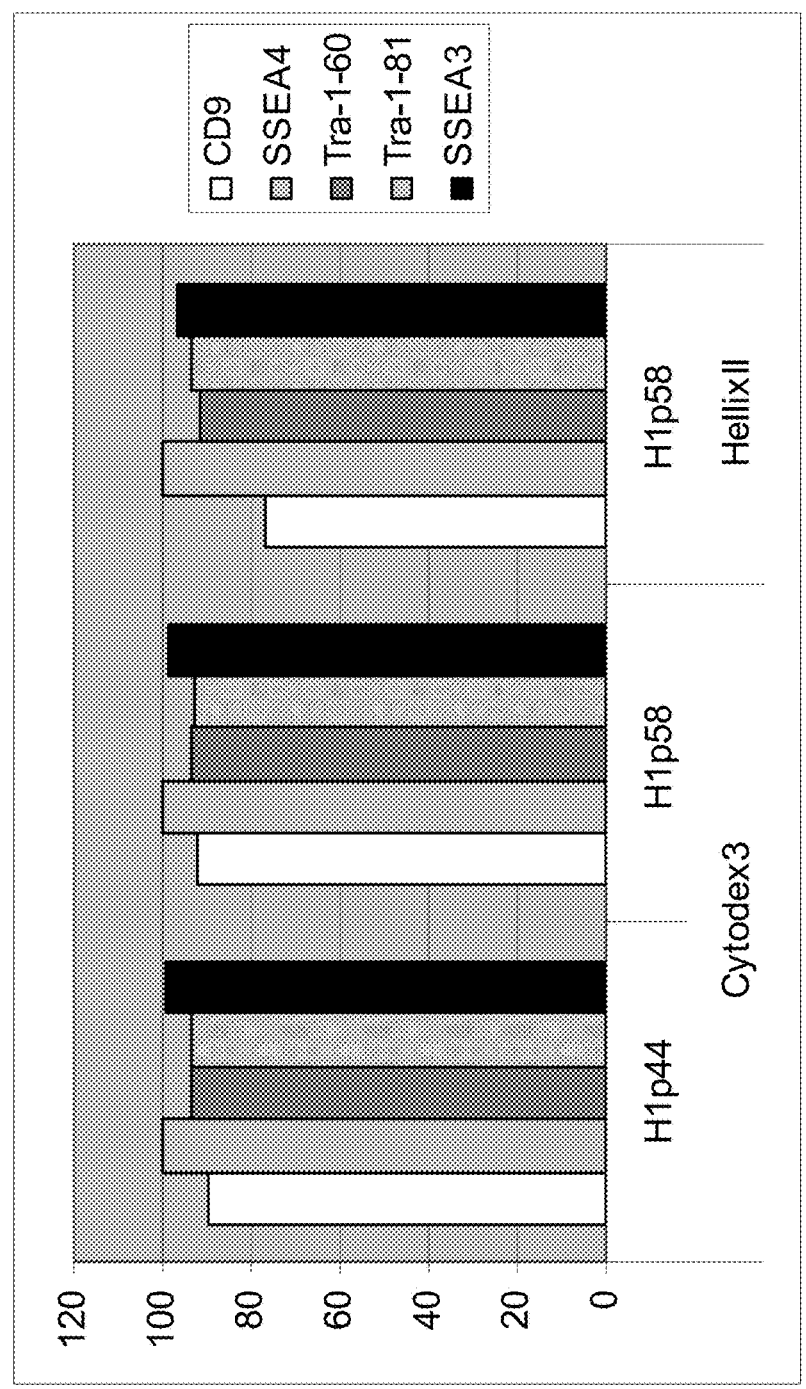
FIG. 47: FACS analysis of human embryonic stem cells cultured on planar substrates consisting of mixed cellulose esters prior to culture on micro-carriers.

Example 11: Human Embryonic Stem Cells Transferred from Planar Substrates Consisting of Mixed Cellulose Esters to Micro-Carriers H1 cells were cultured on planar substrates consisting of mixed cellulose esters for 12 passages, according to the methods disclosed U.S. Patent Application No. 61/116,452. The cells were released from the planar substrate by treatment with TrypLE™ Express for 3-5 minutes and seeded into 6 well non-tissue culture treated plates with CYTODEX 3® (GE Healthcare Life Sciences, NJ) or HILLEX®II (Solohill, MI) micro-carriers in MEF-CM plus 10 mM Y27632 (Sigma-Aldrich, MO). As a control, H1p44 cells grown on MATRIGEL™ coated plates (BD Biosciences, CA), passaged with Collagenase (1 mg/ml) were released and seeded onto micro-carriers in a similar manner. The plates were incubated at 37° C. for 5 hours, agitating by hand every 45 minutes. The plates were then placed on a rocking platform at 37° C. Media was changed daily. After 7 days the cells were released (described in Example 4) and analyzed by FACS for the pluripotency markers CD9, SSEA-4, SSEA-3, TRA-1-60, TRA-1-81 (FIG. 47). The majority of pluripotency markers were expressed on greater than 90% of the cells. There were no clear differences between cells grown on CYTODEX 3® and HILLEX®II micro-carriers. H1p44 control cells were not tested for pluripotency after growth on HILLEX®II micro-carriers, since pluripotency had been confirmed by other experiments (see Example 5). Overall, the cells maintained pluripotency when transferred from planar substrates consisting of mixed cellulose esters onto micro-carriers.

Figure 48:
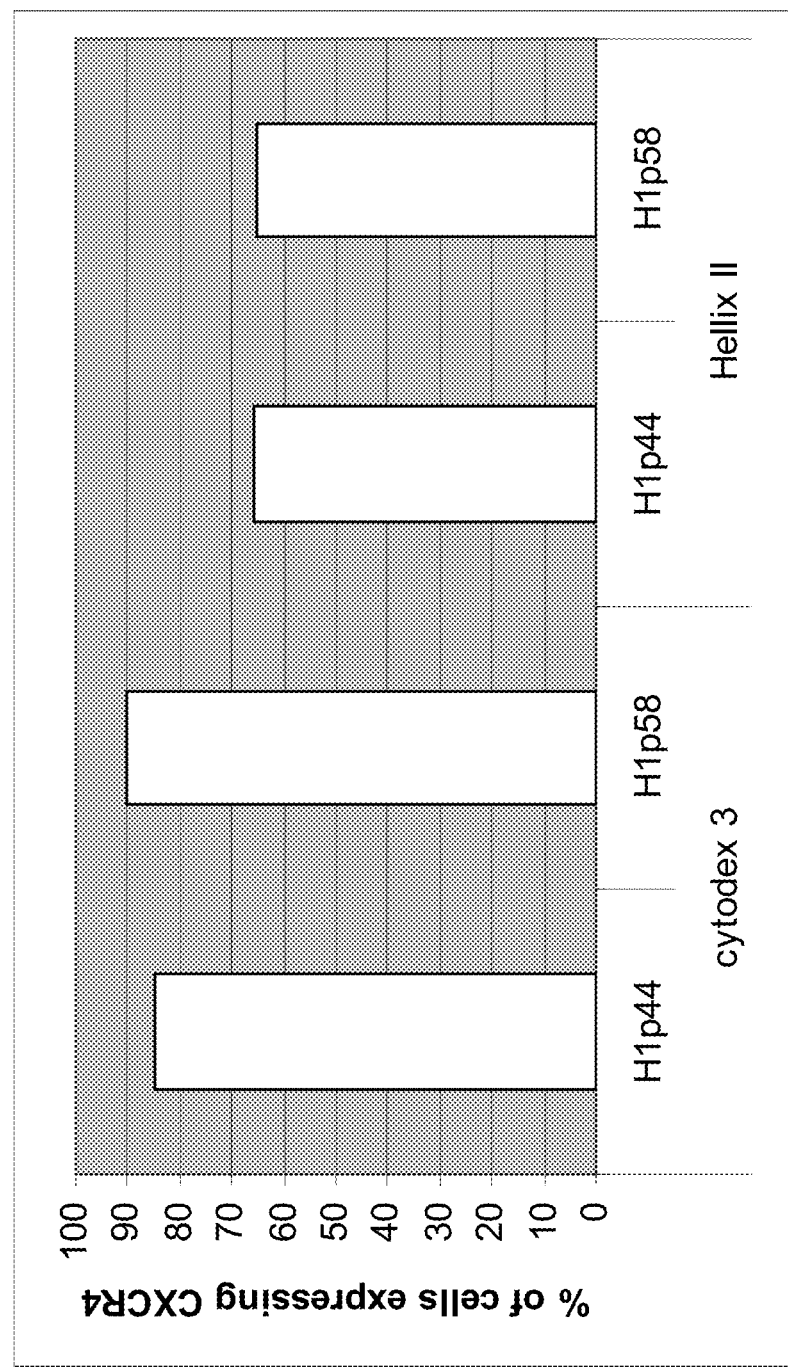
FIG. 48: FACS analysis of the expression of markers characteristic of the definitive endoderm lineage from human embryonic stem cells cultured on planar substrates consisting of mixed cellulose esters prior to culture and differentiation on micro-carriers.

Next, H1 cells on the micro-carriers were differentiated to definitive endoderm, according to the methods described in Example 7. After 4 days of differentiation, the H1 cells were released from the micro-carriers and underwent FACS analysis showing greater than 65% of the cells expressing CXCR4 (FIG. 48). The cells were efficiently differentiated into definitive endoderm regardless of the micro-carrier type. There appeared to be a lower number of cells differentiating into definitive endoderm on the HILLEX®II (Solohill, MI) micro-carriers. The ability of the cells to differentiate proves the flexibility of the expansion system. Additionally cells can be grown and differentiated directly on membranes and micro-carriers eliminating any need for an animal component matrix.

TABLE 1

Attachment of H9 cells to micro-carrier beads in MEF-CM in static cultures.

| Bead | company | surface coating | attachment 0-5* |
|---|---|---|---|
| ProNectin F | SoloHill ™-polystyrene | Recombinant fibronectin | 0 |
| Plastic | SoloHill ™-polystyrene | none | 0 |
| Plastic Plus | SoloHill ™-polystyrene | Cationic | 0 |
| HillexII | SoloHill ™-polystyrene | Cationic trimethyl ammonium | 2 |
| Collagen | SoloHill ™-polystyrene | Porcine collagen | 0 |
| FACTIII | SoloHill ™-polystyrene | Cationic porcine collagen | 0 |
| Glass | SoloHill ™-polystyrene | High silica glass | 0 |
| Cytodex 1 | GE-dextran | | 0 |
| Cytodex 3 | GE-dextran | denatured collagen | 0 |

*5 is most efficient cell attachment

TABLE 2

Attachment of H1 and H9 cells to micro-carrier beads in MEF-CM with 10 μM Rho kinase inhibitor, Y27632.

| Bead | company | surface coating | attachment 0-5* |
|---|---|---|---|
| ProNectin F | SoloHill ™-polystyrene | Recombinant fibronectin | 1 |
| Plastic | SoloHill ™-polystyrene | none | 1 |
| Plastic Plus | SoloHill ™-polystyrene | Cationic | 1 |
| HillexII | SoloHill ™-polystyrene | Cationic trimethyl ammonium | 4 |
| Collagen | SoloHill ™-polystyrene | Porcine collagen | 1 |
| FACTIII | SoloHill ™-polystyrene | Cationic porcine collagen | 1 |
| Glass | SoloHill ™-polystyrene | High silica glass | 1 |
| Cytodex 1 | GE-dextran | | 4 |
| Cytodex 3 | GE-dextran | denatured collagen | 4 |

*5 is most efficient cell attachment

TABLE 3

The population doublings for H1 and H9 cells grown 5 passages on Cytodex 1 ®, Cytodex 3 ®, or HILLEX ®II.

| Cell line-micro-carrier | Population doubling | Standard Deviation |
|---|---|---|
| H9-HII | 27 hrs | 4.1 |
| H9-C3 | 32.4 hrs | 12.8 |
| H1-C1 | 20.3 hrs | 3.7 |
| H1-C3 | 25 hrs | 12.8 |

Publications cited throughout this document are hereby incorporated by reference in their entirety. Although the various aspects of the invention have been illustrated above by reference to examples and preferred embodiments, it will be appreciated that the scope of the invention is defined not by the foregoing description but by the following claims properly construed under principles of patent law.

What is claimed is:

1. A method to differentiate human pluripotent stem cells to insulin-expressing cells on micro-carriers comprising the steps of:
   a. attaching the human pluripotent stem cells to a volume of dextran micro-carriers;
   b. differentiating the human pluripotent stem cells on the dextran microcarriers to definitive endoderm cells using Activin A;
   c. differentiating the definitive endoderm cells on the dextran microcarriers into pancreatic endoderm cells;
   d. differentiating the pancreatic endoderm cells on the dextran microcarriers into pancreatic endocrine cells; and
   e. differentiating the pancreatic endocrine cells on the dextran microcarriers into insulin-expressing cells, wherein the step of attaching comprises culturing the human pluripotent stem cells in medium containing a Rho kinase inhibitor at a concentration of between about 0.25 µM to about 10 µM.

2. The method of claim 1, wherein the micro-carriers are coated with denatured collagen.

3. The method of claim 1, wherein the dextran microcarriers are agitated.

4. The method of claim 1, wherein the Rho kinase inhibitor is Y27632 or Glycyl-H-1152 dihydrochloride.

5. The method of claim 1, wherein the step of attaching comprises culturing the human pluripotent stem cells in medium containing from about 1 µM to about 10 µM of the Rho kinase inhibitor Y27632.

6. The method of claim 1, wherein the attaching comprises culturing the human pluripotent stem cells in medium containing from about 0.25 µM to about 5 µM of the Rho kinase Glycyl-H-1152 dihydrochloride.

7. The method of claim 1, wherein the step of attaching comprises seeding at least $3.0 \times 10^4$ cells/cm$^2$.

8. The method of claim 1, wherein the method further comprises releasing the pancreatic endocrine cells by treatment with an enzyme.

9. A method to differentiate human pluripotent stem cells to pancreatic endoderm cells on micro-carriers comprising the steps of:
   a. differentiating human pluripotent stem cells attached to dextran microcarriers to definitive endoderm cells using Activin A; and
   b. differentiating the definitive endoderm cells on the dextran microcarriers into pancreatic endoderm cells, wherein the human pluripotent stem cells were attached to the dextran microcarriers using a medium containing a Rho kinase inhibitor at a concentration of between about 0.25 µM to about 10 µM.

10. The method of claim 9, wherein the method further comprises differentiating the pancreatic endoderm cells on the dextran microcarriers into pancreatic endocrine cells.

11. The method of claim 10, further comprising differentiating the pancreatic endocrine cells on the dextran microcarriers into insulin-expressing cells.

12. The method of claim 9, wherein the dextran microcarriers are coated with denatured collagen.

13. The method of claim 9, wherein the micro-carriers are agitated.

14. The method of claim 9, wherein the Rho kinase inhibitor is Y27632 or Glycyl-H-1152 dihydrochloride.

15. A method to differentiate human pluripotent stem cells to pancreatic endoderm cells on micro-carriers comprising the steps of:
   a. differentiating human pluripotent stem cells attached to dextran microcarriers to definitive endoderm cells using Activin A; and
   b. differentiating the definitive endoderm cells on the dextran microcarriers into pancreatic endoderm cells.

* * * * *